US009642661B2

(12) United States Patent
Stone et al.

(10) Patent No.: US 9,642,661 B2
(45) Date of Patent: May 9, 2017

(54) METHOD AND APPARATUS FOR STERNAL CLOSURE

(71) Applicant: Biomet Sports Medicine, LLC, Warsaw, IN (US)

(72) Inventors: Kevin T. Stone, Winona Lake, IN (US); Brian K. Berelsman, Warsaw, IN (US); Zachary Wagner, Lafayette, IN (US)

(73) Assignee: Biomet Sports Medicine, LLC, Warsaw, IN (US)

(*) Notice: Subject to any disclaimer, the term of this patent is extended or adjusted under 35 U.S.C. 154(b) by 523 days.

(21) Appl. No.: 14/094,311

(22) Filed: Dec. 2, 2013

(65) Prior Publication Data

US 2014/0088655 A1 Mar. 27, 2014

Related U.S. Application Data

(60) Division of application No. 12/938,902, filed on Nov. 3, 210, now Pat. No. 8,597,327, which is a
(Continued)

(51) Int. Cl.
*A61B 17/84* (2006.01)
*A61B 17/04* (2006.01)
(Continued)

(52) U.S. Cl.
CPC ........ *A61B 17/842* (2013.01); *A61B 17/0401* (2013.01); *A61B 17/823* (2013.01);
(Continued)

(58) Field of Classification Search
CPC .............. A61B 17/823; A61B 17/8076; A61B 17/8061; A61B 17/0401; A61B 17/06166;
(Continued)

(56) References Cited

U.S. PATENT DOCUMENTS

| | | | |
|---|---|---|---|
| 26,501 | A | 12/1859 | Kendrick et al. |
| 64,499 | A | 5/1867 | Daubert |

(Continued)

FOREIGN PATENT DOCUMENTS

| | | |
|---|---|---|
| AU | 4957264 | 3/1966 |
| AU | 440266 | 10/1967 |

(Continued)

OTHER PUBLICATIONS

US 6,238,418, 05/2001, Schwartz et al. (withdrawn)

(Continued)

*Primary Examiner* — Dianne Dornbusch
(74) *Attorney, Agent, or Firm* — Schwegman Lunberg & Woessner, P.A.

(57) ABSTRACT

A method and apparatus for securing a fractured or sectioned sternum in a patient's body is disclosed. The apparatus can include an attachment member and an adjustable flexible member construct. The attachment member can have a flexible member holder. The adjustable flexible member construct can have first and second ends and a body defining at least one passage portion. The first and second ends can be passed into and through the at least one passage portion via first and second openings associated with the at least one passage portion of the adjustable flexible member construct to form a pair of loops. The attachment member can be configured to be coupled to at least one of the formed pair of loops. The adjustable flexible member construct can be positioned about the sternum and can be reduced to compress the fractured or sectioned sternum.

11 Claims, 15 Drawing Sheets

Related U.S. Application Data continuation-in-part of application No. 12/915,962, filed on Oct. 29, 2010, now Pat. No. 8,562,647, which is a continuation-in-part of application No. 12/719,337, filed on Mar. 8, 2010, now Pat. No. 9,078,644, which is a continuation-in-part of application No. 12/489,168, filed on Jun. 22, 2009, now Pat. No. 8,361,113, which is a continuation-in-part of application No. 12/474,802, filed on May 29, 2009, now Pat. No. 8,088,130, which is a continuation-in-part of application No. 12/196,405, filed on Aug. 22, 2008, now Pat. No. 8,128,658, and a continuation-in-part of application No. 12/196,407, filed on Aug. 22, 2008, now Pat. No. 8,137,382, and a continuation-in-part of application No. 12/196,410, filed on Aug. 22, 2008, now Pat. No. 8,118,836, and a continuation-in-part of application No. 11/541,506, filed on Sep. 29, 2006, now Pat. No. 7,601,165, application No. 14/094,311, which is a continuation-in-part of application No. 13/645,964, filed on Oct. 5, 2012, which is a division of application No. 12/570,854, filed on Sep. 30, 2009, now Pat. No. 8,303,604, which is a continuation-in-part of application No. 12/014,399, filed on Jan. 15, 2008, now Pat. No. 7,909,851, which is a continuation-in-part of application No. 11/347,661, filed on Feb. 3, 2006, now Pat. No. 7,749,250, application No. 14/094,311, which is a continuation-in-part of application No. 13/587,374, filed on Aug. 16, 2012, now Pat. No. 8,777,956, which is a division of application No. 12/029,861, filed on Feb. 12, 2008, now Pat. No. 8,251,998, which is a continuation-in-part of application No. 11/504,882, filed on Aug. 16, 2006, now Pat. No. 8,998,949, which is a continuation-in-part of application No. 11/408,282, filed on Apr. 20, 2006, now abandoned, application No. 14/094,311, which is a continuation-in-part of application No. 12/702,067, filed on Feb. 8, 2010, now Pat. No. 8,672,968, which is a continuation of application No. 11/541,505, filed on Sep. 29, 2006, now Pat. No. 7,658,751, application No. 14/094,311, which is a continuation-in-part of application No. 13/098,927, filed on May 2, 2011, now Pat. No. 8,562,171, which is a continuation-in-part of application No. 12/196,398, filed on Aug. 22, 2008, now Pat. No. 7,959,650, which is a continuation-in-part of application No. 11/784,821, filed on Apr. 10, 2007, now Pat. No. 9,017,381.

(51) Int. Cl.

| | |
|---|---|
| ***A61B 17/82*** | (2006.01) |
| ***A61B 17/88*** | (2006.01) |
| *A61B 17/68* | (2006.01) |
| *A61B 17/80* | (2006.01) |
| *A61B 17/06* | (2006.01) |

(52) U.S. Cl.

CPC ...... *A61B 17/8869* (2013.01); *A61B 17/0483* (2013.01); *A61B 17/0487* (2013.01); *A61B 17/683* (2013.01); *A61B 17/8076* (2013.01); *A61B 2017/0404* (2013.01); *A61B 2017/0417* (2013.01); *A61B 2017/0496* (2013.01); *A61B 2017/06185* (2013.01)

(58) Field of Classification Search

CPC ... A61B 17/842; A61B 17/0487; A61B 17/82; A61B 2017/06185

See application file for complete search history.

(56) References Cited

U.S. PATENT DOCUMENTS

| | | | |
|---|---|---|---|
| 65,499 | A | 6/1867 | Miller |
| 126,366 | A | 4/1872 | Wills |
| 233,475 | A | 10/1880 | Cook et al. |
| 261,501 | A | 7/1882 | Vandermark |
| 268,407 | A | 12/1882 | Hughes |
| 330,087 | A | 11/1885 | Binns |
| 394,739 | A | 12/1888 | Toulmin |
| 401,677 | A | 4/1889 | Autenrieth |
| 417,805 | A | 12/1889 | Beaman |
| 445,875 | A | 2/1891 | Brickell |
| 487,304 | A | 12/1892 | Todd |
| 574,707 | A | 12/1893 | Lee et al. |
| 687,221 | A | 11/1901 | Gaff et al. |
| 762,710 | A | 6/1904 | Hall |
| 837,767 | A | 12/1906 | Aims |
| 838,203 | A | 12/1906 | Neil |
| 1,059,631 | A | 4/1913 | Popovics |
| 1,131,155 | A | 3/1915 | Murphy |
| 1,153,450 | A | 9/1915 | Schaff |
| 1,346,940 | A | 7/1920 | Collins |
| 1,635,066 | A | 7/1927 | Wells |
| 1,950,799 | A | 3/1934 | Jones |
| 2,065,659 | A | 12/1936 | Cullen |
| 2,108,206 | A | 2/1938 | Meeker |
| 2,121,193 | A | 6/1938 | Hanicke |
| 2,242,003 | A | 5/1941 | Lorenzo |
| 2,267,925 | A | 12/1941 | Johnston |
| 2,302,986 | A | 11/1942 | Vollrath |
| 2,329,398 | A | 9/1943 | Duffy |
| 2,379,629 | A | 7/1945 | Eweson |
| 2,397,216 | A | 3/1946 | Stellin |
| RE22,857 | E | 3/1947 | Ogburn |
| 2,526,959 | A | 10/1950 | Lorenzo |
| 2,528,456 | A | 10/1950 | Stevenson |
| 2,562,419 | A | 7/1951 | Ferris |
| 2,581,564 | A | 1/1952 | Villegas |
| 2,600,395 | A | 6/1952 | Domoj et al. |
| 2,610,631 | A | 9/1952 | Calicchio |
| 2,665,597 | A | 1/1954 | Hill |
| 2,669,774 | A | 2/1954 | Mitchell |
| 2,698,986 | A | 1/1955 | Brown |
| 2,760,488 | A | 8/1956 | Pierce |
| 2,833,284 | A | 5/1958 | Springer |
| 2,846,712 | A | 8/1958 | Markman |
| 2,860,393 | A | 11/1958 | Brock |
| 2,880,728 | A | 4/1959 | Rights |
| 2,881,762 | A | 4/1959 | Lowrie |
| 2,883,096 | A | 4/1959 | Dawson |
| 2,913,042 | A | 11/1959 | Taylor |
| 2,947,504 | A | 8/1960 | Ruhlman |
| 3,000,009 | A | 9/1961 | Selstad |
| 3,003,155 | A | 10/1961 | Mielzynski et al. |
| 3,013,559 | A | 12/1961 | Thomas |
| 3,037,619 | A | 6/1962 | Stevans |
| 3,039,460 | A | 6/1962 | Chandler |
| 3,081,781 | A | 3/1963 | Stermer |
| 3,090,386 | A | 5/1963 | Curtis |
| 3,103,666 | A | 9/1963 | Bone |
| 3,123,077 | A | 3/1964 | Alcamo |
| 3,125,095 | A | 3/1964 | Kaufman et al. |
| 3,209,422 | A | 10/1965 | Dritz |
| 3,223,083 | A | 12/1965 | Cobey |
| 3,234,938 | A | 2/1966 | Robinson |
| 3,240,379 | A | 3/1966 | Bremer et al. |
| 3,250,271 | A | 5/1966 | Lippes |
| 3,399,432 | A | 9/1968 | Merser |
| 3,409,014 | A | 11/1968 | Shannon |
| RE26,501 | E | 12/1968 | Himmelstein et al. |
| 3,435,475 | A | 4/1969 | Bisk |
| 3,467,089 | A | 9/1969 | Hasson |
| 3,470,834 | A | 10/1969 | Bone |
| 3,470,875 | A | 10/1969 | Johnson |
| 3,500,820 | A | 3/1970 | Almen |
| 3,507,274 | A | 4/1970 | Soichet |
| 3,513,484 | A | 5/1970 | Hausner |

(56) References Cited

U.S. PATENT DOCUMENTS

| | | | |
|---|---|---|---|
| 3,515,132 | A | 6/1970 | McKnight |
| 3,522,803 | A | 8/1970 | Majzlin |
| 3,527,223 | A | 9/1970 | Shein |
| 3,533,406 | A | 10/1970 | Hutterer et al. |
| 3,541,591 | A | 11/1970 | Hoegerman |
| 3,545,008 | A | 12/1970 | Bader, Jr. |
| 3,547,389 | A | 12/1970 | Mitchell |
| 3,579,831 | A | 5/1971 | Stevens et al. |
| 3,590,616 | A | 7/1971 | Schussler et al. |
| 3,608,095 | A | 9/1971 | Barry |
| 3,618,447 | A | 11/1971 | Goins |
| 3,628,530 | A | 12/1971 | Schwartz |
| 3,643,649 | A | 2/1972 | Amato |
| 3,648,705 | A | 3/1972 | Lary |
| 3,650,274 | A | 3/1972 | Edwards et al. |
| 3,656,483 | A | 4/1972 | Rudel |
| 3,659,597 | A | 5/1972 | Wolfers |
| 3,664,345 | A | 5/1972 | Dabbs et al. |
| 3,665,560 | A | 5/1972 | Bennett et al. |
| 3,675,639 | A | 7/1972 | Cimber |
| 3,683,422 | A | 8/1972 | Stemmer et al. |
| 3,692,022 | A | 9/1972 | Ewing |
| 3,695,271 | A | 10/1972 | Chodorow |
| 3,699,969 | A | 10/1972 | Allen |
| 3,716,058 | A | 2/1973 | Tanner, Jr. |
| 3,744,488 | A | 7/1973 | Cox |
| 3,752,516 | A | 8/1973 | Mumma |
| 3,757,629 | A | 9/1973 | Schneider |
| 3,763,856 | A | 10/1973 | Blomberg |
| 3,771,520 | A | 11/1973 | Lerner |
| 3,777,748 | A | 12/1973 | Abramson |
| 3,786,801 | A | 1/1974 | Sartorius |
| 3,807,407 | A | 4/1974 | Schweizer |
| 3,810,456 | A | 5/1974 | Karman |
| 3,825,010 | A | 7/1974 | McDonald |
| 3,840,017 | A | 10/1974 | Violante et al. |
| 3,842,824 | A | 10/1974 | Neufeld |
| 3,842,840 | A | 10/1974 | Schweizer |
| 3,845,772 | A | 11/1974 | Smith |
| 3,867,933 | A | 2/1975 | Kitrilakis |
| 3,867,944 | A | 2/1975 | Samuels |
| 3,871,368 | A | 3/1975 | Johnson et al. |
| 3,871,379 | A | 3/1975 | Clarke |
| 3,874,388 | A | 4/1975 | King et al. |
| 3,875,648 | A | 4/1975 | Bone |
| 3,877,570 | A | 4/1975 | Barry |
| 3,880,156 | A | 4/1975 | Hoff |
| 3,881,475 | A | 5/1975 | Gordon et al. |
| 3,889,666 | A | 6/1975 | Lerner |
| 3,892,240 | A | 7/1975 | Park |
| 3,896,500 | A | 7/1975 | Rambert et al. |
| 3,896,810 | A | 7/1975 | Akiyama |
| 3,907,442 | A | 9/1975 | Reid |
| 3,910,281 | A | 10/1975 | Kletschka et al. |
| 3,918,444 | A | 11/1975 | Hoff et al. |
| 3,918,455 | A | 11/1975 | Coplan |
| 3,927,666 | A | 12/1975 | Hoff |
| 3,931,667 | A | 1/1976 | Merser et al. |
| 3,933,153 | A | 1/1976 | Csatary et al. |
| 3,937,217 | A | 2/1976 | Kosonen et al. |
| 3,943,932 | A | 3/1976 | Woo |
| 3,946,446 | A | 3/1976 | Schofield |
| 3,946,728 | A | 3/1976 | Bettex |
| 3,946,740 | A | 3/1976 | Bassett |
| 3,953,896 | A | 5/1976 | Treace |
| 3,954,103 | A | 5/1976 | Garcia-Roel et al. |
| 3,961,632 | A | 6/1976 | Moossun |
| 3,973,560 | A | 8/1976 | Emmett et al. |
| 3,976,079 | A | 8/1976 | Samuels et al. |
| 3,977,050 | A | 8/1976 | Perez et al. |
| 3,979,799 | A | 9/1976 | Merser et al. |
| 3,985,138 | A | 10/1976 | Jarvik |
| 3,990,619 | A | 11/1976 | Russell |
| 4,005,707 | A | 2/1977 | Moulding, Jr. |
| 4,006,747 | A | 2/1977 | Kronenthal et al. |
| 4,007,743 | A | 2/1977 | Blake |
| 4,013,071 | A | 3/1977 | Rosenberg et al. |
| 4,026,281 | A | 5/1977 | Mayberry et al. |
| 4,036,101 | A | 7/1977 | Burnett |
| 4,050,100 | A | 9/1977 | Barry |
| 4,054,954 | A | 10/1977 | Nakayama et al. |
| 4,084,478 | A | 4/1978 | Simmons |
| 4,085,466 | A | 4/1978 | Goodfellow et al. |
| 4,094,313 | A | 6/1978 | Komamura et al. |
| 4,099,750 | A | 7/1978 | McGrew |
| 4,103,690 | A | 8/1978 | Harris |
| RE29,819 | E | 10/1978 | Bone |
| 4,121,487 | A | 10/1978 | Bone |
| 4,143,656 | A | 3/1979 | Holmes et al. |
| 4,144,876 | A | 3/1979 | DeLeo |
| 4,146,022 | A | 3/1979 | Johnson et al. |
| 4,149,277 | A | 4/1979 | Bokros |
| 4,157,714 | A | 6/1979 | Foltz et al. |
| 4,158,250 | A | 6/1979 | Ringwald |
| 4,160,453 | A | 7/1979 | Miller |
| 4,164,225 | A | 8/1979 | Johnson et al. |
| 4,172,458 | A | 10/1979 | Pereyra |
| 4,175,555 | A | 11/1979 | Herbert et al. |
| 4,185,636 | A | 1/1980 | Gabbay et al. |
| 4,196,883 | A | 4/1980 | Einhorn et al. |
| 4,207,627 | A | 6/1980 | Cloutier |
| 4,210,148 | A | 7/1980 | Stivala |
| 4,235,161 | A | 11/1980 | Kunreuther |
| 4,235,238 | A | 11/1980 | Ogiu et al. |
| 4,237,779 | A | 12/1980 | Kunreuther |
| 4,243,037 | A | 1/1981 | Smith |
| 4,249,525 | A | 2/1981 | Krzeminski |
| 4,263,913 | A | 4/1981 | Malmin |
| 4,265,246 | A | 5/1981 | Barry |
| 4,273,117 | A | 6/1981 | Neuhauser et al. |
| 4,275,490 | A | 6/1981 | Bivins |
| 4,275,717 | A | 6/1981 | Bolesky |
| 4,287,807 | A | 9/1981 | Pacharis et al. |
| 4,291,698 | A | 9/1981 | Fuchs et al. |
| 4,301,551 | A | 11/1981 | Dore et al. |
| 4,302,397 | A | 11/1981 | Frainier et al. |
| 4,307,723 | A | 12/1981 | Finney |
| 4,312,337 | A | 1/1982 | Donohue |
| 4,316,469 | A | 2/1982 | Kapitanov et al. |
| 4,326,531 | A | 4/1982 | Shimonaka et al. |
| 4,344,193 | A | 8/1982 | Kenny |
| 4,345,601 | A | 8/1982 | Fukuda |
| 4,349,027 | A | 9/1982 | DiFrancesco |
| 4,388,921 | A | 6/1983 | Sutter et al. |
| 4,400,833 | A | 8/1983 | Kurland |
| 4,402,445 | A | 9/1983 | Green |
| 4,409,974 | A | 10/1983 | Freedland |
| 4,438,769 | A | 3/1984 | Pratt et al. |
| 4,441,489 | A | 4/1984 | Evans et al. |
| 4,454,875 | A | 6/1984 | Pratt et al. |
| 4,462,395 | A | 7/1984 | Johnson |
| 4,463,753 | A | 8/1984 | Gustilo |
| 4,473,102 | A | 9/1984 | Ohman et al. |
| 4,484,570 | A | 11/1984 | Sutter et al. |
| 4,489,446 | A | 12/1984 | Reed |
| 4,489,464 | A | 12/1984 | Massari et al. |
| 4,493,323 | A | 1/1985 | Albright et al. |
| 4,496,468 | A | 1/1985 | House et al. |
| 4,505,274 | A | 3/1985 | Speelman |
| 4,509,516 | A | 4/1985 | Richmond |
| 4,531,522 | A | 7/1985 | Bedi et al. |
| 4,532,926 | A | 8/1985 | O'Holla |
| 4,534,350 | A | 8/1985 | Golden et al. |
| 4,535,764 | A | 8/1985 | Ebert |
| 4,537,185 | A | 8/1985 | Stednitz |
| 4,549,545 | A | 10/1985 | Levy |
| 4,549,652 | A | 10/1985 | Free |
| 4,561,432 | A | 12/1985 | Mazor |
| 4,564,007 | A | 1/1986 | Coombs et al. |
| 4,570,623 | A | 2/1986 | Ellison et al. |
| 4,573,844 | A | 3/1986 | Smith |
| 4,576,608 | A | 3/1986 | Homsy |
| 4,584,722 | A | 4/1986 | Levy et al. |
| 4,587,963 | A | 5/1986 | Leibinger et al. |

(56) References Cited

U.S. PATENT DOCUMENTS

| | | | |
|---|---|---|---|
| 4,590,928 | A | 5/1986 | Hunt et al. |
| 4,595,007 | A | 6/1986 | Mericle |
| 4,596,249 | A | 6/1986 | Freda et al. |
| 4,597,766 | A | 7/1986 | Hilal et al. |
| 4,602,635 | A | 7/1986 | Mulhollan et al. |
| 4,602,636 | A | 7/1986 | Noiles |
| 4,604,997 | A | 8/1986 | De Bastiani et al. |
| 4,605,414 | A | 8/1986 | Czajka |
| 4,616,650 | A | 10/1986 | Green et al. |
| 4,621,640 | A | 11/1986 | Mulhollan et al. |
| 4,624,254 | A | 11/1986 | McGarry et al. |
| 4,632,100 | A | 12/1986 | Somers et al. |
| 4,635,637 | A | 1/1987 | Schreiber |
| 4,636,121 | A | 1/1987 | Miller |
| 4,640,271 | A | 2/1987 | Lower |
| 4,641,652 | A | 2/1987 | Hutterer et al. |
| 4,649,916 | A | 3/1987 | Frimberger |
| 4,649,952 | A | 3/1987 | Jobe |
| 4,653,486 | A | 3/1987 | Coker |
| 4,653,487 | A | 3/1987 | Maale |
| 4,653,489 | A | 3/1987 | Tronzo |
| 4,655,777 | A | 4/1987 | Dunn et al. |
| 4,662,068 | A | 5/1987 | Polonsky |
| 4,667,662 | A | 5/1987 | Titone et al. |
| 4,667,675 | A | 5/1987 | Davis |
| 4,669,473 | A | 6/1987 | Richards et al. |
| 4,683,895 | A | 8/1987 | Pohndorf |
| 4,688,561 | A | 8/1987 | Reese |
| 4,690,169 | A | 9/1987 | Jobe |
| 4,696,300 | A | 9/1987 | Anderson |
| 4,705,040 | A | 11/1987 | Mueller et al. |
| 4,708,132 | A | 11/1987 | Silvestrini |
| 4,714,475 | A | 12/1987 | Grundei et al. |
| 4,716,893 | A | 1/1988 | Fischer et al. |
| 4,719,671 | A | 1/1988 | Ito et al. |
| 4,719,917 | A | 1/1988 | Barrows et al. |
| 4,723,540 | A | 2/1988 | Gilmer, Jr. |
| 4,724,839 | A | 2/1988 | Bedi et al. |
| 4,728,332 | A | 3/1988 | Albrektsson |
| 4,736,746 | A | 4/1988 | Anderson |
| 4,738,255 | A | 4/1988 | Goble et al. |
| 4,739,751 | A | 4/1988 | Sapega et al. |
| 4,741,330 | A | 5/1988 | Hayhurst |
| 4,741,336 | A | 5/1988 | Failla et al. |
| 4,744,353 | A | 5/1988 | McFarland |
| 4,744,793 | A | 5/1988 | Parr et al. |
| 4,750,492 | A | 6/1988 | Jacobs |
| 4,751,922 | A | 6/1988 | Dipietropolo |
| 4,760,843 | A | 8/1988 | Fischer et al. |
| 4,760,844 | A | 8/1988 | Kyle |
| 4,760,848 | A | 8/1988 | Hasson |
| 4,770,663 | A | 9/1988 | Hanslik et al. |
| 4,772,261 | A | 9/1988 | Von Hoff et al. |
| 4,772,286 | A | 9/1988 | Goble et al. |
| 4,773,910 | A | 9/1988 | Chen et al. |
| 4,775,380 | A | 10/1988 | Seedhom et al. |
| 4,776,328 | A | 10/1988 | Frey et al. |
| 4,781,190 | A | 11/1988 | Lee et al. |
| 4,784,126 | A | 11/1988 | Hourahane |
| 4,787,882 | A | 11/1988 | Claren et al. |
| 4,790,297 | A | 12/1988 | Luque et al. |
| 4,790,850 | A | 12/1988 | Dunn et al. |
| 4,793,363 | A | 12/1988 | Ausherman et al. |
| 4,809,695 | A | 3/1989 | Gwathmey et al. |
| 4,813,406 | A | 3/1989 | Ogle, II |
| 4,823,780 | A | 4/1989 | Odensten et al. |
| 4,823,794 | A | 4/1989 | Pierce |
| 4,828,562 | A | 5/1989 | Kenna |
| 4,832,026 | A | 5/1989 | Jones |
| 4,834,098 | A | 5/1989 | Jones |
| 4,838,282 | A | 6/1989 | Strasser et al. |
| 4,841,960 | A | 6/1989 | Garner |
| 4,846,835 | A | 7/1989 | Grande |
| 4,851,005 | A | 7/1989 | Hunt et al. |
| 4,858,601 | A | 8/1989 | Glisson |
| 4,858,603 | A | 8/1989 | Clemow et al. |
| 4,858,608 | A | 8/1989 | McQuilkin et al. |
| 4,860,513 | A | 8/1989 | Whitman |
| 4,863,383 | A | 9/1989 | Grafelmann et al. |
| 4,870,957 | A | 10/1989 | Goble et al. |
| 4,872,450 | A | 10/1989 | Austad |
| 4,873,976 | A | 10/1989 | Schreiber |
| 4,884,572 | A | 12/1989 | Bays et al. |
| 4,887,601 | A | 12/1989 | Richards |
| 4,889,110 | A | 12/1989 | Galline et al. |
| 4,890,615 | A | 1/1990 | Caspari et al. |
| 4,893,619 | A | 1/1990 | Dale et al. |
| 4,893,974 | A | 1/1990 | Fischer et al. |
| 4,895,148 | A | 1/1990 | Bays et al. |
| 4,896,668 | A | 1/1990 | Popoff et al. |
| 4,898,156 | A | 2/1990 | Gatturna et al. |
| 4,899,743 | A | 2/1990 | Nicholson et al. |
| 4,901,721 | A | 2/1990 | Hakki |
| 4,919,667 | A | 4/1990 | Richmond |
| 4,922,897 | A | 5/1990 | Sapega et al. |
| 4,923,461 | A | 5/1990 | Caspari et al. |
| 4,927,421 | A | 5/1990 | Goble et al. |
| 4,946,377 | A | 8/1990 | Kovach |
| 4,946,468 | A | 8/1990 | Li |
| 4,950,270 | A | 8/1990 | Bowman et al. |
| 4,950,285 | A | 8/1990 | Wilk |
| 4,960,381 | A | 10/1990 | Niznick |
| 4,961,741 | A | 10/1990 | Hayhurst |
| 4,968,315 | A | 11/1990 | Gatturna |
| 4,968,317 | A | 11/1990 | Tormala et al. |
| 4,969,886 | A | 11/1990 | Cziffer et al. |
| 4,974,488 | A | 12/1990 | Spralja |
| 4,976,736 | A | 12/1990 | White et al. |
| 4,978,350 | A | 12/1990 | Wagenknecht et al. |
| 4,979,956 | A | 12/1990 | Silvestrini |
| 4,983,176 | A | 1/1991 | Cushman et al. |
| 4,988,351 | A | 1/1991 | Paulos et al. |
| 4,994,074 | A | 2/1991 | Bezwada et al. |
| 4,997,433 | A | 3/1991 | Goble et al. |
| 5,002,545 | A | 3/1991 | Whiteside et al. |
| 5,002,550 | A | 3/1991 | Li |
| 5,002,562 | A | 3/1991 | Oberlander |
| 5,002,574 | A | 3/1991 | May et al. |
| 5,007,921 | A | 4/1991 | Brown |
| 5,020,713 | A | 6/1991 | Kunreuther |
| 5,026,398 | A | 6/1991 | May et al. |
| 5,028,569 | A | 7/1991 | Cihon |
| 5,030,224 | A | 7/1991 | Wright et al. |
| 5,030,235 | A | 7/1991 | Campbell, Jr. |
| 5,035,701 | A | 7/1991 | Kabbara |
| 5,037,422 | A | 8/1991 | Hayhurst et al. |
| 5,037,426 | A | 8/1991 | Goble et al. |
| 5,041,129 | A | 8/1991 | Hayhurst et al. |
| 5,046,513 | A | 9/1991 | Gatturna et al. |
| 5,047,030 | A | 9/1991 | Draenert et al. |
| 5,053,046 | A | 10/1991 | Janese |
| 5,053,047 | A | 10/1991 | Yoon |
| 5,059,201 | A | 10/1991 | Asnis |
| 5,059,206 | A | 10/1991 | Winters |
| 5,061,277 | A | 10/1991 | Carpentier et al. |
| 5,062,344 | A | 11/1991 | Gerker |
| 5,062,843 | A | 11/1991 | Mahony, III |
| 5,064,431 | A | 11/1991 | Gilbertson et al. |
| 5,067,962 | A | 11/1991 | Campbell et al. |
| 5,071,420 | A | 12/1991 | Paulos et al. |
| 5,074,874 | A | 12/1991 | Yoon et al. |
| 5,078,731 | A | 1/1992 | Hayhurst |
| 5,078,843 | A | 1/1992 | Pratt |
| 5,080,050 | A | 1/1992 | Dale |
| 5,084,050 | A | 1/1992 | Draenert |
| 5,084,058 | A | 1/1992 | Li |
| 5,085,661 | A | 2/1992 | Moss |
| 5,087,263 | A | 2/1992 | Li |
| 5,087,309 | A | 2/1992 | Melton, Jr. |
| 5,089,012 | A | 2/1992 | Prou |
| 5,092,866 | A | 3/1992 | Breard et al. |
| 5,098,433 | A | 3/1992 | Freedland |
| 5,098,435 | A | 3/1992 | Stednitz et al. |
| 5,100,415 | A | 3/1992 | Hayhurst |

(56) References Cited

U.S. PATENT DOCUMENTS

| | | | |
|---|---|---|---|
| 5,100,417 | A | 3/1992 | Cerier et al. |
| 5,108,433 | A | 4/1992 | May et al. |
| 5,112,335 | A | 5/1992 | Laboureau et al. |
| 5,116,337 | A | 5/1992 | Johnson |
| 5,116,373 | A | 5/1992 | Jakob et al. |
| 5,116,375 | A | 5/1992 | Hofmann |
| 5,123,913 | A | 6/1992 | Wilk et al. |
| 5,123,914 | A | 6/1992 | Cope |
| 5,127,785 | A | 7/1992 | Faucher et al. |
| 5,129,901 | A | 7/1992 | Decoste |
| 5,129,902 | A | 7/1992 | Goble et al. |
| 5,129,904 | A | 7/1992 | Illi et al. |
| 5,129,906 | A | 7/1992 | Ross et al. |
| 5,139,498 | A | 8/1992 | Astudillo Ley |
| 5,139,499 | A | 8/1992 | Small et al. |
| 5,139,520 | A | 8/1992 | Rosenberg |
| 5,143,498 | A | 9/1992 | Whitman |
| 5,147,362 | A | 9/1992 | Goble |
| 5,149,329 | A | 9/1992 | Richardson |
| 5,151,104 | A | 9/1992 | Kenna |
| 5,152,790 | A | 10/1992 | Rosenberg et al. |
| 5,154,189 | A | 10/1992 | Oberlander |
| 5,156,616 | A | 10/1992 | Meadows et al. |
| 5,163,960 | A | 11/1992 | Bonutti |
| D331,626 | S | 12/1992 | Hayhurst et al. |
| 5,169,400 | A | 12/1992 | Muhling et al. |
| 5,171,274 | A | 12/1992 | Fluckiger et al. |
| 5,176,682 | A | 1/1993 | Chow |
| 5,178,629 | A | 1/1993 | Kammerer |
| 5,183,458 | A | 2/1993 | Marx |
| 5,190,545 | A | 3/1993 | Corsi et al. |
| 5,192,282 | A | 3/1993 | Draenert et al. |
| 5,197,987 | A | 3/1993 | Koch et al. |
| 5,199,135 | A | 4/1993 | Gold |
| 5,203,784 | A | 4/1993 | Ross et al. |
| 5,203,787 | A | 4/1993 | Noblitt et al. |
| 5,207,679 | A | 5/1993 | Li |
| 5,209,753 | A | 5/1993 | Biedermann et al. |
| 5,209,805 | A | 5/1993 | Spraggins |
| 5,211,647 | A | 5/1993 | Schmieding |
| 5,211,650 | A | 5/1993 | Noda |
| 5,214,987 | A | 6/1993 | Fenton, Sr. |
| 5,219,359 | A | 6/1993 | McQuilkin et al. |
| 5,222,976 | A | 6/1993 | Yoon |
| 5,224,940 | A | 7/1993 | Dann et al. |
| 5,224,946 | A | 7/1993 | Hayhurst et al. |
| 5,226,914 | A | 7/1993 | Caplan et al. |
| 5,230,699 | A | 7/1993 | Grasinger |
| 5,232,436 | A | 8/1993 | Janevski |
| 5,234,435 | A | 8/1993 | Seagrave, Jr. |
| 5,235,238 | A | 8/1993 | Nomura et al. |
| 5,236,445 | A | 8/1993 | Hayhurst et al. |
| 5,236,461 | A | 8/1993 | Forte |
| 5,242,447 | A | 9/1993 | Borzone |
| 5,246,441 | A | 9/1993 | Ross et al. |
| 5,249,899 | A | 10/1993 | Wilson |
| 5,250,053 | A | 10/1993 | Snyder |
| 5,258,015 | A | 11/1993 | Li et al. |
| 5,258,016 | A | 11/1993 | DiPoto et al. |
| 5,258,040 | A | 11/1993 | Bruchman et al. |
| 5,261,908 | A | 11/1993 | Campbell, Jr. |
| 5,268,001 | A | 12/1993 | Nicholson et al. |
| 5,269,160 | A | 12/1993 | Wood |
| 5,269,783 | A | 12/1993 | Sander |
| 5,269,806 | A | 12/1993 | Sardelis et al. |
| 5,269,809 | A | 12/1993 | Hayhurst et al. |
| 5,279,311 | A | 1/1994 | Snyder |
| 5,281,422 | A | 1/1994 | Badylak et al. |
| 5,282,809 | A | 2/1994 | Kammerer et al. |
| 5,282,832 | A | 2/1994 | Toso et al. |
| 5,282,867 | A | 2/1994 | Mikhail |
| 5,282,868 | A | 2/1994 | Bahler |
| 5,285,040 | A | 2/1994 | Brandberg et al. |
| 5,290,217 | A | 3/1994 | Campos |
| 5,290,243 | A | 3/1994 | Chodorow et al. |
| 5,306,301 | A | 4/1994 | Graf et al. |
| 5,312,410 | A | 5/1994 | Miller et al. |
| 5,312,422 | A | 5/1994 | Trott |
| 5,312,438 | A | 5/1994 | Johnson |
| 5,314,429 | A | 5/1994 | Goble |
| 5,318,566 | A | 6/1994 | Miller |
| 5,318,575 | A | 6/1994 | Chesterfield et al. |
| 5,318,577 | A | 6/1994 | Li |
| 5,318,578 | A | 6/1994 | Hasson |
| 5,320,115 | A | 6/1994 | Kenna |
| 5,320,626 | A | 6/1994 | Schmieding |
| 5,320,633 | A | 6/1994 | Allen et al. |
| 5,324,308 | A | 6/1994 | Pierce |
| 5,330,489 | A | 7/1994 | Green et al. |
| 5,333,625 | A | 8/1994 | Klein |
| 5,334,204 | A | 8/1994 | Clewett et al. |
| 5,336,229 | A | 8/1994 | Noda |
| 5,336,231 | A | 8/1994 | Adair |
| 5,336,240 | A | 8/1994 | Metzler et al. |
| 5,339,870 | A | 8/1994 | Green et al. |
| 5,342,369 | A | 8/1994 | Harryman, II |
| 5,346,462 | A | 9/1994 | Barber |
| 5,350,380 | A | 9/1994 | Goble et al. |
| RE34,762 | E | 10/1994 | Goble et al. |
| 5,354,292 | A | 10/1994 | Braeuer et al. |
| 5,354,298 | A | 10/1994 | Lee et al. |
| 5,354,299 | A | 10/1994 | Coleman |
| 5,356,412 | A | 10/1994 | Golds et al. |
| 5,356,413 | A | 10/1994 | Martins et al. |
| 5,356,417 | A | 10/1994 | Golds |
| 5,358,511 | A | 10/1994 | Gatturna et al. |
| 5,360,431 | A | 11/1994 | Puno et al. |
| 5,362,294 | A | 11/1994 | Seitzinger |
| 5,362,911 | A | 11/1994 | Cevasco et al. |
| 5,364,400 | A | 11/1994 | Rego, Jr. et al. |
| 5,366,461 | A | 11/1994 | Blasnik |
| 5,368,599 | A | 11/1994 | Hirsch et al. |
| 5,370,646 | A | 12/1994 | Reese et al. |
| 5,370,661 | A | 12/1994 | Branch |
| 5,370,662 | A | 12/1994 | Stone et al. |
| 5,372,146 | A | 12/1994 | Branch |
| 5,372,604 | A | 12/1994 | Trott |
| 5,372,821 | A | 12/1994 | Badylak et al. |
| 5,374,268 | A | 12/1994 | Sander |
| 5,374,269 | A | 12/1994 | Rosenberg |
| 5,379,492 | A | 1/1995 | Glesser |
| 5,383,878 | A | 1/1995 | Roger et al. |
| 5,383,904 | A | 1/1995 | Totakura et al. |
| 5,385,567 | A | 1/1995 | Goble |
| 5,391,171 | A | 2/1995 | Schmieding |
| 5,391,176 | A | 2/1995 | de la Torre |
| 5,391,182 | A | 2/1995 | Chin |
| 5,393,302 | A | 2/1995 | Clark et al. |
| RE34,871 | E | 3/1995 | McGuire et al. |
| 5,395,374 | A | 3/1995 | Miller et al. |
| 5,397,356 | A | 3/1995 | Goble et al. |
| 5,403,328 | A | 4/1995 | Shallman |
| 5,403,329 | A | 4/1995 | Hinchcliffe |
| 5,403,348 | A | 4/1995 | Bonutti |
| 5,405,359 | A | 4/1995 | Pierce |
| 5,411,550 | A | 5/1995 | Herweck et al. |
| 5,415,658 | A | 5/1995 | Kilpela et al. |
| 5,417,690 | A | 5/1995 | Sennett et al. |
| 5,417,691 | A | 5/1995 | Hayhurst |
| 5,417,698 | A | 5/1995 | Green et al. |
| 5,417,712 | A | 5/1995 | Whittaker et al. |
| 5,423,819 | A | 6/1995 | Small et al. |
| 5,423,821 | A | 6/1995 | Pasque |
| 5,423,823 | A | 6/1995 | Schmieding |
| 5,423,824 | A | 6/1995 | Akerfeldt et al. |
| 5,423,860 | A | 6/1995 | Lizardi et al. |
| 5,425,733 | A | 6/1995 | Schmieding |
| 5,425,766 | A | 6/1995 | Bowald et al. |
| 5,433,751 | A | 7/1995 | Christel et al. |
| 5,437,680 | A | 8/1995 | Yoon |
| 5,437,685 | A | 8/1995 | Blasnik |
| 5,439,684 | A | 8/1995 | Prewett et al. |
| 5,441,508 | A | 8/1995 | Gazielly et al. |
| 5,443,468 | A | 8/1995 | Johnson |

(56) References Cited

U.S. PATENT DOCUMENTS

| | | | |
|---|---|---|---|
| 5,443,482 | A | 8/1995 | Stone et al. |
| 5,443,483 | A | 8/1995 | Kirsch et al. |
| 5,443,509 | A | 8/1995 | Boucher et al. |
| 5,445,833 | A | 8/1995 | Badylak et al. |
| 5,447,512 | A | 9/1995 | Wilson et al. |
| 5,449,361 | A | 9/1995 | Preissman |
| 5,451,203 | A | 9/1995 | Lamb |
| 5,454,811 | A | 10/1995 | Huebner |
| 5,454,821 | A | 10/1995 | Harm et al. |
| 5,456,685 | A | 10/1995 | Huebner |
| 5,456,721 | A | 10/1995 | Legrand |
| 5,456,722 | A | 10/1995 | McLeod et al. |
| 5,458,601 | A | 10/1995 | Young, Jr. et al. |
| 5,458,604 | A | 10/1995 | Schmieding |
| 5,462,542 | A | 10/1995 | Alesi, Jr. |
| 5,462,560 | A | 10/1995 | Stevens |
| 5,464,426 | A | 11/1995 | Bonutti |
| 5,464,427 | A | 11/1995 | Curtis et al. |
| 5,464,440 | A | 11/1995 | Johansson et al. |
| 5,466,237 | A | 11/1995 | Byrd, III et al. |
| 5,467,786 | A | 11/1995 | Allen et al. |
| 5,470,334 | A | 11/1995 | Ross et al. |
| 5,470,337 | A | 11/1995 | Moss |
| 5,470,338 | A | 11/1995 | Whitfield et al. |
| 5,472,452 | A | 12/1995 | Trott |
| 5,474,565 | A | 12/1995 | Trott |
| 5,474,568 | A | 12/1995 | Scott |
| 5,474,572 | A | 12/1995 | Hayhurst |
| 5,476,465 | A | 12/1995 | Preissman |
| 5,478,344 | A | 12/1995 | Stone et al. |
| 5,478,345 | A | 12/1995 | Stone et al. |
| 5,480,403 | A | 1/1996 | Lee et al. |
| 5,480,406 | A | 1/1996 | Nolan et al. |
| 5,484,442 | A | 1/1996 | Melker et al. |
| 5,486,197 | A | 1/1996 | Le et al. |
| 5,486,359 | A | 1/1996 | Caplan et al. |
| 5,489,210 | A | 2/1996 | Hanosh |
| 5,490,750 | A | 2/1996 | Gundy |
| 5,495,974 | A | 3/1996 | Deschenes et al. |
| 5,496,290 | A | 3/1996 | Ackerman |
| 5,496,331 | A | 3/1996 | Xu et al. |
| 5,496,348 | A | 3/1996 | Bonutti |
| 5,498,302 | A | 3/1996 | Davidson |
| 5,500,000 | A | 3/1996 | Feagin et al. |
| 5,505,735 | A | 4/1996 | Li |
| 5,505,736 | A | 4/1996 | Reimels et al. |
| 5,507,754 | A | 4/1996 | Green et al. |
| 5,520,691 | A | 5/1996 | Branch |
| 5,520,694 | A | 5/1996 | Dance et al. |
| 5,520,700 | A | 5/1996 | Beyar et al. |
| 5,520,702 | A | 5/1996 | Sauer et al. |
| 5,522,817 | A | 6/1996 | Sander et al. |
| 5,522,820 | A | 6/1996 | Caspari et al. |
| 5,522,843 | A | 6/1996 | Zang |
| 5,522,844 | A | 6/1996 | Johnson |
| 5,522,845 | A | 6/1996 | Wenstrom, Jr. |
| 5,522,846 | A | 6/1996 | Bonutti |
| 5,524,946 | A | 6/1996 | Thompson |
| 5,527,321 | A | 6/1996 | Hinchliffe |
| 5,527,342 | A | 6/1996 | Pietrzak et al. |
| 5,527,343 | A | 6/1996 | Bonutti |
| 5,531,759 | A | 7/1996 | Kensey et al. |
| 5,534,012 | A | 7/1996 | Bonutti |
| 5,534,033 | A | 7/1996 | Simpson |
| 5,536,270 | A | 7/1996 | Songer et al. |
| 5,540,698 | A | 7/1996 | Preissman |
| 5,540,703 | A | 7/1996 | Barker, Jr. et al. |
| 5,540,718 | A | 7/1996 | Bartlett |
| 5,545,168 | A | 8/1996 | Burke |
| 5,545,178 | A | 8/1996 | Kensey et al. |
| 5,545,180 | A | 8/1996 | Le et al. |
| 5,545,228 | A | 8/1996 | Kambin |
| 5,549,613 | A | 8/1996 | Goble et al. |
| 5,549,617 | A | 8/1996 | Green et al. |
| 5,549,619 | A | 8/1996 | Peters et al. |
| 5,549,630 | A | 8/1996 | Bonutti |
| 5,549,631 | A | 8/1996 | Bonutti |
| 5,562,664 | A | 10/1996 | Durlacher et al. |
| 5,562,668 | A | 10/1996 | Johnson |
| 5,562,669 | A | 10/1996 | McGuire |
| 5,562,683 | A | 10/1996 | Chan |
| 5,562,685 | A | 10/1996 | Mollenauer et al. |
| 5,562,686 | A | 10/1996 | Sauer et al. |
| 5,569,269 | A | 10/1996 | Hart et al. |
| 5,569,305 | A | 10/1996 | Bonutti |
| 5,569,306 | A | 10/1996 | Thal |
| 5,570,706 | A | 11/1996 | Howell |
| 5,571,090 | A | 11/1996 | Sherts |
| 5,571,104 | A | 11/1996 | Li |
| 5,571,139 | A | 11/1996 | Jenkins, Jr. |
| 5,572,655 | A | 11/1996 | Tuljapurkar et al. |
| 5,573,286 | A | 11/1996 | Rogozinski |
| 5,573,542 | A | 11/1996 | Stevens |
| 5,573,547 | A | 11/1996 | LeVeen et al. |
| 5,573,548 | A | 11/1996 | Nazre et al. |
| 5,577,299 | A | 11/1996 | Thompson et al. |
| 5,578,057 | A | 11/1996 | Wenstrom, Jr. |
| 5,584,695 | A | 12/1996 | Lal Sachdeva et al. |
| 5,584,835 | A | 12/1996 | Greenfield |
| 5,584,836 | A | 12/1996 | Ballintyn et al. |
| 5,584,862 | A | 12/1996 | Bonutti |
| 5,586,986 | A | 12/1996 | Hinchliffe |
| 5,588,575 | A | 12/1996 | Davignon |
| 5,591,180 | A | 1/1997 | Hinchliffe |
| 5,591,181 | A | 1/1997 | Stone et al. |
| 5,591,207 | A | 1/1997 | Coleman |
| 5,593,407 | A | 1/1997 | Reis et al. |
| 5,593,425 | A | 1/1997 | Bonutti et al. |
| 5,601,557 | A | 2/1997 | Hayhurst |
| 5,601,559 | A | 2/1997 | Melker et al. |
| 5,601,571 | A | 2/1997 | Moss |
| 5,603,716 | A | 2/1997 | Morgan et al. |
| 5,607,429 | A | 3/1997 | Hayano et al. |
| 5,607,430 | A | 3/1997 | Bailey |
| 5,613,971 | A | 3/1997 | Lower et al. |
| 5,618,290 | A | 4/1997 | Toy et al. |
| 5,626,611 | A | 5/1997 | Liu et al. |
| 5,626,614 | A | 5/1997 | Hart |
| 5,628,756 | A | 5/1997 | Barker, Jr. et al. |
| 5,628,766 | A | 5/1997 | Johnson |
| 5,630,824 | A | 5/1997 | Hart |
| 5,632,745 | A | 5/1997 | Schwartz |
| 5,632,748 | A | 5/1997 | Beck, Jr. et al. |
| 5,641,256 | A | 6/1997 | Gundy |
| 5,643,266 | A | 7/1997 | Li |
| 5,643,269 | A | 7/1997 | Harle et al. |
| 5,643,273 | A | 7/1997 | Clark |
| 5,643,295 | A | 7/1997 | Yoon |
| 5,643,319 | A | 7/1997 | Green et al. |
| 5,643,320 | A | 7/1997 | Lower et al. |
| 5,643,321 | A | 7/1997 | McDevitt |
| 5,645,546 | A | 7/1997 | Fard |
| 5,645,547 | A | 7/1997 | Coleman |
| 5,645,568 | A | 7/1997 | Chervitz et al. |
| 5,645,588 | A | 7/1997 | Graf et al. |
| 5,647,874 | A | 7/1997 | Hayhurst |
| 5,649,959 | A | 7/1997 | Hannam et al. |
| 5,649,960 | A | 7/1997 | Pavletic |
| 5,649,963 | A | 7/1997 | McDevitt |
| 5,658,289 | A | 8/1997 | Boucher et al. |
| 5,658,299 | A | 8/1997 | Hart |
| 5,658,313 | A | 8/1997 | Thal |
| 5,662,658 | A | 9/1997 | Wenstrom, Jr. |
| 5,662,663 | A | 9/1997 | Shallman |
| 5,662,677 | A | 9/1997 | Wimmer |
| 5,662,681 | A | 9/1997 | Nash et al. |
| 5,665,112 | A | 9/1997 | Thal |
| 5,667,513 | A | 9/1997 | Torrie et al. |
| 5,671,695 | A | 9/1997 | Schroeder |
| 5,674,224 | A | 10/1997 | Howell et al. |
| 5,679,723 | A | 10/1997 | Cooper et al. |
| 5,681,334 | A | 10/1997 | Evans et al. |
| 5,681,352 | A | 10/1997 | Clancy, III et al. |
| 5,683,404 | A | 11/1997 | Johnson |

(56) References Cited

U.S. PATENT DOCUMENTS 5,683,419 A 11/1997 Thal
5,688,284 A 11/1997 Chervitz et al.
5,688,285 A 11/1997 Yamada et al.
5,690,655 A 11/1997 Hart et al.
5,690,676 A 11/1997 DiPoto et al.
5,690,678 A 11/1997 Johnson
5,693,046 A 12/1997 Songer et al.
5,695,497 A 12/1997 Stahelin et al.
5,697,929 A 12/1997 Mellinger
5,699,657 A 12/1997 Paulson
5,702,397 A 12/1997 Goble et al.
5,702,422 A 12/1997 Stone
5,702,462 A 12/1997 Oberlander
5,707,373 A 1/1998 Sevrain et al.
5,709,708 A 1/1998 Thal
5,711,969 A 1/1998 Patel et al.
5,713,005 A 1/1998 Proebsting
5,713,897 A 2/1998 Goble et al.
5,713,904 A 2/1998 Errico et al.
5,713,905 A 2/1998 Goble et al.
5,713,921 A 2/1998 Bonutti
5,715,578 A 2/1998 Knudson
5,716,359 A 2/1998 Ojima et al.
5,716,397 A 2/1998 Myers
5,716,616 A 2/1998 Prockop et al.
5,718,717 A 2/1998 Bonutti
5,720,747 A 2/1998 Burke
5,720,765 A 2/1998 Thal
5,720,766 A 2/1998 Zang et al.
5,722,976 A 3/1998 Brown
5,723,331 A 3/1998 Tubo et al.
5,725,529 A 3/1998 Nicholson et al.
5,725,549 A 3/1998 Lam
5,725,556 A 3/1998 Moser et al.
5,725,557 A 3/1998 Gatturna et al.
5,725,581 A 3/1998 Brånemark
5,725,582 A 3/1998 Bevan et al.
5,726,722 A 3/1998 Uehara et al.
5,728,107 A 3/1998 Zlock et al.
5,728,109 A 3/1998 Schulze et al.
5,728,136 A 3/1998 Thal
5,733,293 A 3/1998 Scirica et al.
5,733,306 A 3/1998 Bonutti
5,733,307 A 3/1998 Dinsdale
5,735,875 A 4/1998 Bonutti et al.
5,741,259 A 4/1998 Chan
5,741,260 A 4/1998 Songer et al.
5,741,281 A 4/1998 Martin et al.
5,743,912 A 4/1998 Lahille et al.
5,746,751 A 5/1998 Sherts
5,746,752 A 5/1998 Burkhart
5,746,754 A 5/1998 Chan
5,749,898 A 5/1998 Schulze et al.
5,755,729 A 5/1998 de la Torre et al.
5,755,791 A 5/1998 Whitson et al.
5,766,176 A 6/1998 Duncan
5,766,218 A 6/1998 Arnott
5,766,250 A 6/1998 Chervitz et al.
5,769,894 A 6/1998 Ferragamo
5,769,899 A 6/1998 Schwartz et al.
5,772,673 A 6/1998 Cuny et al.
5,776,196 A 7/1998 Matsuzaki et al.
5,776,200 A 7/1998 Johnson et al.
5,782,845 A 7/1998 Shewchuk
5,782,862 A 7/1998 Bonutti
5,782,864 A 7/1998 Lizardi
5,782,866 A 7/1998 Wenstrom, Jr.
5,782,925 A 7/1998 Collazo et al.
5,785,714 A 7/1998 Morgan et al.
5,786,217 A 7/1998 Tubo et al.
5,792,142 A 8/1998 Galitzer
5,792,149 A 8/1998 Sherts et al.
5,796,127 A 8/1998 Hayafuji et al.
5,797,913 A 8/1998 Dambreville et al.
5,797,915 A 8/1998 Pierson, III et al.
5,797,916 A 8/1998 McDowell
5,797,928 A 8/1998 Kogasaka
5,800,407 A 9/1998 Eldor et al.
5,800,543 A 9/1998 McLeod et al.
5,810,824 A 9/1998 Chan
5,810,848 A 9/1998 Hayhurst
5,811,094 A 9/1998 Caplan et al.
5,814,056 A 9/1998 Prosst et al.
5,814,069 A 9/1998 Schulze et al.
5,814,070 A 9/1998 Borzone et al.
5,814,071 A 9/1998 Mcdevitt et al.
5,814,072 A 9/1998 Bonutti
5,814,073 A 9/1998 Bonutti
5,817,095 A 10/1998 Smith
5,823,980 A 10/1998 Kopfer
5,824,011 A 10/1998 Stone et al.
5,824,066 A 10/1998 Gross
5,830,234 A 11/1998 Wojciechowicz et al.
5,836,955 A 11/1998 Buelna et al.
5,843,084 A 12/1998 Hart et al.
5,845,645 A 12/1998 Bonutti
5,846,254 A 12/1998 Schulze et al.
5,848,983 A 12/1998 Basaj et al.
5,849,012 A 12/1998 Abboudi
5,860,947 A 1/1999 Stamler
5,860,973 A 1/1999 Michelson
5,860,978 A 1/1999 McDevitt et al.
5,868,740 A 2/1999 LeVeen et al.
5,868,748 A 2/1999 Burke
5,868,789 A 2/1999 Huebner
5,871,456 A 2/1999 Armstrong et al.
5,871,484 A 2/1999 Spievack et al.
5,871,486 A 2/1999 Huebner et al.
5,871,490 A 2/1999 Schulze et al.
5,885,294 A 3/1999 Pedlick et al.
5,891,168 A 4/1999 Thal
5,893,592 A 4/1999 Schulze et al.
5,895,395 A 4/1999 Yeung
5,897,564 A 4/1999 Schulze et al.
5,897,574 A 4/1999 Bonutti
5,899,902 A 5/1999 Brown et al.
5,899,938 A 5/1999 Sklar et al.
5,906,934 A 5/1999 Grande et al.
5,908,421 A 6/1999 Beger et al.
5,908,436 A 6/1999 Cuschieri et al.
5,910,148 A 6/1999 Reimels et al.
5,911,721 A 6/1999 Nicholson et al.
5,916,557 A 6/1999 Berlowitz-tarrant et al.
5,918,604 A 7/1999 Whelan
5,921,986 A 7/1999 Bonutti
5,925,008 A 7/1999 Douglas
5,928,231 A 7/1999 Klein et al.
5,928,267 A 7/1999 Bonutti et al.
5,928,286 A 7/1999 Ashby et al.
RE36,289 E 8/1999 Le et al.
5,931,838 A 8/1999 Vito
5,931,844 A 8/1999 Thompson et al.
5,931,869 A 8/1999 Boucher et al.
5,935,119 A 8/1999 Guy et al.
5,935,129 A 8/1999 McDevitt et al.
5,935,133 A 8/1999 Wagner et al.
5,935,134 A 8/1999 Pedlick et al.
5,935,149 A 8/1999 Ek
5,938,668 A 8/1999 Scirica et al.
5,941,439 A 8/1999 Kammerer et al.
5,941,900 A 8/1999 Bonutti
5,944,739 A 8/1999 Zlock et al.
5,946,783 A 9/1999 Plociennik et al.
5,947,915 A 9/1999 Thibodo, Jr.
5,947,982 A 9/1999 Duran
5,947,999 A 9/1999 Groiso
5,948,002 A 9/1999 Bonutti
5,951,559 A 9/1999 Burkhart
5,951,560 A 9/1999 Simon et al.
5,954,747 A 9/1999 Clark
5,957,953 A 9/1999 DiPoto et al.
5,961,520 A 10/1999 Beck, Jr. et al.
5,961,521 A 10/1999 Roger et al.
5,961,524 A 10/1999 Crombie

(56) References Cited

U.S. PATENT DOCUMENTS 5,963,869 A 10/1999 Fehnel
5,964,764 A 10/1999 West, Jr. et al.
5,964,767 A 10/1999 Tapia et al.
5,964,769 A 10/1999 Wagner et al.
5,964,783 A 10/1999 Grafton et al.
5,968,045 A 10/1999 Frazier
5,968,047 A 10/1999 Reed
5,968,077 A 10/1999 Wojciechowicz et al.
5,970,697 A 10/1999 Jacobs et al.
5,972,006 A 10/1999 Sciaino, Jr.
5,976,125 A 11/1999 Graham
5,976,127 A 11/1999 Lax
5,980,473 A 11/1999 Korakianitis et al.
5,980,524 A 11/1999 Justin et al.
5,980,539 A 11/1999 Kontos
5,980,548 A 11/1999 Evans et al.
5,980,558 A 11/1999 Wiley
5,980,559 A 11/1999 Bonutti
5,989,252 A 11/1999 Fumex
5,989,256 A 11/1999 Kuslich et al.
5,989,282 A 11/1999 Bonutti
5,989,294 A 11/1999 Marlow
5,993,452 A 11/1999 Vandewalle
5,993,476 A 11/1999 Groiso
5,997,542 A 12/1999 Burke
5,997,552 A 12/1999 Person et al.
5,997,575 A 12/1999 Whitson et al.
6,001,100 A 12/1999 Sherman et al.
6,001,106 A 12/1999 Ryan et al.
6,004,351 A 12/1999 Tomita et al.
6,004,352 A 12/1999 Buni
6,007,538 A 12/1999 Levin
6,007,567 A 12/1999 Bonutti
6,010,525 A 1/2000 Bonutti et al.
6,013,103 A 1/2000 Kaufman et al.
6,016,727 A 1/2000 Morgan
6,019,767 A 2/2000 Howell
6,022,352 A 2/2000 Vandewalle
6,022,373 A 2/2000 Li
6,023,661 A 2/2000 Sottery
6,024,758 A 2/2000 Thal
6,027,523 A 2/2000 Schmieding
6,030,410 A 2/2000 Zurbrugg
6,033,429 A 3/2000 Magovern
6,033,430 A 3/2000 Bonutti
6,036,695 A 3/2000 Smith
6,039,753 A 3/2000 Meislin
6,041,485 A 3/2000 Pedlick et al.
6,042,601 A 3/2000 Smith
6,042,609 A 3/2000 Giordano et al.
6,045,551 A 4/2000 Bonutti
6,045,571 A 4/2000 Hill et al.
6,045,572 A 4/2000 Johnson et al.
6,045,573 A 4/2000 Wenstrom, Jr. et al.
6,045,574 A 4/2000 Thal
6,047,826 A 4/2000 Kalinski et al.
6,048,343 A 4/2000 Mathis et al.
6,051,006 A 4/2000 Shluzas et al.
6,051,007 A 4/2000 Hogendijk et al.
6,053,916 A 4/2000 Moore
6,053,921 A 4/2000 Wagner et al.
6,056,752 A 5/2000 Roger
6,056,772 A 5/2000 Bonutti
6,056,773 A 5/2000 Bonutti
6,059,817 A 5/2000 Bonutti et al.
6,059,818 A 5/2000 Johnson et al.
6,062,344 A 5/2000 Okabe et al.
6,066,173 A 5/2000 McKernan et al.
6,068,648 A 5/2000 Cole et al.
6,071,305 A 6/2000 Brown et al.
6,074,403 A 6/2000 Nord
6,077,277 A 6/2000 Mollenauer et al.
6,077,292 A 6/2000 Bonutti
6,080,185 A 6/2000 Johnson et al.
6,086,591 A 7/2000 Bojarski
6,086,592 A 7/2000 Rosenberg et al.
6,086,608 A 7/2000 Ek et al.
6,093,200 A 7/2000 Liu et al.
6,096,060 A 8/2000 Fitts et al.
6,099,527 A 8/2000 Hochschuler et al.
6,099,530 A 8/2000 Simonian et al.
6,099,568 A 8/2000 Simonian et al.
6,102,934 A 8/2000 Li
6,106,545 A 8/2000 Egan
6,110,128 A 8/2000 Andelin et al.
6,110,207 A 8/2000 Eichhorn et al.
6,113,604 A 9/2000 Whittaker et al.
6,117,160 A 9/2000 Bonutti
6,117,162 A 9/2000 Schmieding et al.
6,123,710 A 9/2000 Pinczewski et al.
6,127,596 A 10/2000 Brown et al.
6,132,433 A 10/2000 Whelan
6,132,437 A 10/2000 Omurtag et al.
6,136,010 A 10/2000 Modesitt et al.
6,139,565 A 10/2000 Stone et al.
RE36,974 E 11/2000 Bonutti
6,143,017 A 11/2000 Thal
6,146,406 A 11/2000 Shluzas et al.
6,146,408 A 11/2000 Bartlett
6,149,653 A 11/2000 Deslauriers
6,149,669 A 11/2000 Li
6,150,163 A 11/2000 McPherson et al.
6,152,928 A 11/2000 Wenstrom, Jr.
6,152,934 A 11/2000 Harper et al.
6,152,936 A 11/2000 Christy et al.
6,152,949 A 11/2000 Bonutti
6,156,039 A 12/2000 Thal
6,156,056 A 12/2000 Kearns et al.
6,159,234 A 12/2000 Bonutti et al.
6,165,203 A 12/2000 Krebs
6,168,598 B1 1/2001 Martello
6,168,628 B1 1/2001 Huebner
6,171,310 B1 1/2001 Giordano et al.
6,179,840 B1 1/2001 Bowman
6,183,461 B1 2/2001 Matsuura et al.
6,183,737 B1 2/2001 Zaleske et al.
6,187,025 B1 2/2001 Machek
6,190,348 B1 2/2001 Tiemann et al.
6,190,401 B1 2/2001 Green et al.
6,190,411 B1 2/2001 Lo et al.
6,193,754 B1 2/2001 Seedhom
6,200,318 B1 3/2001 Har-Shai et al.
6,200,329 B1 3/2001 Fung et al.
6,200,330 B1 3/2001 Benderev et al.
6,200,606 B1 3/2001 Peterson et al.
6,200,685 B1 3/2001 Davidson
6,203,556 B1 3/2001 Evans et al.
6,203,563 B1 3/2001 Fernandez
6,203,565 B1 3/2001 Bonutti et al.
6,203,572 B1 3/2001 Johnson et al.
6,203,576 B1 3/2001 Afriat et al.
6,206,883 B1 3/2001 Tunc
6,210,376 B1 4/2001 Grayson
6,210,381 B1 4/2001 Morse
6,214,007 B1 4/2001 Anderson
6,214,012 B1 4/2001 Karpman et al.
6,217,580 B1 4/2001 Levin
6,221,107 B1 4/2001 Steiner et al.
6,228,096 B1 5/2001 Marchand
6,231,592 B1 5/2001 Bonutti et al.
6,234,980 B1 5/2001 Bell
6,235,057 B1 5/2001 Roger et al.
6,235,058 B1 5/2001 Huene
6,238,395 B1 5/2001 Bonutti
6,241,734 B1 6/2001 Scribner et al.
6,241,747 B1 6/2001 Ruff
6,241,771 B1 6/2001 Gresser et al.
6,245,081 B1 6/2001 Bowman et al.
6,254,604 B1 7/2001 Howell
6,258,091 B1 7/2001 Sevrain et al.
6,267,766 B1 7/2001 Burkhart
6,269,716 B1 8/2001 Amis
6,270,518 B1 8/2001 Pedlick et al.
6,273,890 B1 8/2001 Frazier

(56) References Cited

U.S. PATENT DOCUMENTS

| | | | |
|---|---|---|---|
| 6,280,474 | B1 | 8/2001 | Cassidy et al. |
| 6,283,973 | B1 | 9/2001 | Hubbard et al. |
| 6,283,996 | B1 | 9/2001 | Chervitz et al. |
| 6,287,307 | B1 | 9/2001 | Abboudi |
| 6,287,325 | B1 | 9/2001 | Bonutti |
| 6,293,929 | B1 | 9/2001 | Smith et al. |
| 6,293,961 | B2 | 9/2001 | Schwartz et al. |
| 6,296,659 | B1 | 10/2001 | Foerster |
| 6,299,615 | B1 | 10/2001 | Huebner |
| 6,302,888 | B1 | 10/2001 | Mellinger et al. |
| 6,302,899 | B1 | 10/2001 | Johnson et al. |
| 6,302,915 | B1 | 10/2001 | Cooney, III et al. |
| 6,303,158 | B1 | 10/2001 | Odgaard et al. |
| 6,306,156 | B1 | 10/2001 | Clark |
| 6,306,158 | B1 | 10/2001 | Bartlett |
| 6,306,159 | B1 | 10/2001 | Schwartz et al. |
| 6,309,124 | B1 | 10/2001 | Gueret |
| 6,309,405 | B1 | 10/2001 | Bonutti |
| 6,312,448 | B1 | 11/2001 | Bonutti |
| 6,315,788 | B1 | 11/2001 | Roby |
| 6,319,224 | B1 | 11/2001 | Stout et al. |
| 6,319,271 | B1 | 11/2001 | Schwartz et al. |
| 6,328,758 | B1 | 12/2001 | Tornier et al. |
| 6,334,064 | B1 | 12/2001 | Fiddian-green |
| 6,342,060 | B1 | 1/2002 | Adams |
| 6,343,531 | B2 | 2/2002 | Amis |
| 6,355,066 | B1 | 3/2002 | Kim |
| 6,358,270 | B1 | 3/2002 | Lemer |
| 6,364,897 | B1 | 4/2002 | Bonutti |
| 6,368,322 | B1 | 4/2002 | Luks et al. |
| 6,368,326 | B1 | 4/2002 | Dakin et al. |
| 6,368,343 | B1 | 4/2002 | Bonutti et al. |
| 6,371,124 | B1 | 4/2002 | Whelan |
| 6,379,361 | B1 | 4/2002 | Beck, Jr. et al. |
| 6,383,190 | B1 | 5/2002 | Preissman |
| 6,383,199 | B2 | 5/2002 | Carter et al. |
| 6,387,111 | B1 | 5/2002 | Barber |
| 6,387,113 | B1 | 5/2002 | Hawkins et al. |
| 6,387,129 | B2 | 5/2002 | Rieser et al. |
| 6,391,030 | B1 | 5/2002 | Wagner et al. |
| 6,398,785 | B2 | 6/2002 | Carchidi et al. |
| 6,406,456 | B1 | 6/2002 | Slate et al. |
| 6,406,479 | B1 | 6/2002 | Justin et al. |
| 6,409,743 | B1 | 6/2002 | Fenton, Jr. |
| 6,413,260 | B1 | 7/2002 | Berrevoets et al. |
| 6,423,073 | B2 | 7/2002 | Bowman |
| 6,423,088 | B1 | 7/2002 | Fenton, Jr. |
| 6,425,924 | B1 | 7/2002 | Rousseau |
| 6,428,562 | B2 | 8/2002 | Bonutti |
| 6,432,123 | B2 | 8/2002 | Schwartz et al. |
| 6,436,123 | B1 | 8/2002 | Magovern |
| 6,436,124 | B1 | 8/2002 | Anderson et al. |
| 6,440,134 | B1 | 8/2002 | Zaccherotti et al. |
| 6,440,136 | B1 | 8/2002 | Gambale et al. |
| 6,447,516 | B1 | 9/2002 | Bonutti |
| 6,451,030 | B2 | 9/2002 | Li et al. |
| 6,454,768 | B1 | 9/2002 | Jackson |
| 6,458,134 | B1 | 10/2002 | Songer et al. |
| 6,458,161 | B1 | 10/2002 | Gibbs et al. |
| 6,461,373 | B2 | 10/2002 | Wyman et al. |
| 6,464,690 | B1 | 10/2002 | Castaneda et al. |
| 6,464,713 | B2 | 10/2002 | Bonutti |
| 6,468,293 | B2 | 10/2002 | Bonutti et al. |
| 6,471,707 | B1 | 10/2002 | Miller et al. |
| 6,475,230 | B1 | 11/2002 | Bonutti et al. |
| 6,478,753 | B2 | 11/2002 | Reay-Young |
| 6,482,210 | B1 | 11/2002 | Skiba et al. |
| 6,485,504 | B1 | 11/2002 | Johnson et al. |
| 6,491,714 | B1 | 12/2002 | Bennett |
| 6,497,901 | B1 | 12/2002 | Royer |
| 6,500,184 | B1 | 12/2002 | Chan et al. |
| 6,500,195 | B2 | 12/2002 | Bonutti |
| RE37,963 | E | 1/2003 | Thal |
| 6,503,267 | B2 | 1/2003 | Bonutti et al. |
| 6,506,190 | B1 | 1/2003 | Walshe |
| 6,508,820 | B2 | 1/2003 | Bales |
| 6,508,821 | B1 | 1/2003 | Schwartz et al. |
| 6,508,830 | B2 | 1/2003 | Steiner |
| 6,511,498 | B1 | 1/2003 | Fumex |
| 6,511,499 | B2 | 1/2003 | Schmieding et al. |
| 6,514,274 | B1 | 2/2003 | Boucher et al. |
| 6,517,542 | B1 | 2/2003 | Papay et al. |
| 6,517,552 | B1 | 2/2003 | Nord et al. |
| 6,517,564 | B1 | 2/2003 | Grafton et al. |
| 6,517,578 | B2 | 2/2003 | Hein |
| 6,517,579 | B1 | 2/2003 | Paulos et al. |
| 6,520,964 | B2 | 2/2003 | Tallarida et al. |
| 6,520,980 | B1 | 2/2003 | Foerster |
| 6,524,317 | B1 | 2/2003 | Ritchart et al. |
| 6,527,777 | B2 | 3/2003 | Justin |
| 6,527,794 | B1 | 3/2003 | McDevitt et al. |
| 6,527,795 | B1 | 3/2003 | Lizardi |
| 6,533,795 | B1 | 3/2003 | Tran et al. |
| 6,533,802 | B2 | 3/2003 | Bojarski et al. |
| 6,537,319 | B2 | 3/2003 | Whelan |
| 6,540,750 | B2 | 4/2003 | Burkhart |
| 6,540,769 | B1 | 4/2003 | Miller, III |
| 6,540,770 | B1 | 4/2003 | Tornier et al. |
| 6,540,783 | B1 | 4/2003 | Whittaker et al. |
| 6,543,094 | B2 | 4/2003 | D'Addario |
| 6,544,281 | B2 | 4/2003 | ElAttrache et al. |
| 6,547,564 | B1 | 4/2003 | Hansson et al. |
| 6,547,778 | B1 | 4/2003 | Sklar et al. |
| 6,547,800 | B2 | 4/2003 | Foerster et al. |
| 6,551,330 | B1 | 4/2003 | Bain et al. |
| 6,551,343 | B1 | 4/2003 | Tormala et al. |
| 6,551,353 | B1 | 4/2003 | Baker et al. |
| 6,553,802 | B1 | 4/2003 | Jacob et al. |
| 6,554,830 | B1 | 4/2003 | Chappius |
| 6,554,852 | B1 | 4/2003 | Oberlander |
| 6,554,862 | B2 | 4/2003 | Hays et al. |
| 6,558,389 | B2 | 5/2003 | Clark et al. |
| 6,562,071 | B2 | 5/2003 | Jarvinen et al. |
| 6,565,572 | B2 | 5/2003 | Chappius |
| 6,565,573 | B1 | 5/2003 | Ferrante et al. |
| 6,569,167 | B1 | 5/2003 | Bobechko et al. |
| 6,569,186 | B1 | 5/2003 | Winters et al. |
| 6,569,187 | B1 | 5/2003 | Bonutti et al. |
| 6,572,635 | B1 | 6/2003 | Bonutti |
| 6,572,655 | B1 | 6/2003 | Johnson |
| 6,575,925 | B1 | 6/2003 | Noble |
| 6,579,295 | B1 | 6/2003 | Supinski |
| 6,582,453 | B1 | 6/2003 | Tran et al. |
| 6,585,730 | B1 | 7/2003 | Foerster |
| 6,585,740 | B2 | 7/2003 | Schlapfer et al. |
| 6,585,750 | B2 | 7/2003 | Bonutti et al. |
| 6,589,245 | B1 | 7/2003 | Weiler et al. |
| 6,589,246 | B1 | 7/2003 | Hack et al. |
| 6,592,609 | B1 | 7/2003 | Bonutti |
| 6,592,622 | B1 | 7/2003 | Ferguson |
| 6,595,911 | B2 | 7/2003 | LoVuolo |
| 6,599,289 | B1 | 7/2003 | Bojarski et al. |
| 6,599,319 | B2 | 7/2003 | Knudsen et al. |
| 6,605,096 | B1 | 8/2003 | Ritchart |
| 6,607,548 | B2 | 8/2003 | Pohjonen et al. |
| 6,610,079 | B1 | 8/2003 | Li et al. |
| 6,613,018 | B2 | 9/2003 | Bagga et al. |
| 6,616,694 | B1 | 9/2003 | Hart |
| 6,620,166 | B1 | 9/2003 | Wenstrom, Jr. et al. |
| 6,620,185 | B1 | 9/2003 | Harvie et al. |
| 6,620,195 | B2 | 9/2003 | Goble et al. |
| 6,620,329 | B2 | 9/2003 | Rosen et al. |
| 6,620,349 | B1 | 9/2003 | Lopez |
| 6,623,492 | B1 | 9/2003 | Berube et al. |
| 6,623,524 | B2 | 9/2003 | Schmieding |
| 6,626,910 | B1 | 9/2003 | Hugues |
| 6,626,919 | B1 | 9/2003 | Swanstrom |
| 6,626,930 | B1 | 9/2003 | Allen et al. |
| 6,629,977 | B1 | 10/2003 | Wolf |
| 6,629,997 | B2 | 10/2003 | Mansmann |
| 6,632,245 | B2 | 10/2003 | Kim |
| 6,635,073 | B2 | 10/2003 | Bonutti |
| 6,638,279 | B2 | 10/2003 | Bonutti |
| 6,638,286 | B1 | 10/2003 | Burbank et al. |

(56) References Cited

U.S. PATENT DOCUMENTS

| | | | |
|---|---|---|---|
| 6,638,312 | B2 | 10/2003 | Plouhar et al. |
| 6,641,596 | B1 | 11/2003 | Lizardi |
| 6,641,597 | B2 | 11/2003 | Burkhart et al. |
| 6,645,169 | B1 | 11/2003 | Slate et al. |
| 6,645,211 | B2 | 11/2003 | Magana |
| 6,645,227 | B2 | 11/2003 | Fallin et al. |
| 6,648,903 | B1 | 11/2003 | Pierson, III |
| 6,648,921 | B2 | 11/2003 | Anderson et al. |
| 6,652,450 | B2 | 11/2003 | Neisz et al. |
| 6,652,533 | B2 | 11/2003 | O'neil |
| 6,652,560 | B1 | 11/2003 | Gerke et al. |
| 6,652,562 | B2 | 11/2003 | Collier et al. |
| 6,652,563 | B2 | 11/2003 | Dreyfuss |
| 6,656,182 | B1 | 12/2003 | Hayhurst |
| 6,656,183 | B2 | 12/2003 | Colleran et al. |
| 6,658,182 | B1 | 12/2003 | Gonthier et al. |
| 6,660,008 | B1 | 12/2003 | Foerster et al. |
| 6,660,022 | B1 | 12/2003 | Li et al. |
| 6,663,634 | B2 | 12/2003 | Ahrens et al. |
| 6,663,656 | B2 | 12/2003 | Schmieding et al. |
| 6,666,868 | B2 | 12/2003 | Fallin |
| 6,666,877 | B2 | 12/2003 | Morgan et al. |
| 6,669,707 | B1 | 12/2003 | Swanstrom et al. |
| 6,679,889 | B1 | 1/2004 | West, Jr. et al. |
| 6,682,533 | B1 | 1/2004 | Dinsdale et al. |
| 6,682,549 | B2 | 1/2004 | Bartlett |
| 6,685,728 | B2 | 2/2004 | Sinnott et al. |
| 6,689,137 | B2 | 2/2004 | Reed |
| 6,689,153 | B1 | 2/2004 | Skiba |
| 6,689,154 | B2 | 2/2004 | Bartlett |
| 6,692,499 | B2 | 2/2004 | Tormala et al. |
| 6,692,516 | B2 | 2/2004 | West, Jr. et al. |
| 6,695,852 | B2 | 2/2004 | Gleason |
| 6,712,849 | B2 | 3/2004 | Re et al. |
| 6,712,859 | B2 | 3/2004 | Rousseau |
| 6,716,190 | B1 | 4/2004 | Glines et al. |
| 6,716,224 | B2 | 4/2004 | Singhatat |
| 6,716,957 | B2 | 4/2004 | Tunc |
| 6,730,092 | B2 | 5/2004 | Songer |
| 6,730,124 | B2 | 5/2004 | Steiner |
| 6,736,799 | B1 | 5/2004 | Erbe et al. |
| 6,737,053 | B1 | 5/2004 | Goh et al. |
| 6,746,483 | B1 | 6/2004 | Bojarski et al. |
| 6,752,780 | B2 | 6/2004 | Stout et al. |
| 6,752,810 | B1 | 6/2004 | Gao et al. |
| 6,752,831 | B2 | 6/2004 | Sybert et al. |
| 6,755,836 | B1 | 6/2004 | Lewis |
| 6,755,868 | B2 | 6/2004 | Rousseau |
| 6,761,722 | B2 | 7/2004 | Cole et al. |
| 6,761,739 | B2 | 7/2004 | Shepard |
| 6,767,037 | B2 | 7/2004 | Wenstrom, Jr. |
| 6,770,076 | B2 | 8/2004 | Foerster |
| 6,770,084 | B1 | 8/2004 | Bain et al. |
| 6,773,450 | B2 | 8/2004 | Leung et al. |
| 6,779,701 | B2 | 8/2004 | Bailly et al. |
| 6,780,190 | B2 | 8/2004 | Maroney |
| 6,780,198 | B1 | 8/2004 | Gregoire et al. |
| 6,790,210 | B1 | 9/2004 | Cragg et al. |
| 6,793,595 | B1 | 9/2004 | Monnet |
| 6,802,862 | B1 | 10/2004 | Roger et al. |
| 6,808,502 | B2 | 10/2004 | Nguyen et al. |
| 6,808,526 | B1 | 10/2004 | Magerl et al. |
| 6,814,741 | B2 | 11/2004 | Bowman et al. |
| 6,830,572 | B2 | 12/2004 | McDevitt et al. |
| 6,833,005 | B1 | 12/2004 | Mantas et al. |
| 6,835,377 | B2 | 12/2004 | Goldberg et al. |
| 6,840,953 | B2 | 1/2005 | Martinek |
| 6,860,885 | B2 | 3/2005 | Bonutti |
| 6,860,895 | B1 | 3/2005 | Akerfeldt et al. |
| 6,863,671 | B1 | 3/2005 | Strobel et al. |
| 6,872,040 | B2 | 3/2005 | Deeg et al. |
| 6,872,210 | B2 | 3/2005 | Hearn |
| 6,875,216 | B2 | 4/2005 | Wolf |
| 6,884,249 | B2 | 4/2005 | May et al. |
| 6,887,243 | B2 | 5/2005 | Culbert |
| 6,887,259 | B2 | 5/2005 | Lizardi |
| 6,887,271 | B2 | 5/2005 | Justin et al. |
| 6,890,354 | B2 | 5/2005 | Steiner et al. |
| 6,893,448 | B2 | 5/2005 | O'Quinn et al. |
| 6,896,686 | B2 | 5/2005 | Weber |
| 6,899,722 | B2 | 5/2005 | Bonutti |
| 6,902,573 | B2 | 6/2005 | Strobel et al. |
| 6,905,513 | B1 | 6/2005 | Metzger |
| 6,908,466 | B1 | 6/2005 | Bonutti et al. |
| 6,911,202 | B2 | 6/2005 | Amir et al. |
| 6,916,292 | B2 | 7/2005 | Morawski et al. |
| 6,916,321 | B2 | 7/2005 | TenHuisen et al. |
| 6,921,402 | B2 | 7/2005 | Contiliano et al. |
| 6,923,823 | B1 | 8/2005 | Bartlett et al. |
| 6,923,824 | B2 | 8/2005 | Morgan et al. |
| 6,939,379 | B2 | 9/2005 | Sklar |
| 6,949,102 | B2 | 9/2005 | Andrews |
| 6,951,565 | B2 | 10/2005 | Keane et al. |
| 6,960,214 | B2 | 11/2005 | Burkinshaw |
| 6,966,887 | B1 | 11/2005 | Chin |
| 6,966,916 | B2 | 11/2005 | Kumar |
| 6,969,391 | B1 | 11/2005 | Gazzani |
| 6,969,398 | B2 | 11/2005 | Stevens et al. |
| 6,972,027 | B2 | 12/2005 | Fallin et al. |
| 6,980,903 | B2 | 12/2005 | Daniels et al. |
| 6,984,237 | B2 | 1/2006 | Hatch et al. |
| 6,986,781 | B2 | 1/2006 | Smith |
| 6,989,034 | B2 | 1/2006 | Hammer et al. |
| 6,994,719 | B2 | 2/2006 | Grafton |
| 6,994,725 | B1 | 2/2006 | Goble |
| 7,001,429 | B2 | 2/2006 | Ferguson |
| 7,004,959 | B2 | 2/2006 | Bonutti |
| 7,008,451 | B2 | 3/2006 | Justin et al. |
| 7,048,754 | B2 | 5/2006 | Martin et al. |
| 7,052,499 | B2 | 5/2006 | Steger et al. |
| 7,066,942 | B2 | 6/2006 | Treace |
| 7,066,944 | B2 | 6/2006 | Laufer et al. |
| 7,081,126 | B2 | 7/2006 | McDevitt et al. |
| 7,083,638 | B2 | 8/2006 | Foerster |
| 7,087,064 | B1 | 8/2006 | Hyde |
| 7,087,073 | B2 | 8/2006 | Bonutti |
| 7,097,654 | B1 | 8/2006 | Freedland |
| 7,101,395 | B2 | 9/2006 | Tremulis et al. |
| 7,105,010 | B2 | 9/2006 | Hart et al. |
| 7,112,221 | B2 | 9/2006 | Harris |
| 7,118,578 | B2 | 10/2006 | West, Jr. et al. |
| 7,118,583 | B2 | 10/2006 | O'Quinn et al. |
| 7,125,421 | B2 | 10/2006 | Tremulis et al. |
| 7,131,467 | B2 | 11/2006 | Gao et al. |
| 7,137,996 | B2 | 11/2006 | Steiner et al. |
| 7,141,066 | B2 | 11/2006 | Steiner et al. |
| 7,144,414 | B2 | 12/2006 | Harvie et al. |
| 7,148,209 | B2 | 12/2006 | Hoemann et al. |
| 7,153,127 | B2 | 12/2006 | Struble et al. |
| 7,153,307 | B2 | 12/2006 | Scribner et al. |
| 7,153,312 | B1 | 12/2006 | Torrie et al. |
| 7,153,327 | B1 | 12/2006 | Metzger |
| 7,160,285 | B2 | 1/2007 | Sklar et al. |
| 7,160,333 | B2 | 1/2007 | Plouhar et al. |
| 7,172,626 | B1 | 2/2007 | Andrews |
| 7,179,259 | B1 | 2/2007 | Gibbs |
| 7,201,722 | B2 | 4/2007 | Krueger |
| 7,207,993 | B1 | 4/2007 | Baldwin et al. |
| 7,229,441 | B2 | 6/2007 | Trieu et al. |
| 7,255,675 | B2 | 8/2007 | Gertner et al. |
| 7,255,700 | B2 | 8/2007 | Kaiser et al. |
| 7,255,715 | B2 | 8/2007 | Metzger |
| 7,261,716 | B2 | 8/2007 | Strobel et al. |
| 7,264,634 | B2 | 9/2007 | Schmieding |
| 7,279,008 | B2 | 10/2007 | Brown et al. |
| 7,285,124 | B2 | 10/2007 | Foerster |
| 7,291,177 | B2 | 11/2007 | Gibbs |
| 7,303,577 | B1 | 12/2007 | Dean |
| 7,306,417 | B2 | 12/2007 | Dorstewitz |
| 7,309,355 | B2 | 12/2007 | Donnelly et al. |
| 7,326,222 | B2 | 2/2008 | Dreyfuss et al. |
| 7,329,272 | B2 | 2/2008 | Burkhart et al. |
| 7,361,179 | B2 | 4/2008 | Rousseau et al. |
| 7,377,845 | B2 | 5/2008 | Stewart et al. |

(56) References Cited

U.S. PATENT DOCUMENTS 7,390,329 B2 6/2008 Westra et al.
7,390,332 B2 6/2008 Selvitelli et al.
7,399,018 B1 7/2008 Khachaturian
7,442,210 B2 10/2008 Segal et al.
7,465,308 B2 12/2008 Sikora et al.
7,468,074 B2 12/2008 Caborn et al.
7,481,814 B1 1/2009 Metzger
7,484,539 B1 2/2009 Huang
7,485,149 B1 2/2009 White
7,494,506 B2 2/2009 Brulez et al.
D587,807 S 3/2009 Wolf et al.
7,500,983 B1 3/2009 Kaiser et al.
7,513,910 B2 4/2009 Buskirk et al.
7,517,357 B2 4/2009 Abrams et al.
7,572,275 B2 8/2009 Fallin et al.
7,572,298 B2 8/2009 Roller et al.
7,578,825 B2 8/2009 Huebner
7,585,311 B2 9/2009 Green et al.
7,588,587 B2 9/2009 Barbieri et al.
7,591,823 B2 9/2009 Tipirneni
7,597,705 B2 10/2009 Forsberg et al.
7,601,165 B2 10/2009 Stone
7,604,636 B1 10/2009 Walters et al.
7,608,092 B1 10/2009 Schaffhausen
7,608,098 B1 10/2009 Stone et al.
7,615,076 B2 11/2009 Cauthen, III et al.
7,621,937 B2 11/2009 Pipenhagen et al.
7,632,287 B2 12/2009 Baker et al.
7,651,509 B2 1/2010 Bojarski et al.
7,658,750 B2 2/2010 Li
7,658,751 B2 2/2010 Stone et al.
7,670,279 B2 3/2010 Gertner
7,678,123 B2 3/2010 Chanduszko
7,691,112 B2 4/2010 Chanduszko et al.
7,695,493 B2 4/2010 Saadat et al.
7,695,503 B1 4/2010 Kaiser et al.
7,703,372 B1 4/2010 Shakespeare
7,713,285 B1 5/2010 Stone et al.
7,717,929 B2 5/2010 Fallman
7,731,732 B2 6/2010 Ken
7,736,364 B2 6/2010 Stone
7,736,379 B2 6/2010 Ewers et al.
7,749,250 B2 7/2010 Stone et al.
7,758,594 B2 7/2010 Lamson et al.
7,758,611 B2 7/2010 Kato
7,762,942 B2 7/2010 Neisz et al.
7,771,482 B1 8/2010 Karmon
7,776,041 B1 8/2010 Walters
7,790,945 B1 9/2010 Watson, Jr.
7,803,173 B2 9/2010 Burkhart et al.
7,819,895 B2 10/2010 Ginn et al.
7,828,820 B2 11/2010 Stone et al.
7,828,850 B2 11/2010 Cauthen, III et al.
7,856,698 B2 12/2010 Hays
7,857,830 B2 12/2010 Stone et al.
7,867,252 B2 1/2011 Criscuolo et al.
7,867,264 B2 1/2011 McDevitt et al.
7,875,058 B2 1/2011 Holmes, Jr.
7,878,058 B2 2/2011 Blendinger et al.
7,887,586 B2 2/2011 Linares
7,896,907 B2 3/2011 Mcdevitt et al.
7,905,903 B2 3/2011 Stone et al.
7,905,904 B2 3/2011 Stone et al.
7,909,851 B2 3/2011 Stone et al.
7,914,539 B2 3/2011 Stone et al.
7,938,847 B2 5/2011 Fanton et al.
7,951,198 B2 5/2011 Sucec et al.
7,955,388 B2 6/2011 Jensen et al.
7,959,650 B2 6/2011 Kaiser et al.
7,976,565 B1 7/2011 Meridew
7,981,140 B2 7/2011 Burkhart
7,998,203 B2 8/2011 Blum
8,034,090 B2 10/2011 Stone et al.
8,062,334 B2 11/2011 Green et al.
8,075,574 B2 12/2011 May et al.
8,088,108 B2 1/2012 Kraft
8,088,130 B2 1/2012 Kaiser et al.
8,109,867 B2 2/2012 Rosenblatt
8,114,127 B2 2/2012 West, Jr.
8,114,128 B2 2/2012 Cauldwell et al.
8,118,835 B2 2/2012 Weisel et al.
8,118,836 B2 2/2012 Denham et al.
8,118,868 B2 2/2012 May et al.
8,128,658 B2 3/2012 Kaiser et al.
8,137,354 B2 3/2012 Stone
8,137,382 B2 3/2012 Denham et al.
8,162,997 B2 4/2012 Struhl
8,167,906 B2 5/2012 Cauldwell et al.
8,177,810 B2 5/2012 Ferree
8,202,295 B2 6/2012 Kaplan
8,202,318 B2 6/2012 Willobee
8,221,454 B2 7/2012 Schaffhausen
8,231,654 B2 7/2012 Kaiser et al.
8,251,998 B2 8/2012 Hoeppner et al.
8,252,022 B2 8/2012 Holman et al.
8,273,106 B2 9/2012 Stone et al.
8,292,921 B2 10/2012 Stone et al.
8,298,262 B2 10/2012 Stone et al.
8,298,284 B2 10/2012 Cassani
8,303,604 B2 11/2012 Stone et al.
8,317,825 B2 11/2012 Stone
8,337,525 B2 12/2012 Stone et al.
8,343,155 B2 1/2013 Fisher et al.
8,343,227 B2 1/2013 Metzger et al.
8,361,054 B2 1/2013 Ducharme et al.
8,361,113 B2 1/2013 Stone et al.
8,409,253 B2 4/2013 Stone et al.
8,486,114 B2 7/2013 Gillard et al.
8,500,818 B2 8/2013 Metzger et al.
8,506,597 B2 8/2013 Kaiser et al.
8,551,140 B2 10/2013 Denham et al.
8,562,645 B2 10/2013 Stone et al.
8,562,647 B2 10/2013 Kaiser et al.
8,574,235 B2 11/2013 Stone
8,579,944 B2 11/2013 Holloway et al.
8,597,327 B2 12/2013 Stone et al.
8,608,777 B2 12/2013 Kaiser et al.
8,632,566 B2 1/2014 Olson
8,632,569 B2 1/2014 Stone et al.
8,652,171 B2 2/2014 Stone et al.
8,652,172 B2 2/2014 Denham et al.
8,672,904 B1 3/2014 Schultz
8,672,968 B2 3/2014 Stone et al.
8,672,969 B2 3/2014 Stone et al.
8,702,718 B2 4/2014 Bhatnagar et al.
8,721,650 B2 5/2014 Fanton et al.
8,721,684 B2 5/2014 Denham et al.
8,771,316 B2 7/2014 Denham et al.
8,771,352 B2 7/2014 Conner et al.
8,777,956 B2 7/2014 Hoeppner et al.
8,801,783 B2 8/2014 Stone et al.
8,808,374 B2 8/2014 Eggli
8,840,645 B2 9/2014 Denham et al.
8,900,314 B2 12/2014 Metzger et al.
8,926,613 B2 1/2015 Kaiser et al.
8,932,331 B2 1/2015 Kaiser et al.
8,936,621 B2 1/2015 Denham et al.
8,961,548 B2 2/2015 Buser
8,968,364 B2 3/2015 Berelsman et al.
8,998,949 B2 4/2015 Stone et al.
9,005,287 B2 4/2015 Stone
9,017,381 B2 4/2015 Kaiser et al.
9,023,058 B2 5/2015 Jaramillo et al.
9,078,644 B2 7/2015 Stone
9,149,267 B2 10/2015 Norton et al.
9,173,651 B2 11/2015 Stone et al.
9,198,673 B2 12/2015 Stone
9,216,078 B2 12/2015 Conner et al.
9,271,713 B2 3/2016 Denham et al.
9,271,826 B2 3/2016 Eggli et al.
9,289,285 B2 3/2016 Eggli
9,314,235 B2 4/2016 Bojarski et al.
9,314,241 B2 4/2016 Stone et al.
9,357,991 B2 6/2016 Denham et al.

(56) References Cited

U.S. PATENT DOCUMENTS

| | | | |
|---|---|---|---|
| 9,357,992 | B2 | 6/2016 | Stone et al. |
| 9,370,350 | B2 | 6/2016 | Norton |
| 9,381,013 | B2 | 7/2016 | Norton |
| 9,402,621 | B2 | 8/2016 | Stone et al. |
| 9,408,599 | B2 | 8/2016 | Kaiser et al. |
| 9,414,833 | B2 | 8/2016 | Stone et al. |
| 9,414,925 | B2 | 8/2016 | Metzger et al. |
| 9,486,211 | B2 | 11/2016 | Stone et al. |
| 9,492,158 | B2 | 11/2016 | Stone et al. |
| 9,498,204 | B2 | 11/2016 | Denham et al. |
| 9,510,819 | B2 | 12/2016 | Stone et al. |
| 9,510,821 | B2 | 12/2016 | Denham et al. |
| 9,532,777 | B2 | 1/2017 | Kaiser et al. |
| 9,538,998 | B2 | 1/2017 | Stone et al. |
| 9,539,003 | B2 | 1/2017 | Stone et al. |
| 9,561,025 | B2 | 2/2017 | Stone et al. |
| 9,572,655 | B2 | 2/2017 | Denham |
| 2001/0002439 | A1 | 5/2001 | Bonutti et al. |
| 2001/0010005 | A1 | 7/2001 | Kammerer et al. |
| 2001/0014825 | A1 | 8/2001 | Burke et al. |
| 2001/0019649 | A1 | 9/2001 | Field et al. |
| 2001/0029387 | A1 | 10/2001 | Wolf et al. |
| 2001/0037131 | A1 | 11/2001 | Schmieding et al. |
| 2001/0037153 | A1 | 11/2001 | Rockwood et al. |
| 2001/0041916 | A1 | 11/2001 | Bonutti |
| 2001/0041937 | A1 | 11/2001 | Rieser et al. |
| 2001/0041938 | A1 | 11/2001 | Hein |
| 2001/0044639 | A1 | 11/2001 | Levinson |
| 2001/0047206 | A1 | 11/2001 | Sklar et al. |
| 2001/0051815 | A1 | 12/2001 | Esplin |
| 2001/0051816 | A1 | 12/2001 | Enzerink et al. |
| 2001/0053934 | A1 | 12/2001 | Schmieding |
| 2002/0001964 | A1 | 1/2002 | Choi |
| 2002/0004669 | A1 | 1/2002 | Bartlett |
| 2002/0007182 | A1 | 1/2002 | Kim |
| 2002/0010513 | A1 | 1/2002 | Schmieding |
| 2002/0013607 | A1 | 1/2002 | Lemer |
| 2002/0013608 | A1 | 1/2002 | ElAttrache et al. |
| 2002/0019649 | A1 | 2/2002 | Sikora et al. |
| 2002/0029048 | A1 | 3/2002 | Miller |
| 2002/0029066 | A1 | 3/2002 | Foerster |
| 2002/0032465 | A1 | 3/2002 | Lemer |
| 2002/0045902 | A1 | 4/2002 | Bonutti |
| 2002/0052628 | A1 | 5/2002 | Bowman |
| 2002/0055780 | A1 | 5/2002 | Sklar |
| 2002/0058966 | A1 | 5/2002 | Tormala et al. |
| 2002/0068254 | A1 | 6/2002 | Campbell |
| 2002/0077629 | A1 | 6/2002 | Hoffman et al. |
| 2002/0077659 | A1 | 6/2002 | Johnson et al. |
| 2002/0082220 | A1 | 6/2002 | Hoemann et al. |
| 2002/0091391 | A1 | 7/2002 | Cole et al. |
| 2002/0099411 | A1 | 7/2002 | Bartlett |
| 2002/0111591 | A1 | 8/2002 | Mckinnon et al. |
| 2002/0111653 | A1 | 8/2002 | Foerster |
| 2002/0120270 | A1 | 8/2002 | Trieu et al. |
| 2002/0120292 | A1 | 8/2002 | Morgan |
| 2002/0123752 | A1 | 9/2002 | Schultheiss et al. |
| 2002/0128654 | A1 | 9/2002 | Steger et al. |
| 2002/0128684 | A1 | 9/2002 | Foerster |
| 2002/0129820 | A1 | 9/2002 | Ryan et al. |
| 2002/0143336 | A1 | 10/2002 | Hearn |
| 2002/0147463 | A1 | 10/2002 | Martinek |
| 2002/0156475 | A1 | 10/2002 | Lerch et al. |
| 2002/0161401 | A1 | 10/2002 | Steiner |
| 2002/0161439 | A1 | 10/2002 | Strobel et al. |
| 2002/0165548 | A1 | 11/2002 | Jutley |
| 2002/0165611 | A1 | 11/2002 | Enzerink et al. |
| 2002/0169452 | A1 | 11/2002 | Tormala et al. |
| 2002/0169477 | A1 | 11/2002 | Demopulos et al. |
| 2002/0169478 | A1 | 11/2002 | Schwartz et al. |
| 2002/0173788 | A1 | 11/2002 | Bojarski et al. |
| 2002/0177853 | A1 | 11/2002 | Chervitz et al. |
| 2002/0188298 | A1 | 12/2002 | Chan |
| 2002/0193830 | A1 | 12/2002 | Bonutti |
| 2003/0004545 | A1 | 1/2003 | Burkhart et al. |
| 2003/0009235 | A1 | 1/2003 | Manrique et al. |
| 2003/0023268 | A1 | 1/2003 | Lizardi |
| 2003/0032961 | A1 | 2/2003 | Pelo et al. |
| 2003/0033021 | A1 | 2/2003 | Plouhar et al. |
| 2003/0033022 | A1 | 2/2003 | Plouhar et al. |
| 2003/0036797 | A1 | 2/2003 | Malaviya et al. |
| 2003/0036801 | A1 | 2/2003 | Schwartz et al. |
| 2003/0065391 | A1 | 4/2003 | Re et al. |
| 2003/0065402 | A1 | 4/2003 | Anderson et al. |
| 2003/0078585 | A1 | 4/2003 | Johnson et al. |
| 2003/0078603 | A1 | 4/2003 | Schaller et al. |
| 2003/0078617 | A1 | 4/2003 | Schwartz et al. |
| 2003/0083662 | A1 | 5/2003 | Middleton |
| 2003/0083694 | A1 | 5/2003 | Miller |
| 2003/0088251 | A1 | 5/2003 | Braun et al. |
| 2003/0088272 | A1 | 5/2003 | Smith |
| 2003/0105477 | A1 | 6/2003 | Schwartz et al. |
| 2003/0105489 | A1 | 6/2003 | Eichhorn et al. |
| 2003/0114929 | A1 | 6/2003 | Knudsen |
| 2003/0120309 | A1 | 6/2003 | Colleran et al. |
| 2003/0130670 | A1 | 7/2003 | Anderson et al. |
| 2003/0130694 | A1 | 7/2003 | Bojarski et al. |
| 2003/0130695 | A1 | 7/2003 | McDevitt et al. |
| 2003/0135214 | A1 | 7/2003 | Fetto et al. |
| 2003/0135239 | A1 | 7/2003 | Gabriel et al. |
| 2003/0135963 | A1 | 7/2003 | Holbrook et al. |
| 2003/0139752 | A1 | 7/2003 | Pasricha et al. |
| 2003/0139775 | A1 | 7/2003 | Grafton |
| 2003/0149448 | A1 | 8/2003 | Foerster et al. |
| 2003/0152522 | A1 | 8/2003 | Miller et al. |
| 2003/0153947 | A1 | 8/2003 | Koseki |
| 2003/0167072 | A1 | 9/2003 | Oberlander |
| 2003/0167090 | A1 | 9/2003 | Chervitz et al. |
| 2003/0171811 | A1 | 9/2003 | Steiner et al. |
| 2003/0176865 | A1 | 9/2003 | Supinski |
| 2003/0176919 | A1 | 9/2003 | Schmieding |
| 2003/0176920 | A1 | 9/2003 | Sklar et al. |
| 2003/0181925 | A1 | 9/2003 | Bain et al. |
| 2003/0195528 | A1 | 10/2003 | Ritchart |
| 2003/0195564 | A1 | 10/2003 | Tran et al. |
| 2003/0208209 | A1 | 11/2003 | Gambale et al. |
| 2003/0208210 | A1 | 11/2003 | Dreyfuss et al. |
| 2003/0212456 | A1 | 11/2003 | Lipchitz et al. |
| 2003/0216809 | A1 | 11/2003 | Ferguson |
| 2003/0220646 | A1 | 11/2003 | Thelen et al. |
| 2003/0220660 | A1 | 11/2003 | Kortenbach et al. |
| 2003/0225459 | A1 | 12/2003 | Hammer et al. |
| 2003/0229361 | A1 | 12/2003 | Jackson |
| 2003/0229396 | A1 | 12/2003 | Andrews |
| 2003/0236555 | A1 | 12/2003 | Thornes |
| 2004/0002734 | A1 | 1/2004 | Fallin et al. |
| 2004/0006345 | A1 | 1/2004 | Vlahos et al. |
| 2004/0006346 | A1 | 1/2004 | Holmen et al. |
| 2004/0015171 | A1 | 1/2004 | Bojarski et al. |
| 2004/0015172 | A1 | 1/2004 | Biedermann et al. |
| 2004/0024456 | A1 | 2/2004 | Brown et al. |
| 2004/0024457 | A1 | 2/2004 | Boyce et al. |
| 2004/0039389 | A1 | 2/2004 | West et al. |
| 2004/0044391 | A1 | 3/2004 | Porter |
| 2004/0059357 | A1 | 3/2004 | Koseki |
| 2004/0073176 | A1 | 4/2004 | Utterberg |
| 2004/0087981 | A1 | 5/2004 | Berube et al. |
| 2004/0092936 | A1 | 5/2004 | Miller et al. |
| 2004/0093031 | A1 | 5/2004 | Burkhart et al. |
| 2004/0093032 | A1 | 5/2004 | Sinnott et al. |
| 2004/0098051 | A1 | 5/2004 | Fallin et al. |
| 2004/0098053 | A1 | 5/2004 | Tran |
| 2004/0111117 | A1 | 6/2004 | Colleran et al. |
| 2004/0122431 | A1 | 6/2004 | Biedermann et al. |
| 2004/0127907 | A1 | 7/2004 | Dakin et al. |
| 2004/0133206 | A1 | 7/2004 | Stevens et al. |
| 2004/0133211 | A1 | 7/2004 | Raskin et al. |
| 2004/0133238 | A1 | 7/2004 | Cerier |
| 2004/0138664 | A1 | 7/2004 | Bowman |
| 2004/0138683 | A1 | 7/2004 | Shelton et al. |
| 2004/0138704 | A1 | 7/2004 | Gambale et al. |
| 2004/0138706 | A1 | 7/2004 | Abrams et al. |
| 2004/0138747 | A1 | 7/2004 | Kaladelfos |
| 2004/0143344 | A1 | 7/2004 | Malaviya et al. |

(56) References Cited

U.S. PATENT DOCUMENTS

2004/0147932 A1 7/2004 Burkinshaw et al.
2004/0147958 A1 7/2004 Lam et al.
2004/0153103 A1 8/2004 Schwartz et al.
2004/0153153 A1 8/2004 Elson et al.
2004/0162579 A1 8/2004 Foerster
2004/0166169 A1 8/2004 Malaviya et al.
2004/0181234 A1 9/2004 McDevitt et al.
2004/0182968 A1 9/2004 Gentry
2004/0187314 A1 9/2004 Johnson
2004/0193185 A1 9/2004 McBrayer
2004/0199169 A1 10/2004 Koons et al.
2004/0204722 A1 10/2004 Sikora et al.
2004/0220574 A1 11/2004 Pelo et al.
2004/0225183 A1 11/2004 Michlitsch et al.
2004/0225292 A1 11/2004 Sasso et al.
2004/0225305 A1 11/2004 Ewers et al.
2004/0236353 A1 11/2004 Bain et al.
2004/0236373 A1 11/2004 Anspach
2004/0243139 A1 12/2004 Lewis et al.
2004/0243178 A1 12/2004 Haut et al.
2004/0243180 A1 12/2004 Donnelly et al.
2004/0243235 A1 12/2004 Goh et al.
2004/0249394 A1 12/2004 Morris et al.
2004/0260296 A1 12/2004 Kaiser et al.
2004/0260298 A1 12/2004 Kaiser et al.
2004/0267164 A1 12/2004 Rhodes et al.
2004/0267265 A1 12/2004 Kyle
2004/0267270 A1 12/2004 Jacobs et al.
2004/0267276 A1 12/2004 Camino et al.
2004/0267277 A1 12/2004 Zannis et al.
2004/0267286 A1 12/2004 Gao et al.
2004/0267304 A1 12/2004 Zannis et al.
2004/0267309 A1 12/2004 Garvin
2004/0267317 A1 12/2004 Higgins et al.
2004/0267361 A1 12/2004 Donnelly et al.
2004/0267362 A1 12/2004 Hwang et al.
2005/0004670 A1 1/2005 Gebhardt et al.
2005/0021087 A1 1/2005 Koseki
2005/0021148 A1 1/2005 Gibbs
2005/0027307 A1 2/2005 Schwartz et al.
2005/0033363 A1 2/2005 Bojarski et al.
2005/0038426 A1 2/2005 Chan
2005/0049598 A1 3/2005 West, Jr. et al.
2005/0055027 A1 3/2005 Yeung et al.
2005/0055037 A1 3/2005 Fathauer
2005/0064042 A1 3/2005 Vunjak-Novakovic et al.
2005/0065521 A1 3/2005 Steger et al.
2005/0065526 A1 3/2005 Drew et al.
2005/0070906 A1 3/2005 Clark et al.
2005/0070928 A1 3/2005 Heino et al.
2005/0074495 A1 4/2005 Schwartz et al.
2005/0076478 A1 4/2005 Miyazaki et al.
2005/0085819 A1 4/2005 Ellis et al.
2005/0090827 A1 4/2005 Gedebou
2005/0090828 A1 4/2005 Alford
2005/0090862 A1 4/2005 McDevitt et al.
2005/0096696 A1 5/2005 Forsberg
2005/0096697 A1 5/2005 Forsberg et al.
2005/0096743 A1 5/2005 Schmieding et al.
2005/0101957 A1 5/2005 Buskirk et al.
2005/0107795 A1 5/2005 Morris et al.
2005/0107828 A1 5/2005 Reese
2005/0107882 A1 5/2005 Stone et al.
2005/0119531 A1 6/2005 Sharratt
2005/0119696 A1 6/2005 Walters et al.
2005/0124996 A1 6/2005 Hearn
2005/0125031 A1 6/2005 Pipenhagen et al.
2005/0125036 A1 6/2005 Roby
2005/0125073 A1 6/2005 Orban et al.
2005/0130301 A1 6/2005 Mckay et al.
2005/0131413 A1 6/2005 O'Driscoll et al.
2005/0137600 A1 6/2005 Jacobs et al.
2005/0137624 A1 6/2005 Fallman
2005/0149033 A1 7/2005 McGuire et al.
2005/0149118 A1 7/2005 Koyfman et al.
2005/0149122 A1 7/2005 McDevitt et al.
2005/0149187 A1 7/2005 Clark et al.
2005/0159812 A1 7/2005 Dinger et al.
2005/0165416 A1 7/2005 Bojarski et al.
2005/0165482 A1 7/2005 Goldhahn et al.
2005/0171547 A1 8/2005 Aram
2005/0171603 A1 8/2005 Justin et al.
2005/0171604 A1 8/2005 Michalow
2005/0177237 A1 8/2005 Shappley et al.
2005/0187565 A1 8/2005 Baker et al.
2005/0187577 A1 8/2005 Selvitelli et al.
2005/0187635 A1 8/2005 Metzger
2005/0192632 A1 9/2005 Geissler et al.
2005/0203620 A1 9/2005 Steiner et al.
2005/0222618 A1 10/2005 Dreyfuss et al.
2005/0222619 A1 10/2005 Dreyfuss et al.
2005/0228448 A1 10/2005 Li
2005/0240198 A1 10/2005 Albertson et al.
2005/0251153 A1 11/2005 Sakamoto et al.
2005/0251159 A1 11/2005 Ewers et al.
2005/0251177 A1 11/2005 Saadat et al.
2005/0251208 A1 11/2005 Elmer et al.
2005/0251209 A1 11/2005 Saadat et al.
2005/0251210 A1 11/2005 Westra et al.
2005/0261642 A1 11/2005 Weston
2005/0267479 A1 12/2005 Morgan et al.
2005/0267533 A1 12/2005 Gertner
2005/0277939 A1 12/2005 Miller
2005/0277961 A1 12/2005 Stone et al.
2005/0283040 A1 12/2005 Greenhalgh
2005/0283156 A1 12/2005 Schmieding et al.
2005/0283158 A1 12/2005 West
2005/0283192 A1 12/2005 Torrie et al.
2006/0004364 A1 1/2006 Green et al.
2006/0004410 A1 1/2006 Nobis et al.
2006/0015103 A1 1/2006 Burke
2006/0015106 A1 1/2006 Lerch et al.
2006/0015107 A1 1/2006 Sklar
2006/0030884 A1 2/2006 Yeung et al.
2006/0030948 A1 2/2006 Manrique et al.
2006/0036265 A1 2/2006 Dant
2006/0052787 A1 3/2006 Re et al.
2006/0052818 A1 3/2006 Drake et al.
2006/0064125 A1 3/2006 Henderson et al.
2006/0064126 A1 3/2006 Fallin et al.
2006/0069334 A1 3/2006 Moskowitz
2006/0079904 A1 4/2006 Thal
2006/0084943 A1 4/2006 Rosenman et al.
2006/0085000 A1 4/2006 Mohr et al.
2006/0089672 A1 4/2006 Martinek
2006/0095130 A1 5/2006 Caborn et al.
2006/0095131 A1 5/2006 Justin et al.
2006/0100627 A1 5/2006 Stone et al.
2006/0100637 A1 5/2006 Rathbun et al.
2006/0106423 A1 5/2006 Weisel et al.
2006/0111721 A1 5/2006 Puricelli et al.
2006/0116685 A1 6/2006 Urbanski et al.
2006/0121084 A1 6/2006 Borden et al.
2006/0122608 A1 6/2006 Fallin et al.
2006/0122611 A1 6/2006 Morales et al.
2006/0135958 A1 6/2006 Marissen et al.
2006/0149258 A1 7/2006 Sousa
2006/0149266 A1 7/2006 Cordasco
2006/0155287 A1 7/2006 Montgomery et al.
2006/0155328 A1 7/2006 Foerster
2006/0161161 A1 7/2006 Shifrin et al.
2006/0167458 A1 7/2006 Gabele
2006/0167481 A1 7/2006 Baker et al.
2006/0167482 A1 7/2006 Swain et al.
2006/0173492 A1 8/2006 Akerfeldt et al.
2006/0178680 A1 8/2006 Nelson et al.
2006/0178743 A1 8/2006 Carter
2006/0189993 A1 8/2006 Stone
2006/0190042 A1 8/2006 Stone et al.
2006/0195101 A1 8/2006 Stevens
2006/0195106 A1 8/2006 Jones et al.
2006/0200235 A1 9/2006 Bianchi et al.
2006/0212055 A1 9/2006 Karabey et al.
2006/0229623 A1 10/2006 Bonutti et al.

(56) References Cited

U.S. PATENT DOCUMENTS

2006/0229671 A1 10/2006 Steiner et al.
2006/0229676 A1 10/2006 Doll et al.
2006/0235407 A1 10/2006 Wang et al.
2006/0235413 A1 10/2006 Denham et al.
2006/0241624 A1 10/2006 Kizuka et al.
2006/0241776 A1 10/2006 Brown et al.
2006/0241781 A1 10/2006 Brown et al.
2006/0247642 A1 11/2006 Stone et al.
2006/0253130 A1 11/2006 Wolniewicz
2006/0259048 A1 11/2006 Koseki
2006/0259076 A1 11/2006 Burkhart
2006/0264944 A1 11/2006 Cole
2006/0271192 A1 11/2006 Olsen et al.
2006/0276793 A1 12/2006 Berry
2006/0276809 A1 12/2006 Oliveira
2006/0276818 A1 12/2006 Buser et al.
2006/0276841 A1 12/2006 Barbieri et al.
2006/0276896 A1 12/2006 Fallin et al.
2006/0280768 A1 12/2006 Hwang et al.
2006/0280803 A1 12/2006 Kumar et al.
2006/0282082 A1 12/2006 Fanton et al.
2006/0282083 A1 12/2006 Fanton et al.
2006/0282085 A1 12/2006 Stone et al.
2006/0293709 A1 12/2006 Bojarski et al.
2007/0005068 A1 1/2007 Sklar
2007/0005080 A1 1/2007 Wolniewicz et al.
2007/0010857 A1 1/2007 Sugimoto et al.
2007/0016305 A1 1/2007 Chudik
2007/0021779 A1 1/2007 Garvin et al.
2007/0027476 A1 2/2007 Harris et al.
2007/0032800 A1 2/2007 Ortiz et al.
2007/0032823 A1 2/2007 Tegg
2007/0038218 A1 2/2007 Grevious
2007/0043371 A1 2/2007 Teague et al.
2007/0055249 A1 3/2007 Jensen et al.
2007/0055251 A1 3/2007 Huebner et al.
2007/0055255 A1 3/2007 Siegel
2007/0060922 A1 3/2007 Dreyfuss
2007/0067025 A1 3/2007 Schwartz
2007/0071568 A1 3/2007 Dorstewitz
2007/0073307 A1 3/2007 Scribner et al.
2007/0073319 A1 3/2007 Mikkaichi et al.
2007/0073322 A1 3/2007 Mikkaichi et al.
2007/0078435 A1 4/2007 Stone et al.
2007/0083236 A1 4/2007 Sikora et al.
2007/0088362 A1 4/2007 Bonutti et al.
2007/0093847 A1 4/2007 Scribner et al.
2007/0100350 A1 5/2007 Deffenbaugh et al.
2007/0112384 A1 5/2007 Conlon et al.
2007/0118217 A1 5/2007 Brulez et al.
2007/0123883 A1 5/2007 Ellis et al.
2007/0123984 A1 5/2007 Hodorek
2007/0129809 A1 6/2007 Meridew et al.
2007/0142838 A1 6/2007 Jordan
2007/0156174 A1 7/2007 Kaiser et al.
2007/0162018 A1 7/2007 Jensen et al.
2007/0167926 A1 7/2007 Blott et al.
2007/0167950 A1 7/2007 Tauro et al.
2007/0173948 A1 7/2007 Meridew et al.
2007/0185488 A1 8/2007 Pohjonen et al.
2007/0185532 A1 8/2007 Stone et al.
2007/0185568 A1 8/2007 Schwartz
2007/0191849 A1 8/2007 ElAttrache et al.
2007/0191853 A1 8/2007 Stone
2007/0198022 A1 8/2007 Lang et al.
2007/0198036 A1 8/2007 Sklar et al.
2007/0219558 A1 9/2007 Deutsch
2007/0225715 A1 9/2007 Deffenbaugh et al.
2007/0225719 A1 9/2007 Stone et al.
2007/0225805 A1 9/2007 Schmieding
2007/0233241 A1 10/2007 Graf et al.
2007/0239209 A1 10/2007 Fallman
2007/0239275 A1 10/2007 Willobee
2007/0244565 A1 10/2007 Stchur
2007/0250059 A1 10/2007 Weisshaupt et al.
2007/0250163 A1 10/2007 Cassani
2007/0250175 A1 10/2007 Meridew et al.
2007/0255282 A1 11/2007 Simonton et al.
2007/0260251 A1 11/2007 Weier et al.
2007/0260279 A1 11/2007 Hotter et al.
2007/0265704 A1 11/2007 Mayer et al.
2007/0270856 A1 11/2007 Morales et al.
2007/0270878 A1 11/2007 Leisinger
2007/0276387 A1 11/2007 Morales et al.
2007/0288023 A1 12/2007 Pellegrino et al.
2008/0009904 A1 1/2008 Bourque et al.
2008/0027430 A1 1/2008 Montgomery et al.
2008/0027440 A1 1/2008 Marissen et al.
2008/0027446 A1 1/2008 Stone et al.
2008/0033549 A1 2/2008 Marshall et al.
2008/0046009 A1 2/2008 Albertorio et al.
2008/0051836 A1 2/2008 Foerster et al.
2008/0058787 A1 3/2008 Gertner
2008/0065114 A1 3/2008 Stone et al.
2008/0071299 A1 3/2008 Allinniemi et al.
2008/0082101 A1 4/2008 Reisberg
2008/0082127 A1 4/2008 Stone et al.
2008/0082128 A1 4/2008 Stone
2008/0086138 A1 4/2008 Stone et al.
2008/0097430 A1 4/2008 Bernstein et al.
2008/0114460 A1 5/2008 Willobee et al.
2008/0119892 A1 5/2008 Brailovski et al.
2008/0132753 A1 6/2008 Goddard
2008/0132932 A1 6/2008 Hoeppner et al.
2008/0132948 A1 6/2008 Surti et al.
2008/0133007 A1 6/2008 Donnelly et al.
2008/0137624 A1 6/2008 Silverstrim et al.
2008/0140092 A1 6/2008 Stone et al.
2008/0140093 A1 6/2008 Stone et al.
2008/0140128 A1 6/2008 Smisson et al.
2008/0147187 A1 6/2008 Bollinger et al.
2008/0154260 A1 6/2008 Hoof
2008/0154314 A1 6/2008 McDevitt
2008/0161806 A1 7/2008 Donnelly et al.
2008/0161852 A1 7/2008 Kaiser et al.
2008/0161861 A1 7/2008 Huebner
2008/0161864 A1 7/2008 Beck et al.
2008/0166421 A1 7/2008 Buhr et al.
2008/0172097 A1 7/2008 Lerch et al.
2008/0177302 A1 7/2008 Shurnas
2008/0183290 A1 7/2008 Baird et al.
2008/0188933 A1 8/2008 Koob et al.
2008/0188935 A1 8/2008 Saylor et al.
2008/0188936 A1 8/2008 Ball et al.
2008/0208252 A1 8/2008 Holmes
2008/0217263 A1 9/2008 Higgins et al.
2008/0221527 A1 9/2008 Bradley et al.
2008/0221578 A1 9/2008 Zeitani
2008/0228186 A1 9/2008 Gall et al.
2008/0228271 A1 9/2008 Stone et al.
2008/0234730 A1 9/2008 Cotton et al.
2008/0255613 A1 10/2008 Kaiser et al.
2008/0257363 A1 10/2008 Schoenefeld et al.
2008/0262544 A1 10/2008 Burkhart
2008/0268064 A1 10/2008 Woodell-May
2008/0269674 A1 10/2008 Stone
2008/0275469 A1 11/2008 Fanton et al.
2008/0275477 A1 11/2008 Sterrett et al.
2008/0281428 A1 11/2008 Meyers et al.
2008/0288070 A1 11/2008 Lo
2008/0300611 A1 12/2008 Houser et al.
2008/0312689 A1 12/2008 Denham et al.
2008/0319478 A1 12/2008 Foerster et al.
2009/0018589 A1 1/2009 Smisson, III et al.
2009/0018654 A1 1/2009 Schmieding et al.
2009/0018655 A1 1/2009 Brunelle et al.
2009/0043342 A1 2/2009 Freedland
2009/0054928 A1 2/2009 Denham et al.
2009/0062847 A1 3/2009 Ken
2009/0062854 A1 3/2009 Kaiser et al.
2009/0082790 A1 3/2009 Shad et al.
2009/0082805 A1 3/2009 Kaiser et al.
2009/0084491 A1 4/2009 Uthgenannt et al.
2009/0099598 A1 4/2009 McDevitt et al.

(56) References Cited

U.S. PATENT DOCUMENTS

| | | | |
|---|---|---|---|
| 2009/0105717 | A1 | 4/2009 | Bluechel |
| 2009/0105754 | A1 | 4/2009 | Sethi |
| 2009/0118774 | A1 | 5/2009 | Miller, III |
| 2009/0118775 | A1 | 5/2009 | Burke |
| 2009/0125073 | A1 | 5/2009 | Rehm |
| 2009/0138002 | A1 | 5/2009 | Fenton |
| 2009/0138054 | A1 | 5/2009 | Teague et al. |
| 2009/0156997 | A1 | 6/2009 | Trenhaile |
| 2009/0163949 | A1 | 6/2009 | Rolnick et al. |
| 2009/0177233 | A1 | 7/2009 | Malek |
| 2009/0182335 | A1 | 7/2009 | Struhl |
| 2009/0192468 | A1 | 7/2009 | Stone |
| 2009/0198277 | A1 | 8/2009 | Gordon et al. |
| 2009/0204146 | A1 | 8/2009 | Kaiser et al. |
| 2009/0216325 | A1 | 8/2009 | May et al. |
| 2009/0228015 | A1 | 9/2009 | Ellis |
| 2009/0228042 | A1 | 9/2009 | Koogle, Jr. et al. |
| 2009/0234357 | A1 | 9/2009 | Morales et al. |
| 2009/0234358 | A1 | 9/2009 | Morales et al. |
| 2009/0234451 | A1 | 9/2009 | Manderson |
| 2009/0240251 | A1 | 9/2009 | Gabele |
| 2009/0240335 | A1 | 9/2009 | Arcenio et al. |
| 2009/0248091 | A1 | 10/2009 | Teague et al. |
| 2009/0265014 | A1 | 10/2009 | May et al. |
| 2009/0265015 | A1 | 10/2009 | May et al. |
| 2009/0287215 | A1 | 11/2009 | Fisher et al. |
| 2009/0299409 | A1 | 12/2009 | Coe et al. |
| 2009/0306711 | A1 | 12/2009 | Stone et al. |
| 2009/0312776 | A1 | 12/2009 | Kaiser et al. |
| 2009/0312793 | A1 | 12/2009 | Huxel et al. |
| 2009/0318960 | A1 | 12/2009 | Burkhart |
| 2009/0318961 | A1 | 12/2009 | Stone et al. |
| 2010/0016899 | A1 | 1/2010 | Gelfand |
| 2010/0042114 | A1 | 2/2010 | Schaffhausen |
| 2010/0063541 | A1 | 3/2010 | Brunelle et al. |
| 2010/0087857 | A1 | 4/2010 | Stone et al. |
| 2010/0094355 | A1 | 4/2010 | Trenhaile |
| 2010/0106254 | A1 | 4/2010 | Delsignore |
| 2010/0121348 | A1 | 5/2010 | Van Der et al. |
| 2010/0145384 | A1 | 6/2010 | Stone et al. |
| 2010/0152752 | A1 | 6/2010 | Denove et al. |
| 2010/0191342 | A1 | 7/2010 | Byrd et al. |
| 2010/0204700 | A1 | 8/2010 | Falahee |
| 2010/0211071 | A1 | 8/2010 | Lettmann et al. |
| 2010/0211075 | A1 | 8/2010 | Stone |
| 2010/0256677 | A1 | 10/2010 | Albertorio et al. |
| 2010/0268273 | A1 | 10/2010 | Albertorio et al. |
| 2010/0268275 | A1 | 10/2010 | Stone et al. |
| 2010/0270306 | A1 | 10/2010 | Shiffer |
| 2010/0292792 | A1 | 11/2010 | Stone et al. |
| 2010/0305698 | A1 | 12/2010 | Metzger et al. |
| 2010/0305709 | A1 | 12/2010 | Metzger et al. |
| 2010/0312341 | A1 | 12/2010 | Kaiser et al. |
| 2010/0324676 | A1 | 12/2010 | Albertorio |
| 2010/0331881 | A1 | 12/2010 | Hart |
| 2011/0009885 | A1 | 1/2011 | Graf et al. |
| 2011/0022083 | A1 | 1/2011 | DiMatteo et al. |
| 2011/0026141 | A1 | 2/2011 | Barrows |
| 2011/0046733 | A1 | 2/2011 | Eggli |
| 2011/0087225 | A1 | 4/2011 | Fritzinger |
| 2011/0087280 | A1 | 4/2011 | Albertorio |
| 2011/0087284 | A1 | 4/2011 | Stone et al. |
| 2011/0098727 | A1 | 4/2011 | Kaiser et al. |
| 2011/0106153 | A1 | 5/2011 | Stone et al. |
| 2011/0112537 | A1 | 5/2011 | Bernstein et al. |
| 2011/0112538 | A1 | 5/2011 | Dell'Oca |
| 2011/0160767 | A1 | 6/2011 | Stone et al. |
| 2011/0160768 | A1 | 6/2011 | Stone et al. |
| 2011/0184227 | A1 | 7/2011 | Altman et al. |
| 2011/0208239 | A1 | 8/2011 | Stone et al. |
| 2011/0208240 | A1 | 8/2011 | Stone et al. |
| 2011/0213416 | A1 | 9/2011 | Kaiser |
| 2011/0218625 | A1 | 9/2011 | Berelsman et al. |
| 2011/0224799 | A1 | 9/2011 | Stone |
| 2011/0245868 | A1 | 10/2011 | Teeslink et al. |
| 2011/0264141 | A1 | 10/2011 | Denham et al. |
| 2011/0270278 | A1 | 11/2011 | Overes et al. |
| 2011/0270306 | A1 | 11/2011 | Denham et al. |
| 2011/0295284 | A1 | 12/2011 | Purdue et al. |
| 2012/0004669 | A1 | 1/2012 | Overes et al. |
| 2012/0041485 | A1 | 2/2012 | Kaiser et al. |
| 2012/0041486 | A1 | 2/2012 | Stone et al. |
| 2012/0041496 | A1 | 2/2012 | Walker |
| 2012/0046693 | A1 | 2/2012 | Denham et al. |
| 2012/0053630 | A1 | 3/2012 | Denham et al. |
| 2012/0059417 | A1 | 3/2012 | Norton et al. |
| 2012/0059418 | A1 | 3/2012 | Denham et al. |
| 2012/0059468 | A1 | 3/2012 | Mattern et al. |
| 2012/0089193 | A1 | 4/2012 | Stone et al. |
| 2012/0095470 | A1 | 4/2012 | Kaiser et al. |
| 2012/0109156 | A1 | 5/2012 | Overes et al. |
| 2012/0116409 | A1 | 5/2012 | Stone |
| 2012/0116450 | A1 | 5/2012 | McDevitt et al. |
| 2012/0116452 | A1 | 5/2012 | Stone et al. |
| 2012/0123447 | A1 | 5/2012 | Corrao et al. |
| 2012/0123474 | A1 | 5/2012 | Zajac et al. |
| 2012/0123541 | A1 | 5/2012 | Albertorio et al. |
| 2012/0130492 | A1 | 5/2012 | Eggli et al. |
| 2012/0143215 | A1 | 6/2012 | Corrao et al. |
| 2012/0150223 | A1 | 6/2012 | Manos et al. |
| 2012/0150297 | A1 | 6/2012 | Denham et al. |
| 2012/0165866 | A1 | 6/2012 | Kaiser et al. |
| 2012/0165867 | A1 | 6/2012 | Denham et al. |
| 2012/0165938 | A1 | 6/2012 | Denham et al. |
| 2012/0197271 | A1 | 8/2012 | Astorino et al. |
| 2012/0215257 | A1 | 8/2012 | McDevitt et al. |
| 2012/0245585 | A1 | 9/2012 | Kaiser et al. |
| 2012/0265219 | A1 | 10/2012 | Rushdy et al. |
| 2012/0290003 | A1 | 11/2012 | Dreyfuss |
| 2012/0290004 | A1 | 11/2012 | Lombardo et al. |
| 2012/0296427 | A1 | 11/2012 | Conner et al. |
| 2012/0310245 | A1 | 12/2012 | Hoeppner et al. |
| 2013/0018375 | A1 | 1/2013 | Dell'Oca |
| 2013/0018416 | A1 | 1/2013 | Lombardo et al. |
| 2013/0023928 | A1 | 1/2013 | Dreyfuss |
| 2013/0023929 | A1 | 1/2013 | Sullivan et al. |
| 2013/0023930 | A1 | 1/2013 | Stone et al. |
| 2013/0035698 | A1 | 2/2013 | Stone et al. |
| 2013/0035722 | A1 | 2/2013 | McDevitt et al. |
| 2013/0046341 | A1 | 2/2013 | Stone et al. |
| 2013/0090731 | A1 | 4/2013 | Walker |
| 2013/0103082 | A1 | 4/2013 | Kaiser et al. |
| 2013/0110165 | A1 | 5/2013 | Burkhart et al. |
| 2013/0110251 | A1 | 5/2013 | Metzger et al. |
| 2013/0116730 | A1 | 5/2013 | Denham et al. |
| 2013/0123810 | A1 | 5/2013 | Brown et al. |
| 2013/0123813 | A1 | 5/2013 | Stone et al. |
| 2013/0131722 | A1 | 5/2013 | Marchand et al. |
| 2013/0138123 | A1 | 5/2013 | Stone et al. |
| 2013/0144337 | A1 | 6/2013 | Stone et al. |
| 2013/0144338 | A1 | 6/2013 | Stone et al. |
| 2013/0158601 | A1 | 6/2013 | Stone et al. |
| 2013/0190818 | A1 | 7/2013 | Norton |
| 2013/0190819 | A1 | 7/2013 | Norton |
| 2013/0204276 | A1 | 8/2013 | Stone et al. |
| 2013/0211452 | A1 | 8/2013 | Stone et al. |
| 2013/0237997 | A1 | 9/2013 | Arai et al. |
| 2013/0245761 | A1 | 9/2013 | Conner et al. |
| 2013/0274812 | A1 | 10/2013 | Dell'Oca |
| 2013/0289564 | A1 | 10/2013 | Bernstein et al. |
| 2013/0317621 | A1 | 11/2013 | Metzger et al. |
| 2013/0331848 | A1 | 12/2013 | Kaiser et al. |
| 2014/0046367 | A1 | 2/2014 | Stone et al. |
| 2014/0046368 | A1 | 2/2014 | Kaiser et al. |
| 2014/0067081 | A1 | 3/2014 | Stone |
| 2014/0088655 | A1 | 3/2014 | Stone et al. |
| 2014/0094913 | A1 | 4/2014 | Berelsman et al. |
| 2014/0135835 | A1 | 5/2014 | Stone et al. |
| 2014/0163613 | A1 | 6/2014 | Stone et al. |
| 2014/0163614 | A1 | 6/2014 | Denham et al. |
| 2014/0194927 | A1 | 7/2014 | Kaiser et al. |
| 2014/0200583 | A1 | 7/2014 | Stone et al. |
| 2014/0257378 | A1 | 9/2014 | Norton et al. |
| 2014/0276992 | A1 | 9/2014 | Stone et al. |

(56) References Cited

U.S. PATENT DOCUMENTS

| | | | |
|---|---|---|---|
| 2014/0277447 | A1 | 9/2014 | Berelsman et al. |
| 2014/0324101 | A1 | 10/2014 | Denham et al. |
| 2014/0330311 | A1 | 11/2014 | Denham et al. |
| 2014/0336760 | A1 | 11/2014 | Eggli |
| 2014/0350674 | A1 | 11/2014 | Stone et al. |
| 2015/0012094 | A1 | 1/2015 | Denham et al. |
| 2015/0057757 | A1 | 2/2015 | Metzger et al. |
| 2015/0119890 | A1 | 4/2015 | Kaiser et al. |
| 2015/0127051 | A1 | 5/2015 | Kaiser et al. |
| 2015/0134000 | A1 | 5/2015 | Denham et al. |
| 2015/0173887 | A1 | 6/2015 | Berelsman et al. |
| 2015/0257750 | A1 | 9/2015 | Kaiser et al. |
| 2016/0000483 | A1 | 1/2016 | Stone |
| 2016/0022261 | A1 | 1/2016 | Stone et al. |
| 2016/0058436 | A1 | 3/2016 | Stone et al. |
| 2016/0081789 | A1 | 3/2016 | Denham et al. |
| 2016/0106414 | A1 | 4/2016 | Stone et al. |
| 2016/0128684 | A1 | 5/2016 | Stone et al. |
| 2016/0183935 | A1 | 6/2016 | Stone |
| 2016/0199053 | A1 | 7/2016 | Norton et al. |
| 2016/0213369 | A1 | 7/2016 | Stone et al. |
| 2016/0242760 | A1 | 8/2016 | Kaiser et al. |
| 2017/0014225 | A1 | 1/2017 | Denham et al. |
| 2017/0020507 | A1 | 1/2017 | Denham et al. |
| 2017/0035411 | A1 | 2/2017 | Kaiser et al. |
| 2017/0049557 | A1 | 2/2017 | Denham et al. |
| 2017/0071593 | A1 | 3/2017 | Stone |
| 2017/0071595 | A1 | 3/2017 | Stone et al. |

FOREIGN PATENT DOCUMENTS

| | | | |
|---|---|---|---|
| AU | 4381268 | A | 4/1970 |
| AU | 5850469 | | 1/1971 |
| AU | 5963869 | | 2/1971 |
| AU | 1505470 | | 11/1971 |
| AU | 2223767 | | 5/1973 |
| AU | 3615171 | | 5/1973 |
| AU | 440266 | B2 | 9/1973 |
| AU | 5028569 | | 9/1973 |
| AU | 7110887 | | 10/1987 |
| AU | 639410 | | 11/1989 |
| AU | 1713188 | A | 11/1989 |
| AU | 651929 | | 8/1994 |
| AU | 3877493 | B2 | 8/1994 |
| BE | 1010569 | A6 | 10/1998 |
| CN | 105208970 | A | 12/2015 |
| DE | 2529669 | | 3/1976 |
| DE | 2747312 | | 4/1979 |
| DE | 2818254 | | 10/1979 |
| DE | 2919009 | | 11/1979 |
| DE | 3027138 | | 12/1981 |
| DE | 3225620 | | 2/1983 |
| DE | 3136083 | | 3/1983 |
| DE | 233303 | C | 2/1986 |
| DE | 4127550 | | 2/1993 |
| DE | 4302397 | | 7/1993 |
| DE | 29621340 | | 5/1998 |
| DE | 233303 | C | 3/2000 |
| DE | 19841252 | | 3/2000 |
| DE | 29922088 | U1 | 4/2000 |
| DE | 20207781 | U1 | 8/2002 |
| EP | 19062 | A1 | 11/1980 |
| EP | 0108912 | | 5/1984 |
| EP | 0129422 | | 12/1984 |
| EP | 0129442 | | 12/1984 |
| EP | 0172130 | | 2/1986 |
| EP | 0241240 | | 10/1987 |
| EP | 0241792 | | 10/1987 |
| EP | 0260970 | | 3/1988 |
| EP | 0270704 | | 6/1988 |
| EP | 0282789 | | 9/1988 |
| EP | 0315371 | | 5/1989 |
| EP | 0317406 | | 5/1989 |
| EP | 0340159 | | 11/1989 |
| EP | 0346183 | | 12/1989 |
| EP | 0349173 | | 1/1990 |
| EP | 0374088 | | 6/1990 |
| EP | 0409364 | | 1/1991 |
| EP | 0415915 | | 3/1991 |
| EP | 0440991 | | 8/1991 |
| EP | 440991 | A1 | 8/1991 |
| EP | 0441065 | | 8/1991 |
| EP | 0447065 | A2 | 9/1991 |
| EP | 0451932 | | 10/1991 |
| EP | 0464480 | | 1/1992 |
| EP | 0490417 | | 6/1992 |
| EP | 0497079 | | 8/1992 |
| EP | 0502509 | | 9/1992 |
| EP | 0502698 | | 9/1992 |
| EP | 520177 | | 12/1992 |
| EP | 520177 | A1 | 12/1992 |
| EP | 0546726 | | 6/1993 |
| EP | 0574707 | | 12/1993 |
| EP | 0582514 | | 2/1994 |
| EP | 0591991 | | 4/1994 |
| EP | 0598219 | | 5/1994 |
| EP | 0611551 | A1 | 8/1994 |
| EP | 0627203 | | 12/1994 |
| EP | 0651979 | | 5/1995 |
| EP | 0669110 | | 8/1995 |
| EP | 0686373 | | 12/1995 |
| EP | 0702933 | | 3/1996 |
| EP | 0775473 | | 5/1997 |
| EP | 0913123 | | 5/1999 |
| EP | 0913131 | | 5/1999 |
| EP | 99121106 | | 10/1999 |
| EP | 991210527 | | 10/1999 |
| EP | 0995409 | | 4/2000 |
| EP | 1013229 | | 6/2000 |
| EP | 1093773 | | 4/2001 |
| EP | 1093774 | | 4/2001 |
| EP | 1555945 | | 7/2005 |
| EP | 1741412 | A2 | 1/2007 |
| EP | 1864617 | A2 | 12/2007 |
| EP | 2238944 | A2 | 10/2010 |
| EP | 2544607 | A1 | 1/2013 |
| EP | 2709557 | A1 | 3/2014 |
| EP | 2934379 | A1 | 10/2015 |
| EP | 2434987 | B1 | 6/2016 |
| FR | 2622790 | | 5/1989 |
| FR | 2634373 | A1 | 1/1990 |
| FR | 2655840 | | 6/1991 |
| FR | 2663837 | A1 | 1/1992 |
| FR | 2682867 | | 4/1993 |
| FR | 2687911 | | 9/1993 |
| FR | 2688689 | | 9/1993 |
| FR | 2704140 | | 10/1994 |
| FR | 2717070 | | 9/1995 |
| FR | 2723528 | | 2/1996 |
| FR | 2734709 | A1 | 12/1996 |
| FR | 2744010 | | 8/1997 |
| FR | 2745999 | | 9/1997 |
| FR | 2770764 | | 5/1999 |
| GB | 401677 | | 11/1933 |
| GB | 1413477 | | 11/1975 |
| GB | 1485681 | | 9/1977 |
| GB | 2083751 | | 3/1982 |
| GB | 2118474 | | 11/1983 |
| GB | 2129306 | A | 5/1984 |
| GB | 2227175 | | 7/1990 |
| GB | 2253147 | A | 9/1992 |
| GB | 2312376 | | 10/1997 |
| GB | 2403416 | A | 1/2005 |
| GB | 2454251 | A | 5/2009 |
| JP | 5362911 | | 5/1978 |
| JP | 5362912 | | 5/1978 |
| JP | 5374942 | | 6/1978 |
| JP | 5378230 | | 6/1978 |
| JP | 54166092 | U | 11/1979 |
| JP | 54166093 | U | 11/1979 |
| JP | 54176284 | U | 12/1979 |
| JP | 54178988 | U | 12/1979 |
| JP | 5362911 | A | 7/1987 |
| JP | 62159647 | | 7/1987 |

(56) References Cited

FOREIGN PATENT DOCUMENTS

| | | | |
|---|---|---|---|
| JP | 62159647 | U | 10/1987 |
| JP | 62295657 | | 12/1987 |
| JP | 5269160 | | 10/1993 |
| JP | 5300917 | | 11/1993 |
| JP | 751292 | | 2/1995 |
| JP | 10127672 | A | 5/1998 |
| JP | 10211213 | | 8/1998 |
| JP | 5362912 | B2 | 12/2013 |
| JP | 5374942 | B2 | 12/2013 |
| JP | 5378230 | B2 | 12/2013 |
| RU | 2051647 | C1 | 1/1996 |
| RU | 2076667 | C1 | 4/1997 |
| WO | WO-8300615 | | 3/1983 |
| WO | WO-8603666 | | 7/1986 |
| WO | WO-8701270 | | 3/1987 |
| WO | WO-8901767 | | 3/1989 |
| WO | WO-8909030 | | 10/1989 |
| WO | WO-8910096 | | 11/1989 |
| WO | WO-9008510 | | 8/1990 |
| WO | WO-9203980 | | 3/1992 |
| WO | WO-9314705 | | 8/1993 |
| WO | WO-9315694 | | 8/1993 |
| WO | WO-9502373 | | 1/1995 |
| WO | WO-9503003 | | 2/1995 |
| WO | WO-9529637 | | 11/1995 |
| WO | WO-9532670 | | 12/1995 |
| WO | WO-9609797 | A1 | 4/1996 |
| WO | WO-9629029 | | 9/1996 |
| WO | WO-9737603 | | 10/1997 |
| WO | WO-9812991 | | 4/1998 |
| WO | WO-9812992 | | 4/1998 |
| WO | WO-9822047 | | 5/1998 |
| WO | WO-9822048 | | 5/1998 |
| WO | WO-9901084 | | 1/1999 |
| WO | WO-9912480 | | 3/1999 |
| WO | WO-9937219 | A1 | 7/1999 |
| WO | WO-9944544 | | 9/1999 |
| WO | WO-9952472 | A1 | 10/1999 |
| WO | WO-0004159 | A1 | 1/2000 |
| WO | WO-0040159 | | 7/2000 |
| WO | WO-0139671 | | 6/2001 |
| WO | WO-0236020 | | 5/2002 |
| WO | WO-03005914 | A1 | 1/2003 |
| WO | WO-03071962 | | 9/2003 |
| WO | WO-03077772 | | 9/2003 |
| WO | WO-03092551 | A1 | 11/2003 |
| WO | WO-2004091412 | A1 | 10/2004 |
| WO | WO-2005104992 | A1 | 11/2005 |
| WO | WO-2005122954 | A1 | 12/2005 |
| WO | WO-2006011786 | A1 | 2/2006 |
| WO | WO-2006023661 | A2 | 3/2006 |
| WO | WO-2006055823 | A2 | 5/2006 |
| WO | WO-2007045460 | A2 | 4/2007 |
| WO | WO-2007103562 | A2 | 9/2007 |
| WO | WO-2007109280 | A2 | 9/2007 |
| WO | WO-2007119057 | A1 | 10/2007 |
| WO | WO-2008002550 | A2 | 1/2008 |
| WO | WO-2008015171 | A1 | 2/2008 |
| WO | WO-2008073588 | A2 | 6/2008 |
| WO | WO-2009012021 | A1 | 1/2009 |
| WO | WO-2009083047 | A1 | 7/2009 |
| WO | WO-2009131820 | A1 | 10/2009 |
| WO | WO-2010138832 | A1 | 12/2010 |
| WO | WO-2011112371 | A1 | 9/2011 |
| WO | WO-2011150238 | A1 | 12/2011 |
| WO | WO-2012134999 | A1 | 10/2012 |
| WO | WO-2012158583 | A1 | 11/2012 |
| WO | WO-2013066974 | A1 | 5/2013 |
| WO | WO-2013074525 | A1 | 5/2013 |
| WO | WO-2014/100109 | A1 | 6/2014 |
| WO | WO-2014151766 | A1 | 9/2014 |

OTHER PUBLICATIONS

"JuggerKnot™ Soft Anchor: Arthroscopic and Mini-Open Rotator Cuff Repair Using JuggerKnot™ Soft Anchor—2.9mm with ALLthread™ Knotless Anchor Surgical Technique" brochure, Biomet® Sports Medicine. (2013) 16 pages.

Ziptight™ Fixation System Featuring Zip Loop™ Technology. Ankle Syndesmosis. Surgical Protocol by Timothy Charlton, M.D. Biomet Sports® Medicine brochure. (Jun. 15, 2011) 8 pages.

"U.S. Appl. No. 10/984,624, Final Office Action mailed Jan. 5, 2009", 9 pgs.

"U.S. Appl. No. 10/984,624, Non Final Office Action mailed Jul. 10, 2008", 9 pgs.

"U.S. Appl. No. 10/984,624, Notice of Allowance mailed Jun. 12, 2009", 9 pgs.

"U.S. Appl. No. 10/984,624, Response filed Apr. 1, 2009 to Final Office Action mailed Jan. 5, 2009", 16 pgs.

"U.S. Appl. No. 10/984,624, Response filed Apr. 15, 2008 to Restriction Requirement mailed Mar. 24, 2008", 1 pg.

"U.S. Appl. No. 10/984,624, Response filed Oct. 10, 2008 to Non Final Office Action mailed Jul. 10, 2008", 12 pgs.

"U.S. Appl. No. 10/984,624, Restriction Requirement mailed Mar. 24, 2008", 5 pgs.

"U.S. Appl. No. 11/294,694, Final Office Action mailed Sep. 1, 2010", 14 pgs.

"U.S. Appl. No. 11/294,694, Non Final Office Action mailed Mar. 16, 2010", 19 pgs.

"U.S. Appl. No. 11/294,694, Notice of Allowance mailed Nov. 17, 2010", 4 pgs.

"U.S. Appl. No. 11/294,694, Preliminary Amendment filed Jan. 13, 2010", 9 pgs.

"U.S. Appl. No. 11/294,694, Response filed Jun. 16, 2010 to Non Final Office Action mailed Mar. 16, 2010", 16 pgs.

"U.S. Appl. No. 11/294,694, Response filed Nov. 1, 2010 to Final Office Action mailed Sep. 1, 2010", 10 pgs.

"U.S. Appl. No. 11/294,694, Response filed Dec. 22, 2009 to Restriction Requirement mailed Nov. 25, 2009", 1 pg.

"U.S. Appl. No. 11/294,694, Restriction Requirement mailed Nov. 25, 2009", 9 pgs.

"U.S. Appl. No. 11/347,661, Examiner Interview Summary mailed Sep. 11, 2009", 2 pgs.

"U.S. Appl. No. 11/347,661, Final Office Action mailed Mar. 3, 2009", 15 pgs.

"U.S. Appl. No. 11/347,661, Non Final Office Action mailed Aug. 13, 2009", 19 pgs.

"U.S. Appl. No. 11/347,661, Non Final Office Action mailed Aug. 21, 2008", 11 pgs.

"U.S. Appl. No. 11/347,661, Notice of Allowance mailed Feb. 24, 2010", 8 pgs.

"U.S. Appl. No. 11/347,661, Notice of Allowance mailed May. 5, 2010", 8 pgs.

"U.S. Appl. No. 11/347,661, Response filed May 29, 2008 to Restriction Requirement mailed Apr. 30, 2008", 1 pg.

"U.S. Appl. No. 11/347,661, Response filed Jun. 3, 2009 to Final Office Action mailed Mar. 3, 2009", 19 pgs.

"U.S. Appl. No. 11/347,661, Response filed Nov. 6, 2009 to Non Final Office Action mailed Aug. 13, 2009", 16 pgs.

"U.S. Appl. No. 11/347,661, Response filed Nov. 19, 2008 to Non Final Office Action mailed Aug. 21, 2008", 12 pgs.

"U.S. Appl. No. 11/347,661, Restriction Requirement mailed Apr. 30, 2008", 6 pgs.

"U.S. Appl. No. 11/347,662, Examiner Interview Summary mailed Jun. 24, 2010", 3 pgs.

"U.S. Appl. No. 11/347,662, Examiner Interview Summary mailed Nov. 9, 2009", 3 pgs.

"U.S. Appl. No. 11/347,662, Final Office Action mailed Sep. 16, 2009", 13 pgs.

"U.S. Appl. No. 11/347,662, Final Office Action mailed Oct. 26, 2010", 10 pgs.

(56) References Cited

OTHER PUBLICATIONS

"U.S. Appl. No. 11/347,662, Non Final Office Action mailed Mar. 9, 2009", 11 pgs.
"U.S. Appl. No. 11/347,662, Non Final Office Action mailed May 21, 2010", 19 pgs.
"U.S. Appl. No. 11/347,662, Non Final Office Action mailed Oct. 28, 2008", 13 pgs.
"U.S. Appl. No. 11/347,662, Response filed Jan. 16, 2009 to Non Final Office Action mailed Oct. 28, 2008", 16 pgs.
"U.S. Appl. No. 11/347,662, Response filed Feb. 12, 2010 to Final Office Action mailed Sep. 16, 2009", 21 pgs.
"U.S. Appl. No. 11/347,662, Response filed Jun. 5, 2009 to Non Final Office Action mailed Mar. 9, 2009", 13 pgs.
"U.S. Appl. No. 11/347,662, Response filed Aug. 20, 2010 to Non Final Office Action mailed May 21, 2010", 13 pgs.
"U.S. Appl. No. 11/386,071, Advisory Action mailed Dec. 23, 2010", 3 pgs.
"U.S. Appl. No. 11/386,071, Examiner Interview Summary mailed Jan. 31, 2011", 3 pgs.
"U.S. Appl. No. 11/386,071, Examiner Interview Summary mailed Jul. 21, 2010", 3 pgs.
"U.S. Appl. No. 11/386,071, Final Office Action mailed Oct. 27, 2010", 10 pgs.
"U.S. Appl. No. 11/386,071, Non Final Office Action mailed May 12, 2010", 13 pgs.
"U.S. Appl. No. 11/386,071, Notice of Allowance mailed Jun. 6, 2011", 6 pgs.
"U.S. Appl. No. 11/386,071, Response filed Jan. 26, 2011 to Advisory Action mailed Dec. 23, 2010", 13 pgs.
"U.S. Appl. No. 11/386,071, Response filed Aug. 12, 2010 to Non Final Office Action mailed May 12, 2010", 14 pgs.
"U.S. Appl. No. 11/386,071, Response filed Dec. 15, 2010 to Final Office Action mailed Oct. 27, 2010", 14 pgs.
"U.S. Appl. No. 11/408,282, Final Office Action mailed Dec. 15, 2008", 8 pgs.
"U.S. Appl. No. 11/408,282, Non Final Office Action mailed May 23, 2008", 12 pgs.
"U.S. Appl. No. 11/408,282, Response filed Aug. 21, 2008 to Non Final Office Action mailed May 23, 2008", 10 pgs.
"U.S. Appl. No. 11/504,882, Examiner Interview Summary mailed Sep. 2, 2010", 3 pgs.
"U.S. Appl. No. 11/504,882, Final Office Action mailed Dec. 21, 2010", 7 pgs.
"U.S. Appl. No. 11/504,882, Non Final Office Action mailed Jun. 19, 2014", 11 pgs.
"U.S. Appl. No. 11/504,882, Non Final Office Action mailed Jun. 23, 2010", 8 pgs.
"U.S. Appl. No. 11/504,882, Non Final Office Action mailed Nov. 13, 2013", 13 pgs.
"U.S. Appl. No. 11/504,882, Notice of Allowance mailed Dec. 1, 2014", 9 pgs.
"U.S. Appl. No. 11/504,882, Response filed Feb. 10, 2014 to Non Final Office Action mailed Nov. 13, 2013", 11 pgs.
"U.S. Appl. No. 11/504,882, Response filed Mar. 18, 2011 to Final Office Action mailed Dec. 21, 2010", 11 pgs.
"U.S. Appl. No. 11/504,882, Response filed Sep. 17, 2014 to Non Final Office Action mailed Jun. 19, 2014", 14 pgs.
"U.S. Appl. No. 11/504,882, Response filed Sep. 23, 2010 to Non Final Office Action mailed Jun. 23, 2010", 12 pgs.
"U.S. Appl. No. 11/504,882, Supplemental Notice of Allowability mailed Mar. 12, 2015", 5 pgs.
"U.S. Appl. No. 11/541,505, Non Final Office Action mailed May 19, 2009", 7 pgs.
"U.S. Appl. No. 11/541,505, Notice of Allowance mailed Sep. 18, 2009", 8 pgs.
"U.S. Appl. No. 11/541,505, Response filed Apr. 9, 2009 to Restriction Requirement mailed Mar. 9, 2009", 1 pg.
"U.S. Appl. No. 11/541,505, Response filed Jun. 18, 2009 to Non Final Office Action mailed May 19, 2009", 5 pgs.
"U.S. Appl. No. 11/541,505, Restriction Requirement mailed Mar. 9, 2009", 9 pgs.
"U.S. Appl. No. 11/541,506, Notice of Allowance mailed Jun. 1, 2009", 10 pgs.
"U.S. Appl. No. 11/541,506, Notice of Allowance mailed Jun. 29, 2009", 8 pgs.
"U.S. Appl. No. 11/541,506, Response filed Apr. 9, 2009 to Restriction Requirement mailed Mar. 9, 2009", 1 pg.
"U.S. Appl. No. 11/541,506, Restriction Requirement mailed Mar. 9, 2009", 6 pgs.
"U.S. Appl. No. 11/739,768, Examiner Interview Summary mailed May 11, 2011", 3 pgs.
"U.S. Appl. No. 11/739,768, Examiner Interview Summary mailed Oct. 4, 2011", 3 pgs.
"U.S. Appl. No. 11/739,768, Final Office Action mailed Aug. 22, 2011", 14 pgs.
"U.S. Appl. No. 11/739,768, Non Final Office Action mailed Mar. 4, 2011", 11 pgs.
"U.S. Appl. No. 11/739,768, Notice of Allowance mailed Nov. 15, 2011", 5 pgs.
"U.S. Appl. No. 11/739,768, Response filed Jun. 6, 2011 to Non Final Office Action mailed Mar. 4, 2011", 15 pgs.
"U.S. Appl. No. 11/739,768, Response filed Oct. 26, 2011 to Final Office Action mailed Aug. 22, 2011", 14 pgs.
"U.S. Appl. No. 11/740,035, Final Office Action mailed Aug. 7, 2008", 9 pgs.
"U.S. Appl. No. 11/740,035, Non Final Office Action mailed Jan. 3, 2008", 9 pgs.
"U.S. Appl. No. 11/740,035, Response filed Apr. 3, 2008 to Non Final Office Action mailed Jan. 3, 2008", 6 pgs.
"U.S. Appl. No. 11/784,821, Corrected Notice of Allowance mailed Dec. 24, 2014", 4 pgs.
"U.S. Appl. No. 11/784,821, Examiner Interview Summary mailed Jun. 26, 2014", 3 pgs.
"U.S. Appl. No. 11/784,821, Examiner Interview Summary mailed Nov. 17, 2009", 3 pgs.
"U.S. Appl. No. 11/784,821, Final Office Action mailed Mar. 10, 2010", 11 pgs.
"U.S. Appl. No. 11/784,821, Non Final Office Action mailed Mar. 28, 2014", 14 pgs.
"U.S. Appl. No. 11/784,821, Non Final Office Action mailed Sep. 4, 2009", 12 pgs.
"U.S. Appl. No. 11/784,821, Notice of Allowance mailed Oct. 21, 2014", 10 pgs.
"U.S. Appl. No. 11/784,821, Response filed Jun. 10, 2010 to Final Office Action mailed Mar. 10, 2010", 20 pgs.
"U.S. Appl. No. 11/784,821, Response filed Jun. 15, 2009 to Restriction Requirement mailed May 13, 2009", 2 pgs.
"U.S. Appl. No. 11/784,821, Response filed Jun. 26, 2014 to Non Final Office Action mailed Mar. 28, 2014", 16 pgs.
"U.S. Appl. No. 11/784,821, Response filed Nov. 23, 2009 to Non Final Office Action mailed Sep. 4, 2009", 17 pgs.
"U.S. Appl. No. 11/784,821, Restriction Requirement mailed May 13, 2009", 6 pgs.
"U.S. Appl. No. 11/869,440, Examiner Interview Summary mailed Mar. 25, 2010", 3 pgs.
"U.S. Appl. No. 11/869,440, Non Final Office Action mailed Mar. 1, 2010", 13 pgs.
"U.S. Appl. No. 11/869,440, Notice of Allowance mailed Aug. 19, 2010", 10 pgs.
"U.S. Appl. No. 11/869,440, Response filed Jun. 1, 2010 to Non Final Office Action mailed Mar. 1, 2010", 14 pgs.
"U.S. Appl. No. 11/935,681, Examiner Interview Summary mailed Jul. 19, 2010", 3 pgs.
"U.S. Appl. No. 11/935,681, Non Final Office Action mailed May 24, 2010", 12 pgs.
"U.S. Appl. No. 11/935,681, Notice of Allowance mailed Nov. 8, 2010", 10 pgs.
"U.S. Appl. No. 11/935,681, Response filed Apr. 19, 2010 to Restriction Requirement mailed Mar. 17, 2010", 4 pgs.
"U.S. Appl. No. 11/935,681, Response filed Aug. 24, 2010 to Non Final Office Action mailed May 24, 2010", 13 pgs.

(56) References Cited

OTHER PUBLICATIONS

"U.S. Appl. No. 11/935,681, Restriction Requirement mailed Mar. 17, 2010", 6 pgs.
"U.S. Appl. No. 12/014,340, Examiner Interview Summary mailed Jun. 22, 2010", 3 pgs.
"U.S. Appl. No. 12/014,340, Non Final Office Action mailed May 25, 2010", 12 pgs.
"U.S. Appl. No. 12/014,340, Notice of Allowance mailed Nov. 8, 2010", 9 pgs.
"U.S. Appl. No. 12/014,340, Preliminary Amendment filed May 21, 2010", 11 pgs.
"U.S. Appl. No. 12/014,340, Response filed Apr. 26, 2010 to Restriction Requirement mailed Mar. 25, 2010", 2 pgs.
"U.S. Appl. No. 12/014,340, Response filed Aug. 25, 2010 to Non Final Office Action mailed May 25, 2010", 16 pgs.
"U.S. Appl. No. 12/014,340, Restriction Requirement mailed Mar. 25, 2010", 9 pgs.
"U.S. Appl. No. 12/014,399, Examiner Interview Summary mailed Jun. 23, 2010", 3 pgs.
"U.S. Appl. No. 12/014,399, Non Final Office Action mailed May 26, 2010", 13 pgs.
"U.S. Appl. No. 12/014,399, Notice of Allowance mailed Nov. 12, 2010", 11 pgs.
"U.S. Appl. No. 12/014,399, Preliminary Amendment filed May 25, 2010", 10 pgs.
"U.S. Appl. No. 12/014,399, Response filed May 5, 2010 to Restriction Requirement mailed Apr. 6, 2010", 2 pgs.
"U.S. Appl. No. 12/014,399, Response filed Aug. 25, 2010 to Non Final Office Action mailed May 26, 2010", 14 pgs.
"U.S. Appl. No. 12/014,399, Restriction Requirement mailed Apr. 6, 2010", 9 pgs.
"U.S. Appl. No. 12/029,861, Examiner Interview Summary mailed Jan. 27, 2012", 3 pgs.
"U.S. Appl. No. 12/029,861, Final Office Action mailed Dec. 8, 2011", 11 pgs.
"U.S. Appl. No. 12/029,861, Non Final Office Action mailed Jul. 26, 2011", 11 pgs.
"U.S. Appl. No. 12/029,861, Notice of Allowance mailed Apr. 26, 2012", 5 pgs.
"U.S. Appl. No. 12/029,861, Response filed Jan. 26, 2012 to Final Office Action mailed Dec. 8, 2011", 15 pgs.
"U.S. Appl. No. 12/029,861, Response filed May 6, 2011 to Restriction Requirement mailed Apr. 7, 2011", 10 pgs.
"U.S. Appl. No. 12/029,861, Response filed Jun. 23, 2011 to Restriction Requirement mailed May 24, 2011", 1 pgs.
"U.S. Appl. No. 12/029,861, Response filed Oct. 14, 2011 to Non Final Office Action mailed Jul. 26, 2011", 11 pgs.
"U.S. Appl. No. 12/029,861, Restriction Requirement mailed Apr. 7, 2011", 8 pgs.
"U.S. Appl. No. 12/029,861, Restriction Requirement mailed May 24, 2011", 6 pgs.
"U.S. Appl. No. 12/107,437, Examiner Interview Summary mailed May 10, 2010", 4 pgs.
"U.S. Appl. No. 12/107,437, Non Final Office Action mailed Mar. 17, 2010", 9 pgs.
"U.S. Appl. No. 12/107,437, Preliminary Amendment filed Feb. 23, 2010", 9 pgs.
"U.S. Appl. No. 12/107,437, Response filed Jan. 29, 2010 to Restriction Requirement mailed Jan. 13, 2010", 1 pgs.
"U.S. Appl. No. 12/107,437, Restriction Requirement mailed Jan. 13, 2010", 7 pgs.
"U.S. Appl. No. 12/196,398, Examiner Interview Summary mailed Nov. 8, 2010", 3 pgs.
"U.S. Appl. No. 12/196,398, Notice of Allowance mailed Feb. 3, 2011", 12 pgs.
"U.S. Appl. No. 12/196,398, Preliminary Amendment filed Nov. 10, 2008", 3 pgs.
"U.S. Appl. No. 12/196,398, Preliminary Amendment filed Dec. 1, 2010", 12 pgs.
"U.S. Appl. No. 12/196,398, Preliminary Amendment filed Dec. 9, 2008", 46 pgs.
"U.S. Appl. No. 12/196,398, Response filed Oct. 29, 2010 to Restriction Requirement mailed Sep. 29, 2010", 2 pgs.
"U.S. Appl. No. 12/196,398, Restriction Requirement mailed Sep. 29, 2010", 6 pgs.
"U.S. Appl. No. 12/196,398, Supplemental Notice of Allowability mailed Mar. 9, 2011", 4 pgs.
"U.S. Appl. No. 12/196,398, Supplemental Notice of Allowability mailed Apr. 15, 2011", 4 pgs.
"U.S. Appl. No. 12/196,405, Examiner Interview Summary mailed Jun. 20, 2011", 3 pgs.
"U.S. Appl. No. 12/196,405, Non Final Office Action mailed Apr. 11, 2011", 13 pgs.
"U.S. Appl. No. 12/196,405, Notice of Allowance mailed Oct. 26, 2011", 11 pgs.
"U.S. Appl. No. 12/196,405, Preliminary Amendment filed Nov. 10, 2008", 3 pgs.
"U.S. Appl. No. 12/196,405, Response filed Mar. 16, 2011 to Restriction Requirement mailed Feb. 14, 2011", 1 pgs.
"U.S. Appl. No. 12/196,405, Response filed Jul. 12, 2011 to Non Final Office Action mailed Apr. 11, 2011", 19 pgs.
"U.S. Appl. No. 12/196,405, Restriction Requirement mailed Feb. 14, 2011", 6 pgs.
"U.S. Appl. No. 12/196,405, Supplemental Amendment filed Oct. 3, 2011", 12 pgs.
"U.S. Appl. No. 12/196,407, Examiner Interview Summary mailed Jul. 14, 2011", 3 pgs.
"U.S. Appl. No. 12/196,407, Non Final Office Action mailed May 4, 2011", 11 pgs.
"U.S. Appl. No. 12/196,407, Notice of Allowance mailed Oct. 26, 2011", 10 pgs.
"U.S. Appl. No. 12/196,407, Preliminary Amendment filed Nov. 10, 2008", 3 pgs.
"U.S. Appl. No. 12/196,407, Response filed Apr. 20, 2011 to Restriction Requirement mailed Mar. 22, 2011", 12 pgs.
"U.S. Appl. No. 12/196,407, Response filed Aug. 2, 2011 to Non Final Office Action mailed May 4, 2011", 27 pgs.
"U.S. Appl. No. 12/196,407, Restriction Requirement mailed Mar. 22, 2011", 6 pgs.
"U.S. Appl. No. 12/196,407, Supplemental Response to Non Final Office Action filed Oct. 3, 2011", 18 pgs.
"U.S. Appl. No. 12/196,410, Examiner Interview Summary mailed Jul. 14, 2011", 3 pgs.
"U.S. Appl. No. 12/196,410, Non Final Office Action mailed May 9, 2011", 9 pgs.
"U.S. Appl. No. 12/196,410, Notice of Allowance mailed Oct. 13, 2011", 8 pgs.
"U.S. Appl. No. 12/196,410, Response filed Apr. 20, 2011 to Restriction Requirement mailed Mar. 22, 2011", 13 pgs.
"U.S. Appl. No. 12/196,410, Response filed Aug. 1, 2011 to Non Final Office Action mailed May 9, 2011", 23 pgs.
"U.S. Appl. No. 12/196,410, Restriction Requirement mailed Mar. 22, 2011", 6 pgs.
"U.S. Appl. No. 12/196,410, Supplemental Amendment filed Oct. 3, 2011", 15 pgs.
"U.S. Appl. No. 12/398,548, Examiner Interview Summary mailed Jul. 12, 2011", 3 pgs.
"U.S. Appl. No. 12/398,548, Non Final Office Action mailed Apr. 12, 2011", 7 pgs.
"U.S. Appl. No. 12/398,548, Notice of Allowance mailed Oct. 18, 2011", 7 pgs.
"U.S. Appl. No. 12/398,548, Response filed Jul. 12, 2011 to Non Final Office Action mailed Apr. 12, 2011", 15 pgs.
"U.S. Appl. No. 12/398,548, Supplemental Preliminary Amendment filed Sep. 7, 2010", 11 pgs.
"U.S. Appl. No. 12/419,491, Examiner Interview Summary mailed May 30, 2012", 3 pgs.
"U.S. Appl. No. 12/419,491, Examiner Interview Summary mailed Nov. 29, 2011", 3 pgs.
"U.S. Appl. No. 12/419,491, Final Office Action mailed Apr. 12, 2012", 12 pgs.

(56) References Cited

OTHER PUBLICATIONS

"U.S. Appl. No. 12/419,491, Non Final Office Action mailed Sep. 22, 2011", 12 pgs.
"U.S. Appl. No. 12/419,491, Notice of Allowance mailed Jul. 13, 2012", 10 pgs.
"U.S. Appl. No. 12/419,491, Response filed May 30, 2012 to Final Office Action mailed Apr. 12, 2012", 12 pgs.
"U.S. Appl. No. 12/419,491, Response filed Dec. 9, 2011 to Non Final Office Action mailed Sep. 22, 2011", 17 pgs.
"U.S. Appl. No. 12/474,802, Notice of Allowance mailed Aug. 31, 2011", 13 pgs.
"U.S. Appl. No. 12/474,802, Notice of Allowance mailed Oct. 26, 2011", 4 pgs.
"U.S. Appl. No. 12/474,802, Response filed Mar. 28, 2011 to Restriction Requirement mailed Feb. 24, 2011", 12 pgs.
"U.S. Appl. No. 12/474,802, Restriction Requirement mailed Feb. 24, 2011", 6 pgs.
"U.S. Appl. No. 12/489,168, Examiner Interview Summary mailed Feb. 21, 2012", 3 pgs.
"U.S. Appl. No. 12/489,168, Non Final Office Action mailed Dec. 7, 2011", 10 pgs.
"U.S. Appl. No. 12/489,168, Notice of Allowance mailed Apr. 26, 2012", 8 pgs.
"U.S. Appl. No. 12/489,168, Notice of Allowance mailed Sep. 5, 2012", 8 pgs.
"U.S. Appl. No. 12/489,168, Preliminary Amendment filed Oct. 22, 2009", 3 pgs.
"U.S. Appl. No. 12/489,168, Response filed Feb. 27, 2012 to Non Final Office Action mailed Dec. 7, 2011", 15 pgs.
"U.S. Appl. No. 12/489,168, Response filed Nov. 11, 2011 to Restriction Requirement mailed Oct. 20, 2011", 1 pg.
"U.S. Appl. No. 12/489,168, Restriction Requirement mailed Oct. 20, 2011", 8 pgs.
"U.S. Appl. No. 12/489,181, Examiner Interview Summary mailed Feb. 13, 2012", 3 pgs.
"U.S. Appl. No. 12/489,181, Non Final Office Action mailed Jan. 3, 2012", 9 pgs.
"U.S. Appl. No. 12/489,181, Notice of Allowance mailed May 23, 2012", 9 pgs.
"U.S. Appl. No. 12/489,181, Preliminary Amendment filed Mar. 31, 2011", 10 pgs.
"U.S. Appl. No. 12/489,181, Preliminary Amendment filed Oct. 22, 2009", 3 pgs.
"U.S. Appl. No. 12/489,181, Response filed Mar. 27, 2012 to Non Final Office Action mailed Jan. 3, 2012", 12 pgs.
"U.S. Appl. No. 12/489,181, Response filed Dec. 5, 2011 to Restriction Requirement mailed Nov. 4, 2011", 1 pg.
"U.S. Appl. No. 12/489,181, Restriction Requirement mailed Nov. 4, 2011", 7 pgs.
"U.S. Appl. No. 12/570,854, Examiner Interview Summary mailed Apr. 16, 2012", 3 pgs.
"U.S. Appl. No. 12/570,854, Non Final Office Action mailed Feb. 10, 2012", 8 pgs.
"U.S. Appl. No. 12/570,854, Notice of Allowance mailed Jun. 29, 2012", 10 pgs.
"U.S. Appl. No. 12/570,854, Notice of Allowance mailed Sep. 19, 2012", 6 pgs.
"U.S. Appl. No. 12/570,854, Response filed May 10, 2012 to Non Final Office Action mailed Feb. 10, 2012", 27 pgs.
"U.S. Appl. No. 12/570,854, Response filed Dec. 20, 2011 to Restriction Requirement mailed Dec. 14, 2011", 1 pg.
"U.S. Appl. No. 12/570,854, Restriction Requirement mailed Dec. 14, 2011", 6 pgs.
"U.S. Appl. No. 12/702,067, Non Final Office Action mailed Mar. 5, 2013", 8 pgs.
"U.S. Appl. No. 12/702,067, Notice of Allowance mailed Oct. 7, 2013", 11 pgs.
"U.S. Appl. No. 12/702,067, Preliminary Amendment filed Jan. 11, 2011", 13 pgs.
"U.S. Appl. No. 12/702,067, Response filed Jun. 5, 2013 to Non Final Office Action mailed Mar. 5, 2013", 17 pgs.
"U.S. Appl. No. 12/702,067, Response filed Oct. 2, 2012 to Restriction Requirement mailed Sep. 4, 2012", 1 pg.
"U.S. Appl. No. 12/702,067, Restriction Requirement mailed Sep. 4, 2012", 9 pgs.
"U.S. Appl. No. 12/719,337, Advisory Action mailed Sep. 30, 2014", 4 pgs.
"U.S. Appl. No. 12/719,337, Examiner Interview Summary mailed Apr. 4, 2014", 4 pgs.
"U.S. Appl. No. 12/719,337, Examiner Interview Summary mailed May 14, 2013", 3 pgs.
"U.S. Appl. No. 12/719,337, Examiner Interview Summary mailed Sep. 18, 2014", 3 pgs.
"U.S. Appl. No. 12/719,337, Final Office Action mailed Mar. 12, 2013", 8 pgs.
"U.S. Appl. No. 12/719,337, Final Office Action mailed Jul. 18, 2014", 15 pgs.
"U.S. Appl. No. 12/719,337, Non Final Office Action mailed Jan. 10, 2014", 14 pgs.
"U.S. Appl. No. 12/719,337, Non Final Office Action mailed Sep. 5, 2012", 7 pgs.
"U.S. Appl. No. 12/719,337, Notice of Allowance mailed Mar. 11, 2015", 10 pgs.
"U.S. Appl. No. 12/719,337, Notice of Non-Compliant Amendment mailed May 2, 2014", 3 pgs.
"U.S. Appl. No. 12/719,337, Response filed Apr. 10, 2014 to Non Final Office Action mailed Jan. 10, 2014", 16 pgs.
"U.S. Appl. No. 12/719,337, Response filed May 25, 2012 to Restriction Requirement mailed Apr. 26, 2012", 9 pgs.
"U.S. Appl. No. 12/719,337, Response filed Jun. 5, 2013 to Final Office Action mailed Mar. 12, 2013", 16 pgs.
"U.S. Appl. No. 12/719,337, Response filed Jun. 25, 2014 to Notice of Non-Compliant Amendment mailed May 2, 2014", 10 pgs.
"U.S. Appl. No. 12/719,337, Response filed Sep. 18, 2014 to Final Office Action mailed Jul. 18, 2014", 13 pgs.
"U.S. Appl. No. 12/719,337, Response filed Nov. 28, 2012 to Non Final Office Action mailed Sep. 5, 2012", 14 pgs.
"U.S. Appl. No. 12/719,337, Restriction Requirement mailed Apr. 26, 2012", 8 pgs.
"U.S. Appl. No. 12/788,973, Advisory Action mailed Jan. 23, 2013", 3 pgs.
"U.S. Appl. No. 12/788,973, Advisory Action mailed Dec. 27, 2012", 8 pgs.
"U.S. Appl. No. 12/788,973, Final Office Action mailed Sep. 18, 2012", 16 pgs.
"U.S. Appl. No. 12/788,973, Non Final Office Action mailed May 8, 2012", 12 pgs.
"U.S. Appl. No. 12/788,973, Notice of Allowance mailed Mar. 21, 2013", 6 pgs.
"U.S. Appl. No. 12/788,973, Response filed Jan. 16, 2013 to Advisory Action mailed Dec. 27, 2012", 9 pgs.
"U.S. Appl. No. 12/788,973, Response filed Jul. 19, 2012 to Non Final Office Action mailed May 8, 2012", 21 pgs.
"U.S. Appl. No. 12/788,973, Response filed Dec. 16, 2011 to Restriction Requirement mailed Dec. 6, 2011", 11 pgs.
"U.S. Appl. No. 12/788,973, Response filed Dec. 17, 2012 to Final Office Action mailed Sep. 18, 2012", 15 pgs.
"U.S. Appl. No. 12/788,973, Restriction Requirement mailed Dec. 6, 2011", 9 pgs.
"U.S. Appl. No. 12/788,973, Supplemental Notice of Allowance mailed May 24, 2013", 2 pgs.
"U.S. Appl. No. 12/788,978, Advisory Action mailed Dec. 24, 2013", 4 pgs.
"U.S. Appl. No. 12/788,978, Applicant's Summary of Examiner Interview filed Dec. 12, 2013", 2 pgs.
"U.S. Appl. No. 12/788,978, Corrected Notice of Allowance mailed Apr. 30, 2014", 2 pgs.
"U.S. Appl. No. 12/788,978, Examiner Interview Summary mailed Jan. 28, 2014", 3 pgs.
"U.S. Appl. No. 12/788,978, Examiner Interview Summary mailed Mar. 22, 2013", 3 pgs.

(56) References Cited

OTHER PUBLICATIONS

"U.S. Appl. No. 12/788,978, Examiner Interview Summary mailed Sep. 11, 2012", 3 pgs.
"U.S. Appl. No. 12/788,978, Examiner Interview Summary mailed Oct. 29, 2013", 4 pgs.
"U.S. Appl. No. 12/788,978, Examiner Interview Summary mailed Dec. 16, 2013", 3 pgs.
"U.S. Appl. No. 12/788,978, Examiner Interview Summary mailed Dec. 27, 2012", 3 pgs.
"U.S. Appl. No. 12/788,978, Final Office Action mailed Aug. 20, 2013", 17 pgs.
"U.S. Appl. No. 12/788,978, Final Office Action mailed Nov. 2, 2012", 14 pgs.
"U.S. Appl. No. 12/788,978, Non Final Office Action mailed Jan. 11, 2013", 16 pgs.
"U.S. Appl. No. 12/788,978, Non Final Office Action mailed Jul. 13, 2012", 17 pgs.
"U.S. Appl. No. 12/788,978, Notice of Allowance mailed Jan. 24, 2014", 9 pgs.
"U.S. Appl. No. 12/788,978, Notice of Non-Compliant Amendment mailed Jun. 6, 2013", 3 pgs.
"U.S. Appl. No. 12/788,978, Response filed Jan. 2, 2013 to Final Office Action mailed Nov. 2, 2012", 13 pgs.
"U.S. Appl. No. 12/788,978, Response filed Jan. 20, 2014 to Advisory Action mailed Dec. 24, 2013", 4 pgs.
"U.S. Appl. No. 12/788,978, Response filed Apr. 8, 2013 to Non Final Office Action mailed Jan. 11, 2013", 16 pgs.
"U.S. Appl. No. 12/788,978, Response filed May 21, 2012 to Restriction Requirement mailed Apr. 20, 2012", 12 pgs.
"U.S. Appl. No. 12/788,978, Response filed Jul. 3, 2013 to Notice of Non-Compliant Amendment mailed Jun. 6, 2013", 17 pgs.
"U.S. Appl. No. 12/788,978, Response filed Oct. 5, 2012 to Non Final Office Action mailed Jul. 13, 2012", 20 pgs.
"U.S. Appl. No. 12/788,978, Response filed Nov. 20, 2013 to Final Office Action mailed Aug. 20, 2013", 15 pgs.
"U.S. Appl. No. 12/788,978, Restriction Requirement mailed Apr. 20, 2012", 8 pgs.
"U.S. Appl. No. 12/828,977, Examiner Interview Summary mailed Jul. 9, 2012", 3 pgs.
"U.S. Appl. No. 12/828,977, Non Final Office Action mailed May 3, 2012", 9 pgs.
"U.S. Appl. No. 12/828,977, Notice of Allowance mailed Sep. 5, 2012", 9 pgs.
"U.S. Appl. No. 12/828,977, Preliminary Amendment filed Jul. 19, 2011", 10 pgs.
"U.S. Appl. No. 12/828,977, Response filed Mar. 14, 2012 to Restriction Requirement mailed Feb. 13, 2012", 9 pgs.
"U.S. Appl. No. 12/828,977, Response filed Jul. 25, 2012 to Non Final Office Action mailed May 3, 2012", 11 pgs.
"U.S. Appl. No. 12/828,977, Restriction Requirement mailed Feb. 13, 2012", 7 pgs.
"U.S. Appl. No. 12/915,962, Examiner Interview Summary mailed Jul. 25, 2012", 3 pgs.
"U.S. Appl. No. 12/915,962, Non Final Office Action mailed May 7, 2012", 11 pgs.
"U.S. Appl. No. 12/915,962, Non Final Office Action mailed Oct. 15, 2012", 9 pgs.
"U.S. Appl. No. 12/915,962, Notice of Allowance mailed Jun. 10, 2013", 12 pgs.
"U.S. Appl. No. 12/915,962, Response filed Jan. 10, 2013 to Non Final Office Action mailed Oct. 15, 2012", 21 pgs.
"U.S. Appl. No. 12/915,962, Response filed Mar. 16, 2012 to Restriction Requirement mailed Feb. 15, 2012", 15 pgs.
"U.S. Appl. No. 12/915,962, Response filed Aug. 7, 2012 to Non Final Office Action mailed May 7, 2012", 26 pgs.
"U.S. Appl. No. 12/915,962, Restriction Requirement mailed Feb. 15, 2012", 8 pgs.
"U.S. Appl. No. 12/938,902, Examiner Interview Summary mailed Dec. 3, 2012", 3 pgs.
"U.S. Appl. No. 12/976,328, Examiner Interview Summary mailed Feb. 13, 2012", 3 pgs.
"U.S. Appl. No. 12/976,328, Non Final Office Action mailed Dec. 15, 2011", 13 pgs.
"U.S. Appl. No. 12/976,328, Notice of Allowance mailed Apr. 30, 2012", 9 pgs.
"U.S. Appl. No. 12/976,328, Response filed Mar. 2, 2012 to Non Final Office Action mailed Dec. 15, 2011", 15 pgs.
"U.S. Appl. No. 13/045,689, Examiner Interview Summary mailed May 14, 2012", 3 pgs.
"U.S. Appl. No. 13/045,689, Non Final Office Action mailed Mar. 20, 2012", 11 pgs.
"U.S. Appl. No. 13/045,689, Notice of Allowance mailed Aug. 10, 2012", 10 pgs.
"U.S. Appl. No. 13/045,689, Notice of Allowance mailed Sep. 24, 2012", 7 pgs.
"U.S. Appl. No. 13/045,689, Response filed Jan. 30, 2012 to Restriction Requirement mailed Dec. 29, 2011", 13 pgs.
"U.S. Appl. No. 13/045,689, Response filed Jun. 8, 2012 to Non Final Office Action mailed Mar. 20, 2012", 15 pgs.
"U.S. Appl. No. 13/045,689, Restriction Requirement mailed Dec. 29, 2011", 6 pgs.
"U.S. Appl. No. 13/045,691, Examiner Interview Summary mailed May 14, 2012", 3 pgs.
"U.S. Appl. No. 13/045,691, Non Final Office Action mailed Mar. 20, 2012", 12 pgs.
"U.S. Appl. No. 13/045,691, Notice of Allowance mailed Jun. 19, 2012", 10 pgs.
"U.S. Appl. No. 13/045,691, Response filed Feb. 9, 2012 to Restriction Requirement mailed Jan. 9, 2012", 1 pg.
"U.S. Appl. No. 13/045,691, Response filed Jun. 8, 2012 to Non Final Office Action mailed Mar. 20, 2012", 17 pgs.
"U.S. Appl. No. 13/045,691, Restriction Requirement mailed Jan. 9, 2012", 6 pgs.
"U.S. Appl. No. 13/071,563, Final Office Action mailed May 23, 2014", 13 pgs.
"U.S. Appl. No. 13/071,563, Non Final Office Action mailed Oct. 23, 2013", 18 pgs.
"U.S. Appl. No. 13/071,563, Notice of Allowance mailed Aug. 15, 2014", 7 pgs.
"U.S. Appl. No. 13/071,563, Preliminary Amendment filed May 1, 2012", 8 pgs.
"U.S. Appl. No. 13/071,563, Preliminary Amendment filed Dec. 6, 2011", 7 pgs.
"U.S. Appl. No. 13/071,563, Response filed Jan. 21, 2014 to Non Final Office Action mailed Oct. 23, 2013", 13 pgs.
"U.S. Appl. No. 13/071,563, Response filed Jul. 23, 2014 to Final Office Action mailed May 23, 2014", 14 pgs.
"U.S. Appl. No. 13/071,563, Response filed Sep. 19, 2013 to Restriction Requirement mailed Aug. 19, 2013", 11 pgs.
"U.S. Appl. No. 13/071,563, Restriction Requirement mailed Aug. 19, 2013", 7 pgs.
"U.S. Appl. No. 13/098,897, Examiner Interview Summary mailed Nov. 27, 2012", 3 pgs.
"U.S. Appl. No. 13/098,897, Non Final Office Action mailed Sep. 21, 2012", 9 pgs.
"U.S. Appl. No. 13/098,897, Notice of Allowance mailed Jun. 11, 2013", 13 pgs.
"U.S. Appl. No. 13/098,897, Response filed Aug. 30, 2012 to Restriction Requirement mailed Jul. 30, 2012", 16 pgs.
"U.S. Appl. No. 13/098,897, Response filed Dec. 18, 2012 to Non Final Office Action mailed Sep. 21, 2012", 21 pgs.
"U.S. Appl. No. 13/098,897, Restriction Requirement mailed Jul. 30, 2012", 8 pgs.
"U.S. Appl. No. 13/098,927, Advisory Action mailed Aug. 8, 2013", 3 pgs.
"U.S. Appl. No. 13/098,927, Applicant's Summary of Examiner Interview filed Sep. 23, 2013", 12 pgs.
"U.S. Appl. No. 13/098,927, Examiner Interview Summary mailed Jun. 28, 2013", 3 pgs.
"U.S. Appl. No. 13/098,927, Examiner Interview Summary mailed Sep. 20, 2013", 3 pgs.

(56) References Cited

OTHER PUBLICATIONS

"U.S. Appl. No. 13/098,927, Final Office Action mailed May 22, 2013", 10 pgs.
"U.S. Appl. No. 13/098,927, Non Final Office Action mailed Sep. 24, 2012", 12 pgs.
"U.S. Appl. No. 13/098,927, Notice of Allowance mailed Jan. 8, 2014", 5 pgs.
"U.S. Appl. No. 13/098,927, Notice of Allowance mailed Sep. 26, 2013", 14 pgs.
"U.S. Appl. No. 13/098,927, Response filed Jul. 22, 2015 to Final Office Action mailed May 22, 2013", 17 pgs.
"U.S. Appl. No. 13/098,927, Response filed Aug. 27, 2012 to Restriction Requirement mailed Jul. 25, 2012", 14 pgs.
"U.S. Appl. No. 13/098,927, Response filed Dec. 21, 2012 to Non Final Office Action mailed Sep. 24, 2012", 21 pgs.
"U.S. Appl. No. 13/098,927, Restriction Requirement mailed Jul. 25, 2012", 8 pgs.
"U.S. Appl. No. 13/102,182, Notice of Allowance mailed Mar. 22, 2012", 10 pgs.
"U.S. Appl. No. 13/109,667, Advisory Action mailed Feb. 4, 2014", 4 pgs.
"U.S. Appl. No. 13/109,667, Examiner Interview Summary mailed Dec. 20, 2013", 3 pgs.
"U.S. Appl. No. 13/109,667, Final Office Action mailed Oct. 11, 2013", 19 pgs.
"U.S. Appl. No. 13/109,667, Non Final Office Action mailed May 21, 2013", 21 pgs.
"U.S. Appl. No. 13/109,667, Notice of Allowance mailed Feb. 18, 2014", 10 pgs.
"U.S. Appl. No. 13/109,667, Response filed Jan. 13, 2014 to Final Office Action mailed Oct. 11, 2013", 20 pgs.
"U.S. Appl. No. 13/109,667, Response filed May 2, 2013 to Restriction Requirement mailed Apr. 2, 2013", 1 pg.
"U.S. Appl. No. 13/109,667, Response filed Aug. 21, 2013 to Non Final Office Action mailed May 21, 2013", 27 pgs.
"U.S. Appl. No. 13/109,667, Restriction Requirement mailed Apr. 2, 2013", 8 pgs.
"U.S. Appl. No. 13/109,667, Supplemental Notice of Allowability mailed Jun. 12, 2014", 3 pgs.
"U.S. Appl. No. 13/109,667, Supplemental Notice of Allowance mailed May 28, 2014", 2 pgs.
"U.S. Appl. No. 13/109,667, Supplemental Preliminary Amendment filed Feb. 4, 2014", 16 pgs.
"U.S. Appl. No. 13/109,672, 312 Amendment filed Jan. 15, 2015", 3 pgs.
"U.S. Appl. No. 13/109,672, Non Final Office Action mailed May 15, 2014", 10 pgs.
"U.S. Appl. No. 13/109,672, Notice of Allowance mailed Feb. 3, 2015", 2 pgs.
"U.S. Appl. No. 13/109,672, Notice of Allowance mailed Sep. 29, 2014", 9 pgs.
"U.S. Appl. No. 13/109,672, PTO Response to Rule 312 Communication mailed Jan. 27, 2015", 2 pgs.
"U.S. Appl. No. 13/109,672, Response filed Apr. 14, 2014 to Restriction Requirement mailed Feb. 14, 2014", 15 pgs.
"U.S. Appl. No. 13/109,672, Response filed Aug. 15, 2014 to Non Final Office Action mailed May 15, 2014", 20 pgs.
"U.S. Appl. No. 13/109,672, Response filed Nov. 4, 2013 to Restriction Requirement mailed Oct. 2, 2013", 10 pgs.
"U.S. Appl. No. 13/109,672, Restriction Requirement mailed Feb. 14, 2014", 7 pgs.
"U.S. Appl. No. 13/109,672, Restriction Requirement mailed Oct. 2, 2013", 7 pgs.
"U.S. Appl. No. 13/111,564, Corrected Notice of Allowance mailed Oct. 9, 2013", 2 pgs.
"U.S. Appl. No. 13/111,564, Examiner Interview Summary mailed Jun. 18, 2013", 3 pgs.
"U.S. Appl. No. 13/111,564, Non Final Office Action mailed Mar. 18, 2013", 8 pgs.
"U.S. Appl. No. 13/111,564, Notice of Allowance mailed Jun. 28, 2013", 12 pgs.
"U.S. Appl. No. 13/111,564, Response filed Feb. 4, 2013 to Restriction Requirement mailed Jan. 3, 2013", 20 pgs.
"U.S. Appl. No. 13/111,564, Response filed Jun. 18, 2013 to Non Final Office Action mailed Mar. 18, 2013", 25 pgs.
"U.S. Appl. No. 13/111,564, Restriction Requirement mailed Jan. 3, 2013", 5 pgs.
"U.S. Appl. No. 13/177,153, Final Office Action mailed May 28, 2013", 11 pgs.
"U.S. Appl. No. 13/177,153, Non Final Office Action mailed Oct. 2, 2012", 11 pgs.
"U.S. Appl. No. 13/177,153, Notice of Allowance mailed Jan. 7, 2014", 4 pgs.
"U.S. Appl. No. 13/177,153, Notice of Allowance mailed Sep. 17, 2013", 13 pgs.
"U.S. Appl. No. 13/177,153, Response filed Aug. 28, 2013 to Final Office Action mailed May 28, 2013", 19 pgs.
"U.S. Appl. No. 13/177,153, Response filed Sep. 4, 2012 to Restriction Requirement mailed Aug. 2, 2012", 15 pgs.
"U.S. Appl. No. 13/177,153, Response filed Dec. 20, 2012 to Non Final Office Action mailed Oct. 2, 2012", 16 pgs.
"U.S. Appl. No. 13/177,153, Restriction Requirement mailed Aug. 2, 2012", 9 pgs.
"U.S. Appl. No. 13/181,729, Examiner Interview Summary mailed May 9, 2013", 3 pgs.
"U.S. Appl. No. 13/181,729, Final Office Action mailed Mar. 13, 2013", 14 pgs.
"U.S. Appl. No. 13/181,729, Non Final Office Action mailed Oct. 2, 2012", 7 pgs.
"U.S. Appl. No. 13/181,729, Notice of Allowance mailed May 23, 2013", 9 pgs.
"U.S. Appl. No. 13/181,729, Response filed May 13, 2013 to Final Office Action mailed Mar. 13, 2013", 13 pgs.
"U.S. Appl. No. 13/181,729, Response filed Dec. 20, 2012 to Non Final Office Action mailed Oct. 2, 2012", 15 pgs.
"U.S. Appl. No. 13/269,097, Final Office Action mailed Aug. 8, 2013", 7 pgs.
"U.S. Appl. No. 13/269,097, Non Final Office Action mailed Feb. 12, 2013", 10 pgs.
"U.S. Appl. No. 13/269,097, Notice of Allowance mailed Feb. 3, 2014", 5 pgs.
"U.S. Appl. No. 13/269,097, Notice of Allowance mailed Oct. 21, 2013", 9 pgs.
"U.S. Appl. No. 13/269,097, Response filed May 13, 2013 to Non Final Office Action mailed Feb. 12, 2013", 17 pgs.
"U.S. Appl. No. 13/269,097, Response filed Oct. 8, 2013 to Final Office Action mailed Aug. 8, 2013", 12 pgs.
"U.S. Appl. No. 13/269,097, Response filed Nov. 13, 2012 to Restriction Requirement mailed Oct. 17, 2012", 1 pg.
"U.S. Appl. No. 13/269,097, Restriction Requirement mailed Oct. 17, 2012", 8 pgs.
"U.S. Appl. No. 13/278,341, Notice of Allowance mailed Jun. 18, 2013", 10 pgs.
"U.S. Appl. No. 13/278,341, Response filed Mar. 8, 2013 to Restriction Requirement mailed Feb. 11, 2013", 1 pg.
"U.S. Appl. No. 13/278,341, Restriction Requirement mailed Feb. 11, 2013", 6 pgs.
"U.S. Appl. No. 13/281,009, Non Final Office Action mailed Jun. 2, 2015", 9 pgs.
"U.S. Appl. No. 13/281,009, Notice of Allowance mailed Feb. 24, 2016", 9 pgs.
"U.S. Appl. No. 13/281,009, Notice of Allowance mailed Oct. 29, 2015", 8 pgs.
"U.S. Appl. No. 13/281,009, Response filed Sep. 2, 2015 to Non Final Office Action mailed Jun. 2, 2015", 13 pgs.
"U.S. Appl. No. 13/281,009, Restriction Requirement mailed Feb. 11, 2015", 6 pgs.
"U.S. Appl. No. 13/288,459, Examiner Interview Summary mailed Feb. 6, 2015", 3 pgs.
"U.S. Appl. No. 13/288,459, Non Final Office Action mailed Jun. 24, 2015", 10 pgs.

(56) References Cited

OTHER PUBLICATIONS

"U.S. Appl. No. 13/288,459, Non Final Office Action mailed Nov. 4, 2014", 15 pgs.
"U.S. Appl. No. 13/288,459, Notice of Allowance mailed Jan. 11, 2016", 13 pgs.
"U.S. Appl. No. 13/288,459, Response filed Mar. 3, 2015 to Non Final Office Action mailed Nov. 4, 2014", 16 pgs.
"U.S. Appl. No. 13/288,459, Response filed Oct. 13, 2014 to Restriction Requirement mailed Aug. 11, 2014", 15 pgs.
"U.S. Appl. No. 13/288,459, Response filed Oct. 23, 2015 to Non Final Office Action mailed Jun. 24, 2015", 14 pgs.
"U.S. Appl. No. 13/288,459, Restriction Requirement mailed Aug. 11, 2014", 9 pgs.
"U.S. Appl. No. 13/288,463, Examiner Interview Summary mailed Jun. 3, 2014", 3 pgs.
"U.S. Appl. No. 13/288,463, Non Final Office Action mailed Feb. 24, 2014", 13 pgs.
"U.S. Appl. No. 13/288,463, Notice of Allowance mailed Aug. 27, 2014", 9 pgs.
"U.S. Appl. No. 13/288,463, Response filed May 27, 2014 to Non Final Office Action mailed Feb. 24, 2014", 15 pgs.
"U.S. Appl. No. 13/288,463, Supplemental Notice of Allowability mailed Dec. 8, 2014", 5 pgs.
"U.S. Appl. No. 13/288,463, Supplemental Notice of Allowability mailed Dec. 19, 2014", 5 pgs.
"U.S. Appl. No. 13/293,825, Notice of Allowability mailed Jun. 22, 2015", 7 pgs.
"U.S. Appl. No. 13/293,825, Notice of Allowance mailed May 19, 2015", 9 pgs.
"U.S. Appl. No. 13/293,825, Response filed Apr. 15, 2015 to Restriction Requirement mailed Feb. 12, 2015", 17 pgs.
"U.S. Appl. No. 13/293,825, Restriction Requirement mailed Feb. 12, 2015", 9 pgs.
"U.S. Appl. No. 13/295,126, Non Final Office Action mailed May 19, 2015", 9 pgs.
"U.S. Appl. No. 13/295,126, Notice of Allowance mailed Oct. 22, 2015", 9 pgs.
"U.S. Appl. No. 13/295,126, Response filed Apr. 13, 2015 to Restriction Requirement mailed Feb. 12, 2015", 1 pgs.
"U.S. Appl. No. 13/295,126, Response filed Aug. 17, 2015 to Non Final Office Action mailed May 19, 2015", 21 pgs.
"U.S. Appl. No. 13/295,126, Restriction Requirement mailed Feb. 12, 2015", 9 pgs.
"U.S. Appl. No. 13/311,936, Examiner Interview Summary mailed Feb. 12, 2015", 2 pgs.
"U.S. Appl. No. 13/311,936, Non Final Office Action mailed Feb. 9, 2015", 13 pgs.
"U.S. Appl. No. 13/311,936, Non Final Office Action mailed Oct. 19, 2015", 8 pgs.
"U.S. Appl. No. 13/311,936, Notice of Allowance mailed Mar. 29, 2016", 8 pgs.
"U.S. Appl. No. 13/311,936, Response filed Jan. 18, 2016 to Non Final Office Action mailed Oct. 19, 2015", 8 pgs.
"U.S. Appl. No. 13/311,936, Response filed Jun. 9, 2015 to Non Final Office Action mailed Feb. 9, 2015", 12 pgs.
"U.S. Appl. No. 13/311,936, Response filed Oct. 3, 2014 to Restriction Requirement mailed Aug. 5, 2014", 10 pgs.
"U.S. Appl. No. 13/311,936, Restriction Requirement mailed Aug. 5, 2014", 7 pgs.
"U.S. Appl. No. 13/350,985, Final Office Action mailed Apr. 16, 2015", 8 pgs.
"U.S. Appl. No. 13/350,985, Non Final Office Action mailed Dec. 15, 2014", 8 pgs.
"U.S. Appl. No. 13/350,985, Notice of Allowance mailed Jul. 27, 2015", 5 pgs.
"U.S. Appl. No. 13/350,985, Response filed Mar. 13, 2015 to Non Final Office Action mailed Dec. 15, 2014", 10 pgs.
"U.S. Appl. No. 13/350,985, Response filed Jul. 9, 2015 to Final Office Action mailed Apr. 16, 2015", 8 pgs.
"U.S. Appl. No. 13/350,985, Response filed Dec. 2, 2014 to Restriction Requirement mailed Oct. 2, 2014", 9 pgs.
"U.S. Appl. No. 13/350,985, Restriction Requirement mailed Oct. 2, 2014", 6 pgs.
"U.S. Appl. No. 13/399,125, Corrected Notice of Allowance mailed Aug. 28, 2014", 2 pgs.
"U.S. Appl. No. 13/399,125, Examiner Interview Summary mailed May 17, 2013", 3 pgs.
"U.S. Appl. No. 13/399,125, Final Office Action mailed Mar. 20, 2013", 12 pgs.
"U.S. Appl. No. 13/399,125, Non Final Office Action mailed Oct. 24, 2012", 12 pgs.
"U.S. Appl. No. 13/399,125, Notice of Allowance mailed May 16, 2014", 8 pgs.
"U.S. Appl. No. 13/399,125, Response filed Jan. 10, 2013 to Non Final Office Action mailed Oct. 24, 2012", 15 pgs.
"U.S. Appl. No. 13/399,125, Response filed May 20, 2013 to Final Office Action mailed Mar. 20, 2013", 14 pgs.
"U.S. Appl. No. 13/412,105, Advisory Action mailed Feb. 24, 2014", 3 pgs.
"U.S. Appl. No. 13/412,105, Examiner Interview Summary mailed Feb. 6, 2014", 3 pgs.
"U.S. Appl. No. 13/412,105, Examiner Interview Summary mailed Oct. 11, 2013", 3 pgs.
"U.S. Appl. No. 13/412,105, Final Office Action mailed Dec. 13, 2013", 9 pgs.
"U.S. Appl. No. 13/412,105, Non Final Office Action mailed Jul. 15, 2013", 10 pgs.
"U.S. Appl. No. 13/412,105, Notice of Allowance mailed Aug. 18, 2014", 9 pgs.
"U.S. Appl. No. 13/412,105, Response filed Feb. 10, 2014 to Final Office Action mailed Dec. 13, 2013", 14 pgs.
"U.S. Appl. No. 13/412,105, Response filed Mar. 13, 2014 to Advisory Action mailed Feb. 24, 2014", 19 pgs.
"U.S. Appl. No. 13/412,105, Response filed May 6, 2013 to Restriction Requirement mailed Apr. 5, 2013", 9 pgs.
"U.S. Appl. No. 13/412,105, Response filed Oct. 14, 2013 to Non Final Office Action mailed Jul. 15, 2013", 13 pgs.
"U.S. Appl. No. 13/412,105, Restriction Requirement mailed Apr. 5, 2013", 9 pgs.
"U.S. Appl. No. 13/412,116, Corrected Notice of Allowance mailed Jun. 2, 2014", 2 pgs.
"U.S. Appl. No. 13/412,116, Examiner Interview Summary mailed Dec. 13, 2013", 3 pgs.
"U.S. Appl. No. 13/412,116, Non Final Office Action mailed Sep. 11, 2013", 9 pgs.
"U.S. Appl. No. 13/412,116, Notice of Allowance mailed Feb. 19, 2014", 9 pgs.
"U.S. Appl. No. 13/412,116, Response filed Jul. 3, 2013 to Restriction Requirement mailed Jun. 19, 2013", 1 pg.
"U.S. Appl. No. 13/412,116, Response filed Dec. 11, 2013 to Non Final Office Action mailed Sep. 11, 2013", 11 pgs.
"U.S. Appl. No. 13/412,116, Restriction Requirement mailed Jun. 19, 2013", 9 pgs.
"U.S. Appl. No. 13/412,127, Examiner Interview Summary mailed Nov. 5, 2013", 3 pgs.
"U.S. Appl. No. 13/412,127, Non Final Office Action mailed Aug. 7, 2013", 15 pgs.
"U.S. Appl. No. 13/412,127, Notice of Allowance mailed Dec. 24, 2013", 10 pgs.
"U.S. Appl. No. 13/412,127, Response filed May 23, 2013 to Restriction Requirement mailed Apr. 24, 2013", 2 pgs.
"U.S. Appl. No. 13/412,127, Response filed Nov. 5, 2013 to Non Final Office Action mailed Aug. 7, 2013", 16 pgs.
"U.S. Appl. No. 13/412,127, Restriction Requirement mailed Apr. 24, 2013", 10 pgs.
"U.S. Appl. No. 13/587,374, Final Office Action mailed Nov. 6, 2013", 9 pgs.
"U.S. Appl. No. 13/587,374, Non Final Office Action mailed Jul. 17, 2013", 8 pgs.
"U.S. Appl. No. 13/587,374, Notice of Allowance mailed Feb. 28, 2014", 5 pgs.

(56) References Cited

OTHER PUBLICATIONS

"U.S. Appl. No. 13/587,374, Preliminary Amendment filed Jun. 21, 2013", 9 pgs.
"U.S. Appl. No. 13/587,374, Response filed Jan. 24, 2014 to Final Office Action mailed Nov. 6, 2013", 15 pgs.
"U.S. Appl. No. 13/587,374, Response filed Oct. 14, 2013 to Non Final Office Action mailed Jul. 17, 2013", 14 pgs.
"U.S. Appl. No. 13/625,413, Final Office Action mailed Oct. 30, 2015", 8 pgs.
"U.S. Appl. No. 13/625,413, Non Final Office Action mailed Jun. 8, 2015", 11 pgs.
"U.S. Appl. No. 13/625,413, Notice of Allowance mailed Apr. 1, 2016", 8 pgs.
"U.S. Appl. No. 13/625,413, Notice of Allowance mailed Dec. 11, 2015", 9 pgs.
"U.S. Appl. No. 13/625,413, Response filed May 11, 2015 to Restriction Requirement mailed Mar. 10, 2015", 1 pg.
"U.S. Appl. No. 13/625,413, Response filed Sep. 8, 2015 to Non Final Office Action mailed Jun. 8, 2015", 16 pgs.
"U.S. Appl. No. 13/625,413, Response filed Dec. 1, 2015 to Final Office Action mailed Oct. 30, 2015", 9 pgs.
"U.S. Appl. No. 13/625,413, Restriction Requirement mailed Mar. 10, 2015", 7 pgs.
"U.S. Appl. No. 13/645,964, Advisory Action mailed Feb. 4, 2016", 2 pgs.
"U.S. Appl. No. 13/645,964, Final Office Action mailed Oct. 6, 2015", 17 pgs.
"U.S. Appl. No. 13/645,964, Non Final Office Action mailed Mar. 15, 2016", 15 pgs.
"U.S. Appl. No. 13/645,964, Non Final Office Action mailed Mar. 17, 2015", 15 pgs.
"U.S. Appl. No. 13/645,964, Response filed Jul. 17, 2015 to Non Final Office Action mailed Mar. 17, 2015", 17 pgs.
"U.S. Appl. No. 13/645,964, Response filed Dec. 4, 2015 to Final Office Action mailed Oct. 6, 2015", 14 pgs.
"U.S. Appl. No. 13/656,821, Notice of Allowance mailed Jun. 18, 2015", 11 pgs.
"U.S. Appl. No. 13/656,821, Response filed May 11, 2015 to Restriction Requirement mailed Mar. 10, 2015", 1 pg.
"U.S. Appl. No. 13/656,821, Restriction Requirement mailed Mar. 10, 2015", 6 pgs.
"U.S. Appl. No. 13/720,648, Final Office Action mailed Nov. 16, 2015", 7 pgs.
"U.S. Appl. No. 13/720,648, Non Final Office Action mailed Jun. 10, 2015", 11 pgs.
"U.S. Appl. No. 13/720,648, Notice of Allowance mailed Feb. 5, 2016", 11 pgs.
"U.S. Appl. No. 13/720,648, Response filed Jan. 13, 2016 to Final Office Action mailed Nov. 16, 2015", 9 pgs.
"U.S. Appl. No. 13/720,648, Response filed May 11, 2015 to Restriction Requirement mailed Mar. 10, 2015", 8 pgs.
"U.S. Appl. No. 13/720,648, Response filed Oct. 9, 2015 to Non Final Office Action mailed Jun. 10, 2015", 12 pgs.
"U.S. Appl. No. 13/720,648, Restriction Requirement mailed Mar. 10, 2015", 8 pgs.
"U.S. Appl. No. 13/721,970, Notice of Allowance mailed Aug. 12, 2013", 13 pgs.
"U.S. Appl. No. 13/721,970, Preliminary Amendment filed Mar. 15, 2013", 13 pgs.
"U.S. Appl. No. 13/721,970, Response filed May 8, 2013 to Restriction Requirement mailed Apr. 11, 2013", 1 pgs.
"U.S. Appl. No. 13/721,970, Restriction Requirement mailed Apr. 11, 2013", 6 pgs.
"U.S. Appl. No. 13/751,846, Final Office Action mailed Nov. 17, 2015", 9 pgs.
"U.S. Appl. No. 13/751,846, Non Final Office Action mailed Jun. 15, 2015", 10 pgs.
"U.S. Appl. No. 13/751,846, Notice of Allowance mailed Mar. 16, 2016", 11 pgs.
"U.S. Appl. No. 13/751,846, Response filed Feb. 5, 2016 to Final Office Action mailed Nov. 17, 2015", 14 pgs.
"U.S. Appl. No. 13/751,846, Response filed May 11, 2015 to Restriction Requirement mailed Mar. 10, 2015", 15 pgs.
"U.S. Appl. No. 13/751,846, Response filed Oct. 9, 2015 to Non Final Office Action mailed Jun. 15, 2015", 20 pgs.
"U.S. Appl. No. 13/751,846, Restriction Requirement mailed Mar. 10, 2015", 7 pgs.
"U.S. Appl. No. 13/757,003, Non Final Office Action mailed Jun. 25, 2015", 8 pgs.
"U.S. Appl. No. 13/757,003, Notice of Allowance mailed Feb. 8, 2016", 10 pgs.
"U.S. Appl. No. 13/757,003, Response filed May 12, 2015 to Restriction Requirement mailed Mar. 12, 2015", 9 pgs.
"U.S. Appl. No. 13/757,003, Response filed Oct. 26, 2015 to Non Final Office Action mailed Jul. 25, 2015", 8 pgs.
"U.S. Appl. No. 13/757,003, Restriction Requirement mailed Mar. 12, 2015", 6 pgs.
"U.S. Appl. No. 13/757,019, Non Final Office Action mailed Jun. 25, 2015", 11 pgs.
"U.S. Appl. No. 13/757,019, Notice of Allowance mailed Dec. 10, 2015", 10 pgs.
"U.S. Appl. No. 13/757,019, Response filed May 11, 2015 to Restriction Requirement mailed Mar. 11, 2015", 9 pgs.
"U.S. Appl. No. 13/757,019, Response filed Oct. 26, 2015 to Non Final Office Action mailed Jun. 25, 2015", 9 pgs.
"U.S. Appl. No. 13/757,019, Restriction Requirement mailed Mar. 11, 2015", 10 pgs.
"U.S. Appl. No. 13/767,401, Non Final Office Action mailed Aug. 26, 2015", 9 pgs.
"U.S. Appl. No. 13/767,401, Notice of Allowance mailed Apr. 8, 2016", 9 pgs.
"U.S. Appl. No. 13/767,401, Notice of Allowance mailed Dec. 30, 2015", 9 pgs.
"U.S. Appl. No. 13/767,401, Response filed May 18, 2015 to Restriction Requirement mailed Mar. 17, 2015", 15 pgs.
"U.S. Appl. No. 13/767,401, Response filed Nov. 6, 2015 to Non Final Office Action mailed Aug. 26, 2015", 12 pgs.
"U.S. Appl. No. 13/767,401, Restriction Requirement mailed Mar. 17, 2015", 8 pgs.
"U.S. Appl. No. 13/790,982, Examiner Interview Summary mailed Jun. 9, 2015", 3 pgs.
"U.S. Appl. No. 13/790,982, Non Final Office Action mailed Sep. 16, 2015", 11 pgs.
"U.S. Appl. No. 13/790,982, Notice of Allowance mailed Feb. 24, 2016", 10 pgs.
"U.S. Appl. No. 13/790,982, Response filed Jun. 2, 2015 to Restriction Requirement mailed Apr. 2, 2015", 11 pgs.
"U.S. Appl. No. 13/790,982, Response filed Dec. 16, 2015 to Non Final Office Action mailed Sep. 16, 2015", 10 pgs.
"U.S. Appl. No. 13/790,982, Restriction Requirement mailed Apr. 2, 2015", 10 pgs.
"U.S. Appl. No. 13/790,997, Examiner Interview Summary mailed Jun. 8, 2015", 3 pgs.
"U.S. Appl. No. 13/790,997, Non Final Office Action mailed Sep. 21, 2015", 8 pgs.
"U.S. Appl. No. 13/790,997, Notice of Allowance mailed Mar. 2, 2016", 9 pgs.
"U.S. Appl. No. 13/790,997, Response filed Jun. 2, 2015 to Restriction Requirement mailed Apr. 2, 2015", 12 pgs.
"U.S. Appl. No. 13/790,997, Response filed Dec. 18, 2015 to Non Final Office Action mailed Sep. 21, 2015", 9 pgs.
"U.S. Appl. No. 13/790,997, Restriction Requirement mailed Apr. 2, 2015", 8 pgs.
"U.S. Appl. No. 13/833,567, Advisory Action mailed Apr. 28, 2016", 3 pgs.
"U.S. Appl. No. 13/833,567, Final Office Action mailed Mar. 9, 2016", 9 pgs.
"U.S. Appl. No. 13/833,567, Non Final Office Action mailed Oct. 23, 2015", 10 pgs.
"U.S. Appl. No. 13/833,567, Response filed Jan. 22, 2016 to Non Final Office Action mailed Oct. 23, 2015", 11 pgs.

(56) References Cited

OTHER PUBLICATIONS

"U.S. Appl. No. 13/833,567, Response filed Jun. 25, 2015 to Restriction Requirement mailed Apr. 3, 2015", 10 pgs.
"U.S. Appl. No. 13/833,567, Restriction Requirement mailed Apr. 3, 2015", 6 pgs.
"U.S. Appl. No. 13/838,755, Final Office Action mailed Feb. 22, 2016", 9 pgs.
"U.S. Appl. No. 13/838,755, Non Final Office Action mailed Sep. 17, 2015", 11 pgs.
"U.S. Appl. No. 13/838,755, Notice of Allowance mailed Apr. 27, 2016", 7 pgs.
"U.S. Appl. No. 13/838,755, Response filed Apr. 15, 2016 to Final Office Action mailed Feb. 22, 2016", 11 pgs.
"U.S. Appl. No. 13/838,755, Response filed Jun. 8, 2015 to Restriction Requirement mailed Apr. 6, 2015", 1 pg.
"U.S. Appl. No. 13/838,755, Response filed Dec. 1, 2015 to Non Final Office Action mailed Sep. 17, 2015", 13 pgs.
"U.S. Appl. No. 13/838,755, Restriction Requirement mailed Apr. 6, 2015", 6 pgs.
"U.S. Appl. No. 13/889,851, Non Final Office Action mailed Apr. 6, 2015", 10 pgs.
"U.S. Appl. No. 13/889,851, Notice of Allowance mailed Aug. 12, 2015", 8 pgs.
"U.S. Appl. No. 13/889,851, Response filed Feb. 26, 2015 to Restriction Requirement mailed Jan. 21, 2015", 12 pgs.
"U.S. Appl. No. 13/889,851, Response filed Jul. 6, 2015 to Non Final Office Action mailed Apr. 6, 2015", 14 pgs.
"U.S. Appl. No. 13/889,851, Restriction Requirement mailed Jan. 21, 2015", 6 pgs.
"U.S. Appl. No. 13/889,851, Supplemental Amendment and Response filed Jul. 6, 2015 to Non Final Office Action mailed Apr. 6, 2015", 8 pgs.
"U.S. Appl. No. 13/959,145, Examiner Interview Summary mailed Sep. 16, 2015", 3 pgs.
"U.S. Appl. No. 13/959,145, Final Office Action mailed Jan. 29, 2016", 16 pgs.
"U.S. Appl. No. 13/959,145, Final Office Action mailed Feb. 5, 2015", 22 pgs.
"U.S. Appl. No. 13/959,145, Non Final Office Action mailed Jul. 31, 2015", 21 pgs.
"U.S. Appl. No. 13/959,145, Non Final Office Action mailed Sep. 15, 2014", 20 pgs.
"U.S. Appl. No. 13/959,145, Notice of Allowance mailed Apr. 13, 2016", 5 pgs.
"U.S. Appl. No. 13/959,145, Response filed Mar. 28, 2016 to Final Office Action mailed Jan. 29, 2016", 10 pgs.
"U.S. Appl. No. 13/959,145, Response filed Jul. 6, 2015 to Final Office Action mailed Feb. 5, 2015", 18 pgs.
"U.S. Appl. No. 13/959,145, Response filed Oct. 30, 2015 to Non Final Office Action mailed Jul. 31, 2015", 14 pgs.
"U.S. Appl. No. 13/959,145, Response filed Dec. 15, 2014 to Non Final Office Action mailed Sep. 15, 2014", 21 pgs.
"U.S. Appl. No. 14/055,172, Restriction Requirement mailed Mar. 4, 2016", 6 pgs.
"U.S. Appl. No. 14/055,191, Restriction Requirement mailed Mar. 7, 2016", 6 pgs.
"U.S. Appl. No. 14/071,295, Non Final Office Action mailed Aug. 15, 2014", 6 pgs.
"U.S. Appl. No. 14/071,295, Notice of Allowance mailed Dec. 10, 2014", 8 pgs.
"U.S. Appl. No. 14/071,295, Response filed Nov. 17, 2014 to Non Final Office Action mailed Aug. 15, 2014", 14 pgs.
"U.S. Appl. No. 14/071,295, Supplemental Notice of Allowability mailed Jan. 26, 2015", 2 pgs.
"U.S. Appl. No. 14/095,614, Preliminary Amendment filed Apr. 15, 2014", 17 pgs.
"U.S. Appl. No. 14/107,350, Notice of Allowance mailed Feb. 26, 2016", 11 pgs.
"U.S. Appl. No. 14/107,350, Preliminary Amendment filed Feb. 28, 2014", 4 pgs.
"U.S. Appl. No. 14/159,094, Restriction Requirement mailed Apr. 20, 2016", 6 pgs.
"U.S. Appl. No. 14/182,038, Restriction Requirement mailed Apr. 26, 2016", 7 pgs.
"U.S. Appl. No. 14/182,046, Restriction Requirement mailed Apr. 26, 2016", 6 pgs.
"U.S. Appl. No. 14/211,977, Preliminary Amendment filed Mar. 2, 2016", 7 pgs.
"U.S. Appl. No. 14/211,977, Restriction Requirement mailed Mar. 11, 2016", 6 pgs.
"U.S. Appl. No. 14/215,550, Restriction Requirement mailed Apr. 28, 2016", 6 pgs.
"U.S. Appl. No. 14/275,548, Non Final Office Action mailed Feb. 19, 2016", 14 pgs.
"U.S. Appl. No. 14/324,688, Non Final Office Action mailed Jan. 8, 2016", 18 pgs.
"U.S. Appl. No. 14/324,688, Response filed Apr. 8, 2016 to Non Final Office Action mailed Jan. 8, 2016", 15 pgs.
"U.S. Appl. No. 14/456,286, Non Final Office Action mailed Dec. 30, 2015", 16 pgs.
"U.S. Appl. No. 14/456,286, Response filed Mar. 30, 2016 to Non Final Office Action mailed Dec. 30, 2015", 15 pgs.
"U.S. Appl. No. 14/456,286, Response filed Dec. 11, 2015 to Restriction Requirement mailed Oct. 29, 2015", 6 pgs.
"U.S. Appl. No. 14/456,286, Restriction Requirement mailed Oct. 29, 2015", 9 pgs.
"U.S. Appl. No. 14/589,101, Final Office Action mailed Oct. 2, 2015", 10 pgs.
"U.S. Appl. No. 14/589,101, Non Final Office Action mailed Feb. 12, 2015", 10 pgs.
"U.S. Appl. No. 14/589,101, Response filed Jun. 12, 2015 to Non Final Office Action mailed Feb. 12, 2015", 11 pgs.
"U.S. Appl. No. 14/589,101, Response filed Dec. 29, 2015 to Final Office Action mailed Oct. 2, 2015", 15 pgs.
"U.S. Appl. No. 14/697,140, Non Final Office Action mailed Apr. 8, 2016", 8 pgs.
"U.S. Appl. No. 14/794,309, Preliminary Amendment filed Sep. 22, 2015", 6 pgs.
"U.S. Appl. No. 14/794,309, Supplemental Preliminary Amendment filed Mar. 3, 2016", 8 pgs.
"U.S. Appl. No. 14/876,167, Preliminary Amendment filed Oct. 27, 2015", 8 pgs.
"U.S. Appl. No. 14/936,831, Preliminary Amendment filed Nov. 11, 2015", 6 pgs.
"U.S. Appl. No. 14/956,724, Preliminary Amendment filed Dec. 7, 2015", 8 pgs.
"U.S. Appl. No. 14/956,724, Supplemental Preliminary Amendment filed Feb. 11, 2016", 7 pgs.
"U.S. Appl. No. 14/983,108, Preliminary Amendment filed Dec. 30, 2015", 7 pgs.
"U.S. Appl. No. 14/983,747, Preliminary Amendment filed Jan. 4, 2016", 5 pgs.
"U.S. Appl. No. 15/060,007, Preliminary Amendment filed Mar. 9, 2016", 9 pgs.
"U.S. Appl. No. 15/061,352, Preliminary Amendment filed Mar. 7, 2016", 8 pgs.
"U.S. Appl. No. 15/074,553, Preliminary Amendment filed Mar. 21, 2016", 8 pgs.
"U.S. Appl. No. 12/938,902, Non Final Office Action mailed Sep. 17, 2012", 11 pgs.
"U.S. Appl. No. 12/938,902, Notice of Allowance mailed Jun. 21, 2013", 13 pgs.
"U.S. Appl. No. 12/938,902, Notice of Allowance mailed Oct. 1, 2013", 9 pgs.
"U.S. Appl. No. 12/938,902, Response filed Aug. 6, 2012 to Restriction Requirement mailed Jul. 6, 2012", 14 pgs.
"U.S. Appl. No. 12/938,902, Response filed Dec. 10, 2012 to Non Final Office Action mailed Sep. 17, 2012", 20 pgs.
"U.S. Appl. No. 12/938,902, Restriction Requirement mailed Jul. 6, 2012", 8 pgs.
"U.S. Appl. No. 13/833,567, Response filed Apr. 20, 2016 to Final Office Action mailed Mar. 9, 2016", 10 pgs.

(56) References Cited

OTHER PUBLICATIONS

"Bio-Intrafix Tibial Soft Tissue Fastener, Building on the Legacy of IntraFix", DePuy Mitek brochure, (Feb. 2007), 6 pgs.
"Bio-Intrafix Tibial Soft Tissue Fasteners, Building on the Legacy of IntraFix", (Feb. 2007), 6 pgs.
"Declaration of John White regarding PSCD and Customized Device and Exhibits 1-5".
"European Application Serial No. 10727548.9, Examination Notification Art. 94(3) mailed Sep. 18, 2014", 6 pgs.
"European Application Serial No. 10727548.9, Office Action mailed Jan. 11, 2016", 6 pgs.
"European Application Serial No. 10727548.9, Office Action mailed Jan. 19, 2012", 2 pgs.
"European Application Serial No. 10727548.9, Response filed Mar. 19, 2015 to Examination Notification Art. 94(3) mailed Sep. 18, 2014", 23 pgs.
"European Application Serial No. 11707316.3, Examination Notification Art. 94(3) mailed Feb. 4, 2014", 3 pgs.
"European Application Serial No. 11707316.3, Examination Notification Art. 94(3) mailed Dec. 17, 2014", 5 pgs.
"European Application Serial No. 11707316.3, Office Action mailed Nov. 10, 2015", 6 pgs.
"European Application Serial No. 11707316.3, Response filed Jun. 5, 2014 to Examination Notification Art. 94(3) mailed Feb. 4, 2014", 7 pgs.
"European Application Serial No. 11707316.3, Response filed Jun. 29, 2015 to Examination Notification Art. 94(3) mailed Dec. 17, 2014", 25 pgs.
"European Application Serial No. 12721676.0, Communication pursuant to Article 94(3) EPC mailed Sep. 30, 2015", 4 pgs.
"European Application Serial No. 12721676.0, Office Action mailed Jan. 3, 2014", 2 pgs.
"European Application Serial No. 12721676.0, Preliminary Amendment filed Nov. 19, 2013", 9 pgs.
"European Application Serial No. 12721676.0, Response filed Jul. 10, 2014 to Office Action mailed Jan. 3, 2014", 2 pgs.
"European Application Serial No. 12791902.5, Examination Notification Art. 94(3) mailed Aug. 14, 2015", 4 pgs.
"European Application Serial No. 12791902.5, Office Action mailed Jul. 15, 2014", 2 pgs.
"European Application Serial No. 12806211.4, Examination Notification Art. 94(3) mailed Aug. 13, 2015", 5 pgs.
"European Application Serial No. 12806211.4, Office Action mailed Jul. 18, 2014", 2 pgs.
"European Application Serial No. 13818131.8, Office Action mailed Jul. 28, 2015", 2 pgs.
"European Application Serial No. 13818131.8, Response filed Feb. 8, 2016 to Office Action mailed Jul. 28, 2015", 14 pgs.
"European Application Serial No. 14716173.1, Office Action mailed Nov. 5, 2015", 2 pgs.
"International Application Serial No. PCT/US2009/039580, International Preliminary Report on Patentability mailed Nov. 4, 2010", 9 pgs.
"International Application Serial No. PCT/US2009/039580, International Search Report mailed Jul. 30, 2009", 4 pgs.
"International Application Serial No. PCT/US2009/039580, Written Opinion mailed Jul. 30, 2009", 7 pgs.
"International Application Serial No. PCT/US2010/036602, International Preliminary Report on Patentability mailed Dec. 8, 2011", 9 pgs.
"International Application Serial No. PCT/US2010/036602, International Search Report mailed Nov. 8, 2010", 6 pgs.
"International Application Serial No. PCT/US2010/036602, Written Opinion mailed Nov. 8, 2010", 7 pgs.
"International Application Serial No. PCT/US2012/030294, International Preliminary Report on Patentability mailed Oct. 10, 2013", 9 pgs.
"International Application Serial No. PCT/US2012/030294, International Search Report mailed May 23, 2012", 6 pgs.
"International Application Serial No. PCT/US2012/030294, Written Opinion mailed May 23, 2012", 7 pgs.
"International Application Serial No. PCT/US2012/037703, Written Opinion mailed Nov. 28, 2013".
"International Application Serial No. PCT/US2012/062738, International Preliminary Report on Patentability mailed May 15, 2014", 9 pgs.
"International Application Serial No. PCT/US2012/062738, International Search Report mailed Mar. 6, 2013", 6 pgs.
"International Application Serial No. PCT/US2012/062738, Written Opinion mailed Mar. 6, 2013", 7 pgs.
"International Application Serial No. PCT/US2013/075989, International Preliminary Report on Patentability mailed Jul. 2, 2015", 10 pgs.
"International Application Serial No. PCT/US2014/026413, International Preliminary Report on Patentability mailed Sep. 24, 2015", 10 pgs.
"Mallory-Head Modular Calcar Revision System", Biomet Orthopedics, Inc., (2006), 20 pgs.
"SportMesh™ Soft Tissue Reinforcment, Made from . . . Artelon® optimal tissue repair", Biomet® Sports Medicine, Inc., (2007), 8 pgs.
Alford, J Winslow, et al., "Cartilage Restoration, Part 1. Basic Science, Historical Perspective, Patient Evaluation, and Treatment Options", The American Journal of Sports Medicine, 33(2), (2005), 295-306.
Anitua, Eduardo, et al., "Autologous platelets as a source of proteins for healing and tissue regeneration", Thromb Haemost, vol. 91, (2004), 4-15.
Arthrotek, "A Biomet Company; Sure fire Hybrid Meniscal Device", Fall AANA, (2004), 37 pgs.
Edwards, Andrew, et al., "The Attachments of the Fiber Bundles of the Posterior Cruciate ligament: An Anatomic Study", Arthroscopy: The Journal of Arthroscopic and Related Surgery, vol. 23, No. 3, (Mar. 2008), 284-290.
Floryan, K, et al., "Intraoperative use of Autologous Platelet-Rich and Platelet-Poor Plasma for Orthopedic Surgery Patients", AORN Journal: Home Study Program, 80(4), (Oct. 2004), 667-678.
Haynesworth, S E, et al., "Mitogenic Stimulation of Human Mesenchymal Stem Cells by Platelet Releasate Suggests a Mechanism for Enhancement of Bone Repair by Platelet Concentrate", 48th Annual Meeting of the Orthopaedic Research Society Poster No. 0462, (2002), 1 pg.
Mithoefer, Kai MD, et al., "The Microfracture Technique for the Treatment of Articular Cartilage Lesions in the Knee. A Prospective Cohort Study", The Journal of Bone and Joint Surgery 87(9), (Sep. 2005), 1911-1920.
Nixon, A J, "Platelet Enriched Plasma Provides an Intensely Anabolic Vehicle for Sustained Chondrocyte Function After Implantation", 52nd Annual Meeting of the Orthopedic Research Society: Paper No. 1416, (2005), 2 pgs.
Roseberg, MD, Thomas D, "ACL Reconstruction with Acufex Director Drill Guide and Endobutton CL Fixation System", Smith & Nephew: Knee Series, Technique Guide, (2005), 12 pgs.
Steadman, et al., "Microfracture: Surgical Technique and Rehalibitation to Treat Chondral Defects", Clinical Orthopaedics and Related Research 391, (2001), S362-S369.
"U.S. Appl. No. 13/281,009, Notice of Allowance mailed Jun. 23, 2016", 9 pgs.
"U.S. Appl. No. 13/288,459, Notice of Allowance mailed May 10, 2016", 7 pgs.
"U.S. Appl. No. 13/311,936, PTO Response to Rule 312 Communication mailed May 10, 2016", 2 pgs.
"U.S. Appl. No. 13/645,964, Notice of Allowance mailed Jul. 21, 2016", 9 pgs.
"U.S. Appl. No. 13/645,964, Response filed Jun. 13, 2016 to Non Final Office Action mailed Mar. 15, 2016", 11 pgs.
"U.S. Appl. No. 13/751,846, Notice of Allowance mailed Jul. 6, 2016", 9 pgs.
"U.S. Appl. No. 13/833,567, Non Final Office Action mailed May 27, 2016", 9 pgs.
"U.S. Appl. No. 13/959,145, Notice of Allowability mailed Jun. 14, 2016", 2 pgs.

(56) References Cited

OTHER PUBLICATIONS

"U.S. Appl. No. 14/055,172, Non Final Office Action mailed Jul. 14, 2016", 12 pgs.
"U.S. Appl. No. 14/055,172, Response filed May 4, 2016 to Restriction Requirement mailed Mar. 4, 2016", 8 pgs.
"U.S. Appl. No. 14/055,191, Non Final Office Action mailed May 16, 2016", 8 pgs.
"U.S. Appl. No. 14/055,191, Response filed Apr. 29, 2016 to Restriction Requirement mailed Mar. 7, 2016", 8 pgs.
"U.S. Appl. No. 14/095,614, Restriction Requirement mailed Jul. 11, 2016", 8 pgs.
"U.S. Appl. No. 14/095,639, Restriction Requirement mailed Jul. 19, 2016", 8 pgs.
"U.S. Appl. No. 14/159,094, Non Final Office Action mailed Jun. 29, 2016", 15 pgs.
"U.S. Appl. No. 14/159,094, Response filed Jun. 3, 2016 to Restriction Requirement mailed Apr. 20, 2016", 9 pgs.
"U.S. Appl. No. 14/182,038, Non Final Office Action mailed Jul. 19, 2016", 10 pgs.
"U.S. Appl. No. 14/182,038, Response filed Jun. 27, 2016 to Restriction Requirement mailed Apr. 26, 2016", 8 pgs.
"U.S. Appl. No. 14/182,046, Non Final Office Action mailed Jul. 15, 2016", 9 pgs.
"U.S. Appl. No. 14/182,046, Response filed Jun. 27, 2016 to Restriction Requirement mailed Apr. 26, 2016", 7 pgs.
"U.S. Appl. No. 14/211,977, Notice of Allowance mailed Jul. 12, 2016", 9 pgs.
"U.S. Appl. No. 14/211,977, Response filed Apr. 29, 2016 to Restriction Requirement mailed Mar. 11, 2016", 8 pgs.
"U.S. Appl. No. 14/215,550, Non Final Office Action mailed Jul. 19, 2016", 12 pgs.
"U.S. Appl. No. 14/215,550, Response filed Jun. 22, 2016 to Restriction Requirement mailed Apr. 28, 2016", 7 pgs.
"U.S. Appl. No. 14/275,548, Examiner Interview Summary mailed May 25, 2016", 3 pgs.
"U.S. Appl. No. 14/275,548, Response filed May 19, 2016 to Non Final Office Action mailed Feb. 19, 2016", 19 pgs.
"U.S. Appl. No. 14/324,688, Notice of Allowance mailed Jun. 9, 2016", 7 pgs.
"U.S. Appl. No. 14/456,286, Advisory Action mailed Jun. 21, 2016", 3 pgs.
"U.S. Appl. No. 14/456,286, Final Office Action mailed May 27, 2016", 15 pgs.
"U.S. Appl. No. 14/456,286, Response filed Jun. 13, 2016 to Final Office Action mailed May 27, 2016", 10 pgs.
"U.S. Appl. No. 14/492,590, Restriction Requirement mailed Jul. 25, 2016", 6 pgs.
"U.S. Appl. No. 14/589,101, Non Final Office Action mailed May 5, 2016", 14 pgs.
"U.S. Appl. No. 14/697,140, Response filed Jun. 13, 2016 to Non Final Office Action mailed Apr. 8, 2016", 10 pgs.
"European Application Serial No. 12721676.0, Response filed Apr. 11, 2016 to Communication pursuant to Article 94(3) EPC mailed Sep. 30, 2015", 38 pgs.
"European Application Serial No. 12806211.4, Response filed Feb. 23, 2016 to Communication Pursuant to Article 94(3) EPC mailed Aug. 13, 2015", 11 pgs.
"European Application Serial No. 14716173.1, Response filed May 16, 2016 to Communication pursuant to Rules 161(1) and 162 EPC mailed Nov. 5, 2015", 10 pgs.
"European Application Serial No. 12806211.4, Communication Pursuant to Article 94(3) EPC mailed Jun. 23, 2016", 4 pgs.
"ToggleLoc™ Fixation Device with ZipLoop™ Technology: ACL Reconstruction Bone-Tendon-Bone," by James R. Andrews, M.D., of Biomet Sports Medicine, a Biomet Company Brochure (2013), pp. 1-20.
International Preliminary Report on Patentability and Written Opinion mailed May 30, 2014 for PCT/US2012/064832 which claims benefit of U.S. Appl. No. 13/295,126, filed Nov. 14, 2011.

International Search Report and Written Opinion mailed Jun. 6, 2014 for PCT/US2014/026413 which claims benefit of U.S. Appl. No. 14/095,614, filed Dec. 3, 2013 and U.S. Appl. No. 14/095,639, filed Dec. 3, 2013.
ToggleLoc Fixation Device with ZipLoop Technology: Biceps Tendon Reattachment by Mark J. Albritton, M.D. and Daniel Worrel, M.D. of Biomet Sports Medicine, a Biomet Company Brochure (2099, 2011), pp. 1-12.
International Search Report and Written Opinion mailed Mar. 6, 2014 for PCT/US2013/075989 which claims benefit of U.S. Appl. No. 13/720,648, filed Dec. 19, 2012.
"AperFix® System Surgical Technique Guide. Single Tunnel Double Bundle.™" Cayenne Medical brochure. (Aug. 2008) 8 sheets.
"Arthroscopic Meniscal Repair using the Meniscal Cinch™", Surgical Technique brochure. (2008) Arthrex® 6 sheets.
"Bio-Intrafix (TCP/PLA & Intrafix, Tibial Soft Tissue Fasteners," by DePuy Mitek, 6 sheets, (date unknown).
"Bio-Intrafix Tibial Soft Tissue Fasteners, Building on the Legacy of IntraFix," brochure. DePuy Mitek,(Feb. 2007) 6 sheets.
"Biomechanical Evaluation of the Biomet Sports Medicine JurggerKnot™ Soft Anchor in Porcine Bone," Study completed Jan. 2010. Biomet Sports Medicine Research and Development, Warsaw, Indiana. 2 pages.
"Do your next distal tendon repair with . . . The Lubbers Technique", Teno Fix® brochure, 2003 (2 pages) Ortheon® Medical.
"EZ Loc Femoral Fixation Device," copyright 2005 Arthrotek, Inc. (8 sheets).
"JuggerKnot™ Soft Anchor Midfoot Repair," brochure. Biomet Sports Medicine (Jul. 2011) 12 sheets.
"JuggerKnot™ Soft Anchor. It's Small. It's strong. and it's all suture . . . " Ordering Information brochure. Biomet Sports Medicine (Jun. 2011) 2 sheets.
"JuggerKnot™ Soft Anchor. Labral Repair," brochure. Biomet Sports Medicine (Apr. 2011) 12 sheets.
"Make your next tendon repair an open-and-shut case. The Teno Fix® Tendon Repair System", Teno Fix® brochure, 2003 (2 pages) Ortheon® Medical.
"Panalok Anchor with PDS II and Ethibond Suture", Mitek Products Ethicon, 1997.
"SE Graft Tensioning System Surgical Technique," Linvatec Corporation copyright 2003, 2004.
"Suture Tensioner w/Tensiometer," Arthrex®, Inc. catalog "Next Generation in Knee Ligament Reconstruction & Repair Technology," 2009.
"Technique for ACL Reconstruction with Acufex Director Drill Guide and Endobutton CL," by Thomas D. Roseberg, copyright 1999 Smith & Nephew.
"TriTis™ Tibial Fixation System and Implant" brochure. Scandius Biomedical (2006).
A. Weiler, et al; Biodegradierbare Interferenzschrauben in der Kreuzbandchirurgie; Op-Journal 14 pp. 278-284; (Mar. 1998).
Arthrotek, A Biomet Company; Knees; Sure fire Hybrid Meniscal Device. (2005).
Arthrotek, A Biomet Company; Sure fire Hybrid Meniscal Device; Launch Date: Fall AANA 2004.
F. Alan Barber, M.D., "Uses and Abuses of Sutures and Anchors," Shoulder Scope, San Diego Shoulder Arthroscopy Library. http://www.shoulder.com/bass_barber.html Printed May 19, 2005.
F. Alan Barber, M.D., "Using Sutures and Anchors," San Diego Shoulder Arthroscopy Course, 17th Annual Meeting. (Jun. 14, 2000).
Flavia Namie Azato, et al. "Traction endurance biomechanical study of metallic suture anchors at different insertion angles," ACTA ortop. bras., vol. 11, No. 1, Sao Paulo, Jan./Mar. 2003.
Hecker AT, et al., "Pull-out strength of suture anchors for rotator cuff and Bankart lesion repairs," Am J Sports Med. 1993.
International Preliminary Report on Patentability and Written Opinion mailed Nov. 28, 2013 for PCT/US2012/037703, which claims benefit of U.S. Appl. No. 13/109,672, filed May 17, 2011,and U.S. Appl. No. 13/109,667, filed May 17, 2011.

(56) References Cited

OTHER PUBLICATIONS

International Preliminary Report on Patentability mailed Dec. 6, 2012 for PCT/US2011/038188 claiming benefit of U.S. Appl. No. 12/788,966, filed May 27, 2010.
International Preliminary Report on Patentability mailed Sep. 20, 2012 for PCT/US2011/026349 which claims benefit of U.S. Appl. No. 12/719,337, filed Mar. 8, 2010.
International Search Report and Written Opinion mailed Feb. 6, 2013 for PCT/US2012/064832 which claims benefit of U.S. Appl. No. 13/295,126, filed Nov. 14, 2011.
International Search Report and Written Opinion mailed Jul. 28, 2011 for PCT/US2011/026349 claiming benefit of U.S. Appl. No. 12/938,902, filed Nov. 3, 2010; and U.S. Appl. No. 12/719,337, filed Mar. 8, 2010.
International Search Report and Written Opinion mailed Mar. 6, 2013 for PCT/US2012/062738 which claims benefit of U.S. Appl. No. 13/288,459, filed Nov. 3, 2011.
International Search Report and Written Opinion mailed Oct. 14, 2011 for PCT/US2011/038188 filed May 26, 2011 claiming benefit of U.S. Appl. No. 12/788,973, filed May 27, 2010 and U.S. Appl. No. 12/788,966, filed May 27, 2010.
International Search Report and Written Opinion mailed Sep. 21, 2012 for PCT/US2012/037703 filed May 14, 2012 claiming benefit of U.S. Appl. No. 13/109,667, filed May 17, 2011 and U.S. Appl. No. 13/109,672, filed May 17, 2011.
Invitation to Pay Additional Fees mailed Aug. 5, 2011 for PCT/US2011/038188 claiming benefit of U.S. Appl. No. 12/788,973, filed May 27, 2010 and U.S. Appl. No. 12/788,966, filed May 27, 2010.
Invitation to Pay Additional Fees mailed Jul. 19, 2012, for PCT/US2012/037703 claiming benefit of U.S. Appl. No. 13/109,667, filed May 7, 2011.
Invitation to Pay Additional Fees mailed Jun. 9, 2011 for PCT/US2011/026349 claiming benefit of U.S. Appl. No. 12/938,902, filed Nov. 3, 2010; and U.S. Appl. No. 12/719,337, filed Mar. 8, 2010.
Lawhorn, M.D., Keith, MaxFire™ Meniscal Repair Device with Zip Loop™ Technology, Biomet Sports Medicine, Feb. 29, 2008.
Mark D. Miller et al.; "Pitfalls Associated with FasT-Fix Meniscal Repair," Arthroscopy: The Journal of Arthroscopic and Related Surgery, vol. 18, No. 8 (Oct. 2002): pp. 939-943.
Opus Medical; The AutoCuff System; www.opusmedical.com; 2003.
Patrick Hunt, et al.; Development of a Perforated Biodegradable Interference Screw; Arthroscopy: The Journal of Arthroscopic and Related Surgery, vol. 21, No. 3; pp. 258-265; Mar. 2005.
Pioneer® Sternal Cable System (2010).
Rapid Sternal Closure (2006) KLS Martin L.P. http://www.rapidsternalclosure.com/medical/demo.php Web accessed Sep. 8, 2008.
Roy Alan Majors, M.D.; "Meniscal repairs: proven techniques and current trends," Lippincott Williams & Wilkins, Inc.; 2002.
Saxena, Pankaj, MCh, DNB et al., "Use of Double Wires in Sternal Closure, A Useful Technique," Texas Heart® Institute. Journal List>Tex Heart Inst J > v.33(4); (2006).
Shoulder Arthroscopy; pp. H-2-H-22. (date unknown).
Smith & Nephew Endoscopy, "Endoscopic Meniscal Repair Using the T-Fix;" 1996.
Smith & Nephew, "Fast-Fix," Meniscal Repair System; 2001.
Stuart E. Fromm, M.D., RapidLoc, Meniscal Repair System, Mitek Products, Ethicon, 2001.
ToggleLoc™ Femoral Fixation Device, Arthrotek, Mar. 31, 2006.
Zeitani, Jacob, M.D., "A New Sternal Reinforcement Device to Prevent and Treat Sternal Dehiscence," CTSNet.org (Jun. 30, 2008).
"U.S. Appl. No. 13/288,459, Corrected Notice of Allowance mailed Aug. 3, 2016", 4 pgs.
"U.S. Appl. No. 13/288,459, Corrected Notice of Allowance mailed Sep. 9, 2016", 4 pgs.
"U.S. Appl. No. 13/288,459, Corrected Notice of Allowance mailed Sep. 23, 2016", 4 pgs.
"U.S. Appl. No. 13/833,567, Notice of Allowance mailed Sep. 27, 2016", 9 pgs.
"U.S. Appl. No. 13/833,567, Response filed Aug. 4, 2016 to Non Final Office Action mailed May 27, 2016", 11 pgs.
"U.S. Appl. No. 13/838,755, Notice of Allowance mailed Aug. 3, 2016", 8 pgs.
"U.S. Appl. No. 14/055,191, Notice of Allowability mailed Sep. 8, 2016", 7 pgs.
"U.S. Appl. No. 14/055,191, Notice of Allowance mailed Aug. 31, 2016", 13 pgs.
"U.S. Appl. No. 14/055,191, Response filed Aug. 3, 2016 to Non Final Office Action mailed May 16, 2016", 11 pgs.
"U.S. Appl. No. 14/095,614, Response filed Sep. 12, 2016 to Restriction Requirement mailed Jul. 11, 2016", 11 pgs.
"U.S. Appl. No. 14/095,639, Response filed Sep. 12, 2016 to Restriction Requirement mailed Jul. 19, 2016", 7 pgs.
"U.S. Appl. No. 14/107,350, Notice of Allowance mailed Jul. 27, 2016", 7 pgs.
"U.S. Appl. No. 14/159,094, Response filed Sep. 19, 2016 to Non Final Office Action mailed Jun. 29, 2016", 13 pgs.
"U.S. Appl. No. 14/182,038, Response filed Oct. 19, 2016 to Non Final Office Action mailed Jul. 19, 2016", 15 pgs.
"U.S. Appl. No. 14/182,046, Response filed Oct. 17, 2016 to Non Final Office Action mailed Jul. 15, 2016", 11 pgs.
"U.S. Appl. No. 14/275,548, Notice of Allowance mailed Jul. 27, 2016", 7 pgs.
"U.S. Appl. No. 14/324,688, Corrected Notice of Allowance mailed Sep. 22, 2016", 2 pgs.
"U.S. Appl. No. 14/456,286, Non Final Office Action mailed Oct. 17, 2016", 17 pgs.
"U.S. Appl. No. 14/492,590, Notice of Allowance mailed Oct. 5, 2016", 10 pgs.
"U.S. Appl. No. 14/492,590, Response filed Sep. 15, 2016 to Restriction Requirement mailed Jul. 25, 2015", 7 pgs.
"U.S. Appl. No. 14/492,590, Supplemental Response filed Sep. 26, 2016 to Restriction Requirement mailed Jul. 25, 2016", 10 pgs.
"U.S. Appl. No. 14/589,191, Response filed Aug. 5, 2016 to Non Final Office Action mailed May 5, 2016", 16 pgs.
"U.S. Appl. No. 14/697,140, Final Office Action mailed Sep. 23, 2016", 10 pgs.
"U.S. Appl. No. 14/956,724, Supplemental Preliminary Amendment filed Oct. 3, 2016", 8 pgs.
"U.S. Appl. No. 15/278,777, Preliminary Amendment filed Oct. 3, 2016", 7 pgs.
"U.S. Appl. No. 15/288,183, Preliminary Amendment filed Oct. 31, 2016", 7 pgs.
"U.S. Appl. No. 15/297,844, Preliminary Amendment filed Oct. 20, 2016", 7 pgs.
"Chinese Application Serial No. 201480027708.4, Office Action mailed May 26, 2016", W/English Translation, 15 pgs.
"Chinese Application Serial No. 201480027708.4, Response filed Oct. 10, 2016 to Office Action mailed May 26, 2016", With English Translation of Claims, 14 pgs.
"European Application Serial No. 12791902.5, Response filed Feb. 23, 2016 to Examination Notification Art. 94(3) mailed Aug. 14, 2015", 12 pgs.
"U.S. Appl. No. 13/281,009, Corrected Notice of Allowance mailed Dec. 12, 2016", 2 pgs.
"U.S. Appl. No. 14/055,172, Final Office Action mailed Dec. 22, 2016", 8 pgs.
"U.S. Appl. No. 14/095,614, Non Final Office Action mailed Jan. 19, 2017", 9 pgs.
"U.S. Appl. No. 14/095,639, Non Final Office Action mailed Jan. 18, 2017", 10 pgs.
"U.S. Appl. No. 14/182,038, Final Office Action mailed Dec. 19, 2016", 8 pgs.
"U.S. Appl. No. 14/182,038, Response filed Feb. 20, 2017 to Final Office Action mailed Dec. 19, 2016", 11 pgs.
"U.S. Appl. No. 14/182,038, Advisory Action mailed Mar. 1, 2017", 3 pgs.
"U.S. Appl. No. 14/182,046, Corrected Notice of Allowance mailed Jan. 20, 2017", 6 pgs.

(56) References Cited

OTHER PUBLICATIONS

"U.S. Appl. No. 14/182,046, Notice of Allowance mailed Dec. 8, 2016", 7 pgs.
"U.S. Appl. No. 14/215,550, Final Office Action mailed Feb. 1, 2017", 11 pgs.
"U.S. Appl. No. 14/215,550, Response filed Dec. 5, 2016 to Non Final Office Action mailed Jul. 19, 2016", 13 pgs.
"U.S. Appl. No. 14/456,286, Notice of Allowance mailed Feb. 15, 2017", 9 pgs.
"U.S. Appl. No. 14/456,286, Response filed Nov. 16, 2016 to Non Final Office Action mailed Oct. 17, 2016", 9 pgs.
"U.S. Appl. No. 14/589,101, Advisory Action mailed Feb. 21, 2017", 5 pgs.
"U.S. Appl. No. 14/589,101, Examiner Interview Summary mailed Jan. 30, 2017", 3 pgs.
"U.S. Appl. No. 14/589,101, Response filed Jan. 23, 2017 to Final Office Action mailed Nov. 16, 2016", 9 pgs.
"U.S. Appl. No. 14/594,285, Non Final Office Action mailed Jan. 11, 2017", 15 pgs.
"U.S. Appl. No. 14/594,285, Response filed Dec. 14, 2016 to Restriction Requirement mailed Nov. 7, 2016", 8 pgs.
"U.S. Appl. No. 14/697,140, Non Final Office Action mailed Jan. 10, 2017", 12 pgs.
"U.S. Appl. No. 14/794,309, Response filed Feb. 22, 2017 to Non Final Office Action mailed Nov. 22, 2016", 12 pgs.
"U.S. Appl. No. 15/131,663, Preliminary Amendment filed Dec. 21, 2016", 6 pgs.
"U.S. Appl. No. 15/200,546, Preliminary Amendment filed Dec. 21, 2016", 6 pgs.
"U.S. Appl. No. 15/294,994, Preliminary Amendment filed Jan. 25, 2017", 8 pgs.
"U.S. Appl. No. 13/281,009, Corrected Notice of Allowance mailed Nov. 18, 2016", 4 pgs.
"U.S. Appl. No. 13/281,009, Examiner Interview Summary mailed Nov. 18, 2016", 2 pgs.
"U.S. Appl. No. 14/055,172, Response filed Nov. 14, 2016 to Non Final Office Action mailed Jul. 14, 2016", 19 pgs.
"U.S. Appl. No. 14/159,094, Examiner Interview Summary mailed Nov. 29, 2016", 1 pg.
"U.S. Appl. No. 14/159,094, Notice of Allowance mailed Nov. 29, 2016", Examiner Interview Summary from Nov. 29, 2016 included, 11 pgs.
"U.S. Appl. No. 14/589,101, Final Office Action mailed Nov. 16, 2016", 12 pgs.
"U.S. Appl. No. 14/697,140, Response filed Nov. 16, 2016 to Final Office Action mailed Sep. 23, 2016", 13 pgs.
"U.S. Appl. No. 14/794,309, Non Final Office Action mailed Nov. 22, 2016", 13 pgs.
"U.S. Appl. No. 15/332,590, Preliminary Amendment filed Nov. 22, 2016", 5 pgs.
"U.S. Appl. No. 15/361,917, Preliminary Amendment filed Nov. 30, 2016", 6 pgs.
"U.S. Appl. No. 14/215,550, Examiner Interview Summary mailed Mar. 9, 2017", 3 pgs.
"U.S. Appl. No. 14/794,309, Final Office Action mailed Mar. 20, 2017", 18 pgs.
"U.S. Appl. No. 15/401,768, Preliminary Amendment filed Mar. 23, 2017", 6 pgs.
"U.S. Appl. No. 15/455,896, Preliminary Amendment filed Mar. 13, 2017", 6 pgs.
"Chinese Application Serial No. 201480027708.4, Office Action mailed Feb. 14, 2017", With English Translation, 18 pgs.

METHOD AND APPARATUS FOR STERNAL CLOSURE

CROSS-REFERENCE TO RELATED APPLICATIONS

This application is a divisional of U.S. patent application Ser. No. 12/938,902 filed on Nov. 3, 2010, now U.S. Pat. No. 8,597,327, which is a continuation-in-part of U.S. patent application Ser. No. 12/915,962 filed on Oct. 29, 2010, now U.S. Pat. No. 8,562,647, which is a continuation-in-part of U.S. patent application Ser. No. 12/719,337 filed on Mar. 8, 2010, now U.S. Pat. No. 9,078,644, which is a continuation-in-part of U.S. patent application Ser. No. 12/489,168 filed on Jun. 22, 2009, now U.S. Pat. No. 8,361,113 issued on Jan. 29, 2013, which is a continuation-in-part of U.S. patent application Ser. No. 12/474,802 filed on May 29, 2009, now U.S. Pat. No. 8,088,130 issued on Jan. 3, 2012, which is a continuation-in-part of (a) U.S. patent application Ser. No. 12/196,405 filed on Aug. 22, 2008, now U.S. Pat. No. 8,128,658 issued on Mar. 6, 2012; (b) U.S. patent application Ser. No. 12/196,407 filed on Aug. 22, 2008, now U.S. Pat. No. 8,137,382 issued on Mar. 20, 2012; (c) U.S. patent application Ser. No. 12/196,410 filed on Aug. 22, 2008, now U.S. Pat. No. 8,118,836 issued on Feb. 21, 2012; and (d) a continuation-in-part of U.S. patent application Ser. No. 11/541,506 filed on Sep. 29, 2006, which is now U.S. Pat. No. 7,601,165 issued on Oct. 13, 2009.

This application is a continuation-in-part of U.S. patent application Ser. No. 13/645,964 filed on Oct. 5, 2012, which is a divisional of U.S. patent application Ser. No. 12/570,854 filed on Sep. 30, 2009, which is now U.S. Pat. No. 8,303,604 issued on Nov. 6, 2012, which is a continuation-in-part of U.S. patent application Ser. No. 12/014,399 filed on Jan. 15, 2008, which is now U.S. Pat. No. 7,909,851 issued on Mar. 22, 2011, which is a continuation-in-part of U.S. patent application Ser. No. 11/347,661 filed on Feb. 3, 2006, which is now U.S. Pat. No. 7,749,250 issued on Jul. 6, 2010.

This application is a continuation-in-part of U.S. patent application Ser. No. 13/587,374 filed on Aug. 16, 2012, which is now U.S. Pat. No. 8,777,956, which is a divisional of U.S. patent application Ser. No. 12/029,861 filed on Feb. 12, 2008, which is now U.S. Pat. No. 8,251,998 issued on Aug. 28, 2012, which is a continuation-in-part of U.S. patent application Ser. No. 11/504,882 filed on Aug. 16, 2006, which is now U.S. Pat. No. 8,998,949, which is a continuation-in-part of U.S. patent application Ser. No. 11/408,282 filed on Apr. 20, 2006, now abandoned.

This application is a continuation-in-part of U.S. patent application Ser. No. 12/702,067 filed on Feb. 8, 2010, which is now U.S. Pat. No. 8,672,968, which is a continuation of U.S. patent application Ser. No. 11/541,505 filed on Sep. 29, 2006 and is now U.S. Pat. No. 7,658,751 issued on Feb. 9, 2010.

This application is a continuation-in-part of U.S. patent application Ser. No. 13/098,927 filed on May 2, 2011, which is now U.S. Pat. No. 8,852,171, which is a continuation-in-part of U.S. patent application Ser. No. 12/196,398 filed Aug. 22, 2008, which is now U.S. Pat. No. 7,959,650 issued on Jun. 14, 2011, which is a continuation-in-part of U.S. patent application Ser. No. 11/784,821 filed Apr. 10, 2007, which is now U.S. Pat. No. 9,017,381.

The disclosures of all of the above applications are incorporated by reference herein.

FIELD

The present disclosure relates generally to methods and arrangements for securing a fractured or sectioned bone, and more particularly to methods and arrangements for sternal closure.

BACKGROUND

The statements in this section merely provide background information related to the present disclosure and may not constitute prior art.

After trauma or surgical intervention, there may be a need to fix bone fragments or portions together to immobilize the fragments and permit healing. Compressive force can be applied to the bone fragments by encircling the bone fragments or bridging the fragments together across a broken, sectioned (cut) or otherwise compromised portion of the bone. The compressive forces should be applied such that upon ingrowth of new bone, the fragments will heal together and restore strength to the site of trauma or surgical intervention.

Accordingly, there is a need for apparatus and methods to apply compressive force to a bone across a fracture or section (cut) to maintain alignment and assist healing. Further, there is a need for apparatus and methods that are easy to use intraoperatively to accommodate various bone sizes or shapes, or locations of bone fractures or sections.

SUMMARY

This section provides a general summary of the disclosure, and is not a comprehensive disclosure of its full scope or all of its features.

In one aspect, an apparatus for securing a fractured or sectioned bone in a patient's body is provided. The apparatus can include an attachment member and an adjustable flexible member construct. The attachment member can have a flexible member holder. The adjustable flexible member construct can have a body extending from a first end to a second end and defining at least one passage portion. The first and second ends can be passed into and through the at least one passage portion via at least first and second openings associated with the at least one passage portion of the adjustable flexible member construct to form a pair of loops. The attachment member can be configured to be coupled to at least one of the formed pair of loops.

In another aspect, a method is provided for securing a fractured or sectioned sternum in a patient's body. The method can include forming an adjustable flexible member construct, which can include providing a flexible member having first and second ends and a body defining first and second passage portions spaced apart from each other by a first portion of the flexible member. The first end can be passed into and through the second passage portion and then into and through the first passage portion to form a first loop. The second end can be passed into and through the first passage portion in an opposite direction as the first end and then into and through the second passage portion in an opposite direction as the first end to form a second loop. An attachment member can be coupled to the first and second loops. The fractured or sectioned sternum can be encircled by at least partially wrapping the formed adjustable flexible member construct about the sternum. The first portion of the flexible member construct opposite the loops can be coupled to the attachment member. The adjustable flexible member construct can be reduced to compress the fractured or sectioned sternum.

In yet another aspect, a method is provided for securing a fractured or sectioned sternum in a patient's body. The method can include providing an adjustable flexible member construct and positioning the adjustable flexible member construct across a fracture or section of the fractured or sectioned sternum. The adjustable flexible member construct can have first and second ends and a body defining at least one passage portion therebetween. The first and second ends can be passed into and through the at least one passage portion via at least first and second apertures associated with the at least one passage portion of the adjustable flexible member construct to form a pair of loops. A fixation arrangement can be provided and the pair of loops can be coupled to the fixation arrangement. The adjustable flexible member construct can be reduced to a reduced position to compress the fractured or sectioned sternum by applying tension to the first and second ends of the adjustable flexible member construct and thereby reducing the size of the pair of loops. The adjustable flexible member construct can be automatically maintained in the reduced position.

Further areas of applicability will become apparent from the description provided herein. The description and specific examples in this summary are intended for purposes of illustration only and are not intended to limit the scope of the present disclosure.

DRAWINGS

The present teachings will become more fully understood from the detailed description, the appended claims and the following drawings. The drawings are for illustrative purposes only and are not intended to limit the scope of the present disclosure.

DETAILED DESCRIPTION

Figure 1:
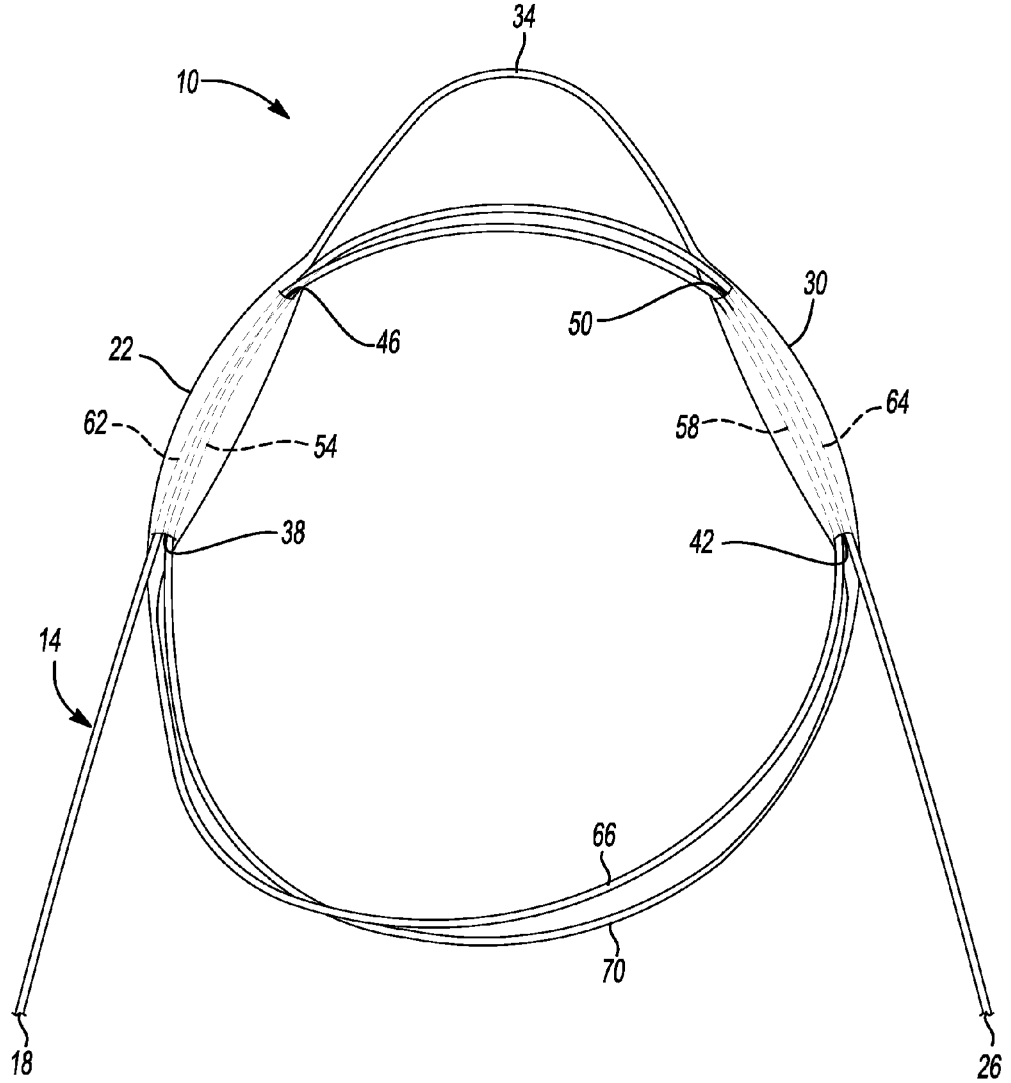
FIG. 1 depicts an adjustable flexible member construct according to the present teachings.

The following description is merely exemplary in nature and is in no way intended to limit the present disclosure, its application, or uses. It should be understood that throughout the drawings, corresponding reference numerals indicate like or corresponding parts and features. While the disclosure relates to apparatus and associated methods for sternal closure, the apparatus and methods of the present teachings can be used in connection with various other fracture fixation methods and/or procedures.

Referring to FIG. 1, an adjustable flexible member construct 10 is provided according to various aspects of the present teachings. The adjustable flexible member construct 10 can be fashioned from a flexible member 14 made of any biocompatible material including, but not limited to, non-resorbable polymers, such as polyethylene or polyester, resorbable polymers, and various combinations thereof. In various aspects, the adjustable flexible member construct 10 can include a hollow material or core to allow for appropriate tensioning, as will be discussed herein. In various aspects, the adjustable flexible member construct 10 can be a suture. In such aspects, the suture can be hollow or a braided or a multiple-filament braided suture structure having a hollow core. In various aspects, the suture can be resorbable. In various aspects, the adjustable flexible member construct 10 can define a substantially tubular hollow shape.

The adjustable flexible member construct 10 can include a first end 18, a first formed passage portion 22, a second end 26, a second formed passage portion 30, and a fixed length loop portion 34 connecting the first and second passage portions 22, 30, as shown in FIG. 1. In one exemplary aspect, flexible member construct 10 can include an elongated body 32 having an exterior surface and an interior surface defining an elongated passage between the first and second ends 18, 26. The body 32 can define the first and second passage portions 22, 30 and the fixed length portion 34 therebetween. Passage portions 22, 30 can each include first apertures 38, 42 positioned proximate one end thereof, and second apertures 46, 50 positioned proximate a second opposite end thereof. The passage portions 22, 30 can be formed to have a larger width or diameter than remaining portions of flexible member 14, as shown for example in FIG. 1. Alternatively, the passage portions 22,30 can be formed initially to have the same width or diameter as the remaining portions of flexible member 14, later expanding in diameter during the construction process. In various aspects, the first and second apertures 38, 42, 46, 50 can be formed during a braiding process of flexible member 14 as loose portions between pairs of fibers defining flexible member 14, or can be formed during the construction process. Alternatively, the first and second ends can be pushed between individual fibers of the braided flexible member 14, as will be discussed herein.

Figure 1A:
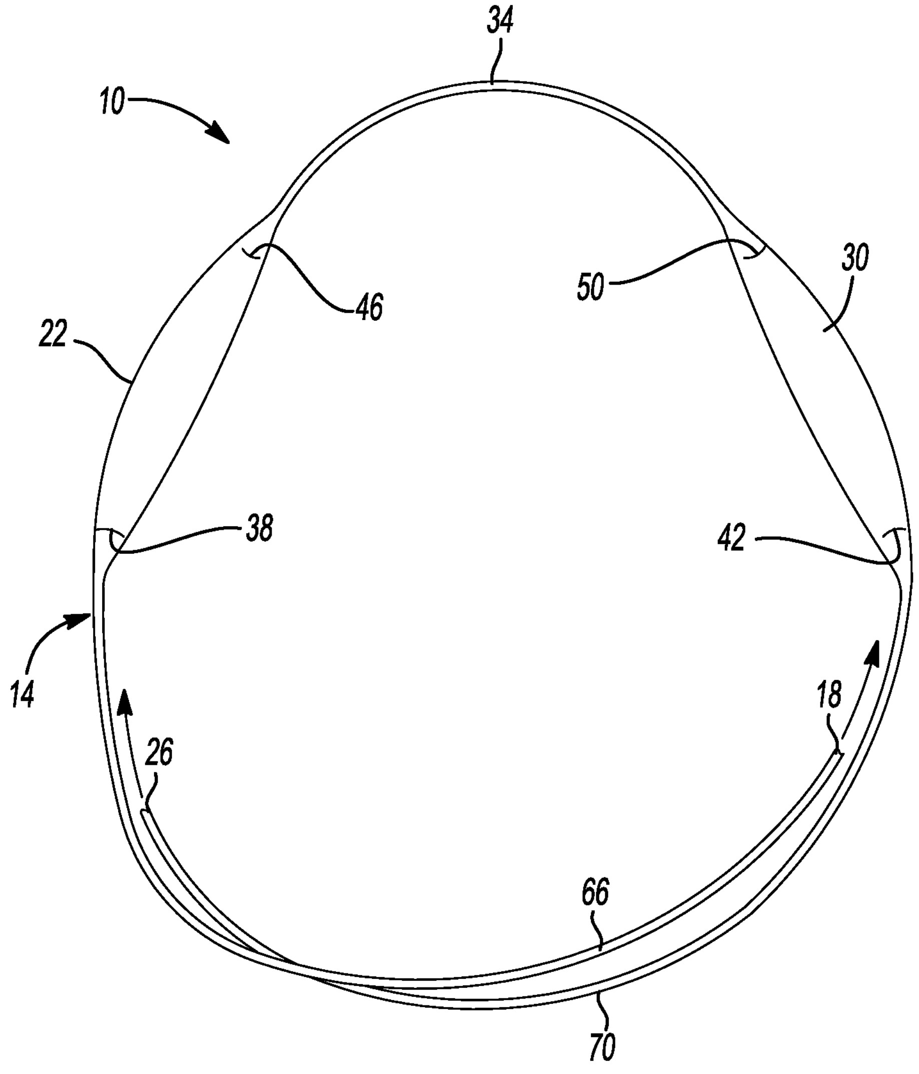
FIGS. 1A and 1B depict an exemplary method of assembling the adjustable flexible construct of FIG. 1 according to the present teachings.
Figure 1B:
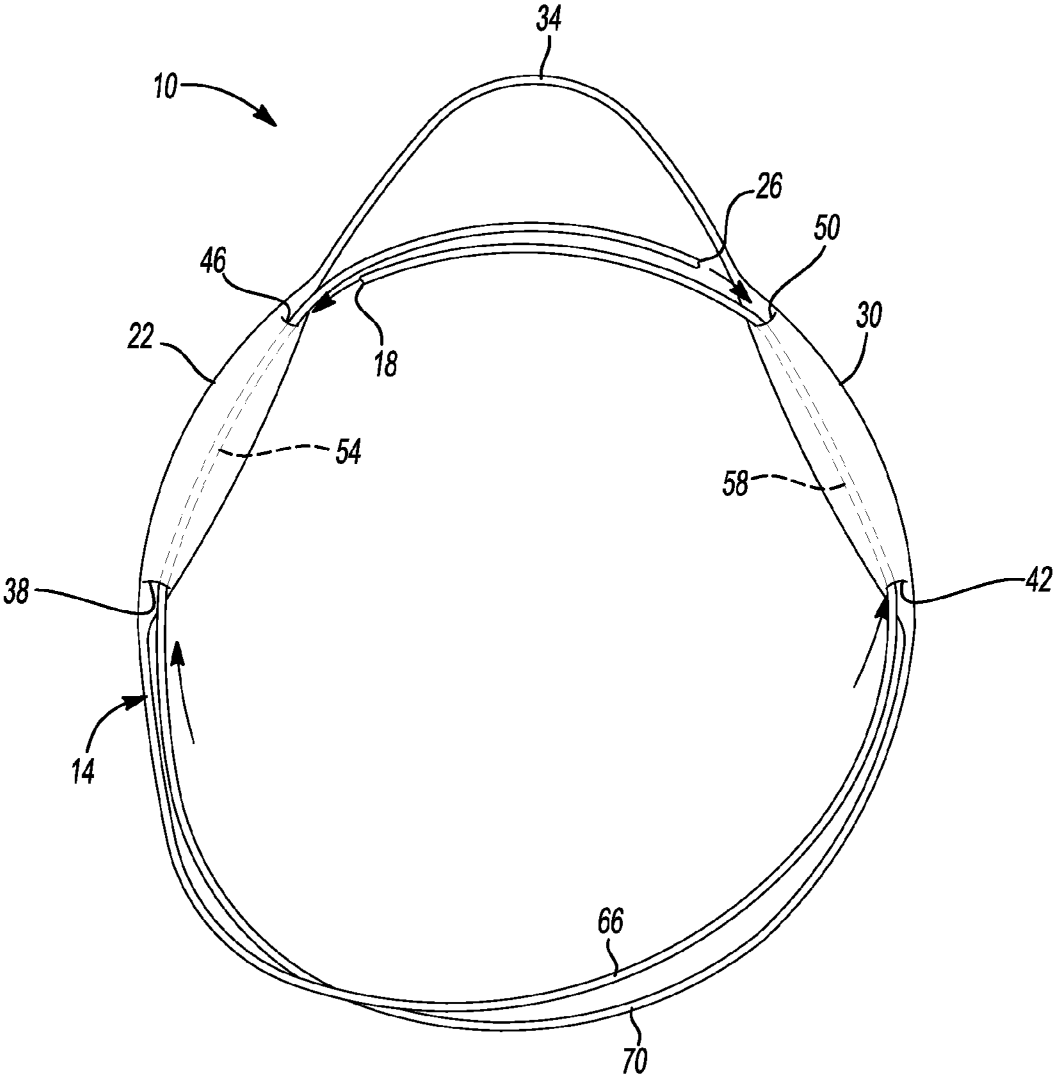

To form the adjustable flexible member construct 10, first end 18 can be passed through second passage portion 30 via first and second apertures 42, 50, as generally shown in FIGS. 1A and 1B. In a similar manner, second end 26 can be passed through the first passage portion 22 via the first and second apertures 38, 46, as also shown in FIGS. 1A and 1B. Subsequently, as shown in FIG. 1B with reference to FIG. 1, first end 18 can be passed through the first passage portion 22 via second and first apertures 46 and 38, respectively. First end 18 can follow a path that is opposite in direction to a path followed by a portion 54 of the flexible member 14 that has already passed through first passage portion 22 while following second end 26 through first and second apertures 38 and 46. Similarly, second end 26 can be passed through the second passage portion 30 via second and first apertures 50 and 42, respectively. First end 26 can follow a path that is opposite in direction to a path followed by a portion 58 of the flexible member 14 that has already passed through second passage portion 30 while following first end 18 through first and second apertures 42 and 50. This results in portions 62, 64 of flexible member 14 being positioned parallel or substantially parallel to portions 54, 58 in passage portions 22, 30. Passing the first and second ends 18, 26 though passage portions 22, 30 as discussed above forms adjustable loops 66, 70, as shown in FIG. 1. The first and second ends can be passed through the same apertures in each passage portion 22, 30 or, alternatively, through separate apertures in each passage portion 22, 30.

The adjustable flexible member construct 10 can thus provide a double adjustable loop configuration via loops 66, 70 while also providing portion 34, which can have a fixed length between the passage portions 22, 30. As will be discussed in greater detail herein, this configuration can be used, for example, to couple an attachment member to loops 66, 70 and couple fixed length portion 34 to either the attachment member or another device. In this manner, the amount of friction developed within the first and second passage portions 22, 30 relative to and among portions 54, 58, 62 and 64 during adjustment of adjustable loops 66, 70 is reduced as compared to that which would occur if the attachment member were coupled to the passage portion when the loops are being adjusted or reduced in size under tension.

Figure 2:
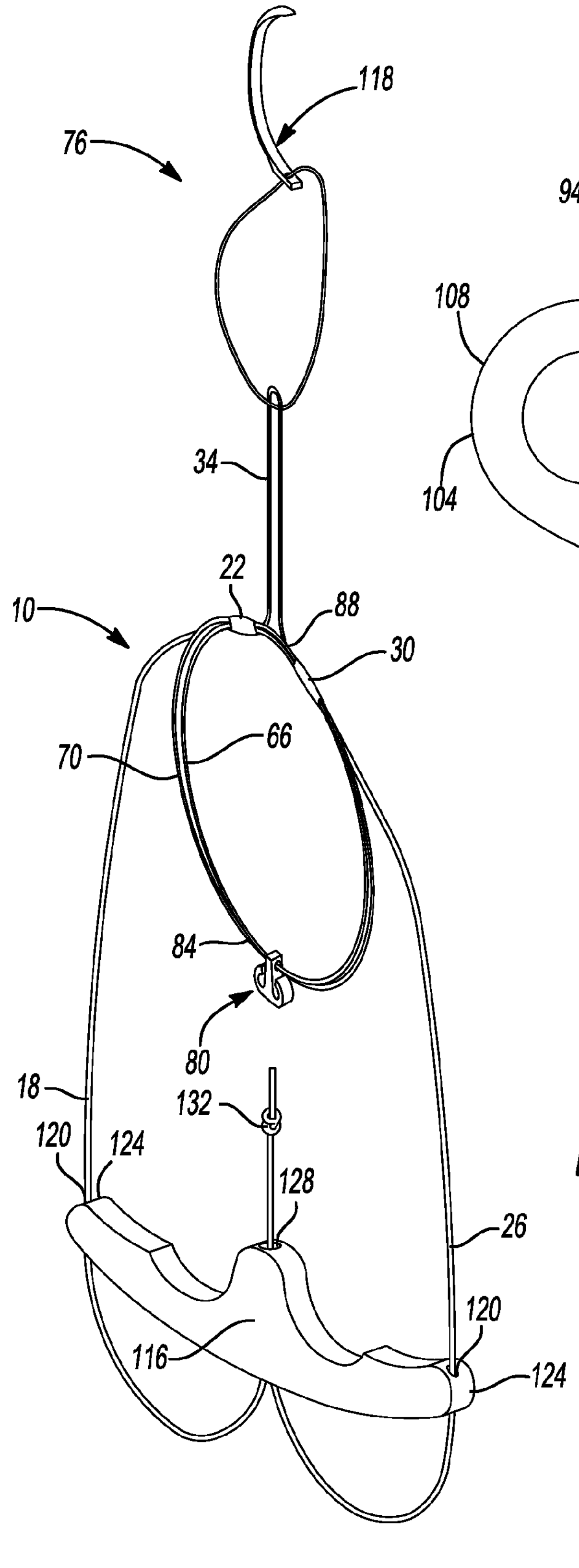
FIG. 2 depicts an exemplary assembly configuration of the flexible member construct of FIG. 1 having an attachment member and an insertion member according to the present teachings.
Figure 2A:
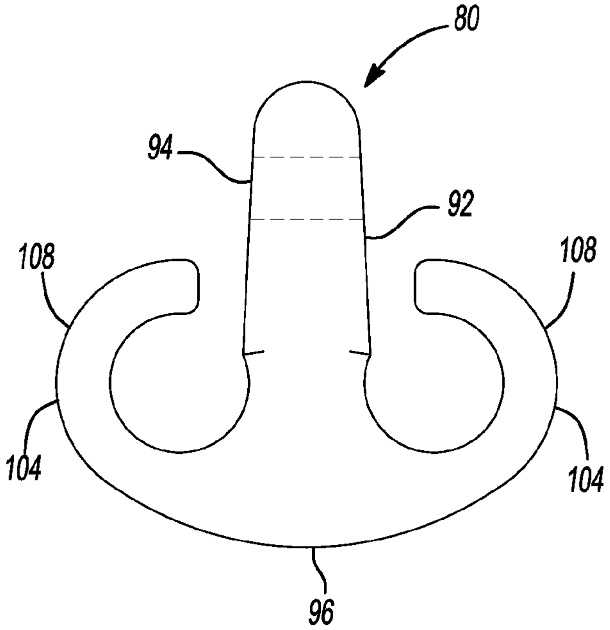
FIG. 2A depicts a side view of the attachment member of FIG. 2 according to the present teachings.

With additional reference to FIGS. 2 and 2A, adjustable flexible member construct 10 is shown in an exemplary assembly configuration 76 having an attachment member 80 coupled to a first side 84 of loops 66, 70 opposite a second side 88 facing fixed length portion 34. Attachment member 80 can include a generally T-shaped configuration having a first stem portion 92 defining an aperture 94 for receipt of loops 66, 70 therein at one end, and a transversely extending cross portion 96 at a second opposite end. Transversely extending portion 96 can include opposed lateral ends 104 that include arcuate or curled portions 108, as shown in FIG. 2A. In various aspects, attachment member 80 can be used to secure a flexible member loop thereto by placing the loop over first portion 92 and under arcuate portions 108, as shown for example in FIG. 4.

The assembly configuration 76 can also include an optional grab member or handle 116 and a passing or needle member 118. Handle 116 can be used to aid the surgeon in easily pulling ends 18, 26 of construct 10 to reduce the size of loops 66, 70, as will be discussed in greater detail below. Handle 116 can include a first pair of apertures 120 positioned at opposed ends 124 of handle 116, as shown in FIG. 2. The first and second ends 18, 26 can be passed or routed through apertures 120 and then through a central aperture 128, where ends 18, 26 can be secured to handle 116 by various methods, including a knot 132, as also shown in FIG. 2. The surgeon can use handle 116 to apply simultaneous tension to ends 18, 26, which can thereby evenly reduce or adjust loops 66, 70 to a desired size or tension.

Operation of the adjustable flexible member construct 10 will now be described in greater detail with reference to an exemplary configuration where adjustable flexible member construct 10 is wrapped around or encircles a bone, such as a sternum, and fixed loop 34 is connected to attachment member 80, as shown for example in FIG. 4. It should be appreciated, however, that construct 10 can be used in various attachment configurations, other than the example discussed above, wherein tension is applied to construct 10 via fixed loop 34 and attachment member 80 in connection with reducing or adjusting the size of loops 66, 70.

Upon applying tension to ends 18, 26, with or without handle 116, the loops 66, 70 can be reduced to a desired size and/or placed in a desired tension by causing translation of ends 18, 26 relative to passage portions 22, 30. Tension in fixed length loop portion 34 combined with the tension in adjustable loops 66, 70 can cause the body 32 of flexible member 14 defining the passage portions 22, 30 to constrict about the portions 54, 58 and 62, 64 of flexible member 14 passed therethrough. This constriction can reduce a width or diameter of each of the passage portions 22, 30, thereby forming a mechanical interface between exterior surfaces of the passed through portions of flexible member 14 and interior surfaces of the passage portions 22, 30. The static friction between the interior and exterior surfaces at the mechanical interface formed as a result of the constriction can prevent relative movement of portions 54, 58, and 62, 64 relative to passages 22, 30 and hence prevent relaxation of the tension in construct 10, thereby preventing an increase in the size of loops 66, 70. Thus, adjustable flexible member construct 10 provides for "automatically" locking loops 66, 70 in a reduced length or size under tension without requiring a knot.

Flexible member construct 10 can be provided in various sizes to accommodate differently sized bones, such as sternums, in different patients. In one exemplary configuration, fixed loop portion 34 can be provided in various sizes or lengths. Flexible member construct 10 can also be provided with flexible member 14 having various diameters, such as 30 thousandths of an inch or 37-40 thousandths of an inch. In one exemplary configuration, the 30 thousandths diameter flexible member 14 can be used, for example, where construct 10 is routed or passed through holes drilled in the bone so that flexible member 14 can be more easily manipulated during such routing. The larger 37-40 thousandths diameter flexible member 14 can be used, for example, where the construct 10 is wrapped around the sternum, as will be discussed herein. Forming the construct 10, as well as other constructs discussed herein, with a larger diameter flexible member provides more surface area of the tensioned flexible member to engage the sternum or other bone, and thus distribute the compressive load over a greater area of the bone.

Figure 3:
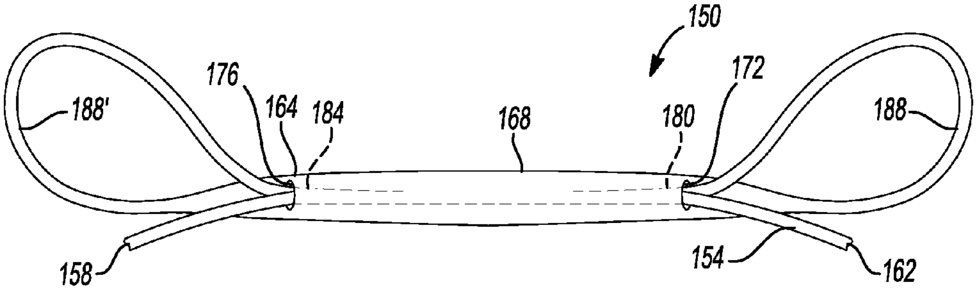
FIGS. 3, 3A and 3B depict alternative flexible member constructs according to the present teachings.
Figure 3A:
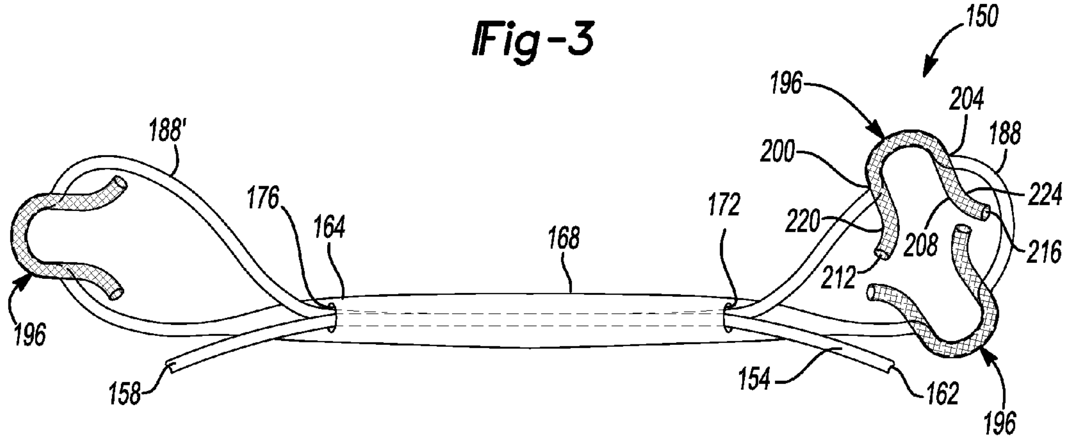

With additional reference to FIG. 3, and FIG. 3A, an exemplary alternative adjustable flexible member construct 150 is shown. Construct 150 can include a hollow flexible member 154 having a first end 158 and a second end 162, and can include a body 164 that defines a longitudinal passage portion 168 therein between first and second ends 158, 162, as shown in FIG. 3. The passage portion 168 can define a pair of apertures 172, 176 at opposed ends thereof, similar to apertures 38, 46 discussed above. To form construct 150, the first end 158 can be passed through aperture 172 and passage portion 168 and out aperture 176 such that a portion 180 of flexible member 154 following first end 158 extends through passage portion 168. In a similar manner, second end 162 can be passed through aperture 176 and passage portion 168 and out aperture 172 such that a portion 184 of flexible member 154 following second end 162 also extends through passage portion 168. This configuration forms two loops 188 and 188', as shown in FIG. 3. It should be appreciated that each of the first and second ends 158, 162 can alternatively be pushed through a respective space defined between adjacent individual fibers of the braided flexible member 14 such that the respective spaces defined between fibers comprise apertures 172, 176 in communication with an interior longitudinal passage.

The pulling of ends 158, 162 can cause movement of portions 180, 184 relative to passage portion 168, and the loops 188, 188' can be reduced to a desired size or placed in a desired tension. Tension in loops 188, 188' can cause the body 164 defining the passage portion 168 to be placed in tension and therefore cause passage portion 168 to constrict about portions 180, 184 passed therethrough. This constriction reduces the diameter of passage portion 168, thus forming a mechanical interface between the exterior surfaces of portions 180, 184 and an interior surface of passage portion 168. This constriction results in static friction between the interior and exterior surfaces at the mechanical interface, causing the adjustable flexible member 154 to "automatically" lock in a reduced size or diameter configuration in which tension is maintained. Flexible member construct 150 with adjustable loops 188, 188' can be used to compress a fractured or sectioned bone, such as a sectioned sternum in a sternal closure procedure following open chest surgery, as will be discussed herein.

With additional reference to FIG. 3A, adjustable flexible member construct 150 is shown having attachment members or flexible anchors 196 coupled to loops 188, 188'. Each loop can include various numbers of anchors coupled thereto, including more or fewer anchors 196 than shown. Each anchor 196 can define a hollow core and can include a pair of apertures 200, 204 formed in a body 208 thereof in a similar manner as apertures 38, 46 discussed above. Flexible member 154 can pass through first aperture 204 into the hollow core and out through the second aperture 200, as shown in FIG. 3A. Apertures 200, 204 can be placed inward from respective ends 212, 216 of anchors 196 so as to form tail portions 220, 224 adjacent each aperture 200, 204. The tail portions 220, 224 can provide anchoring resistance relative to a corresponding bone or anchoring structure, as will discussed herein.

Figure 3B:
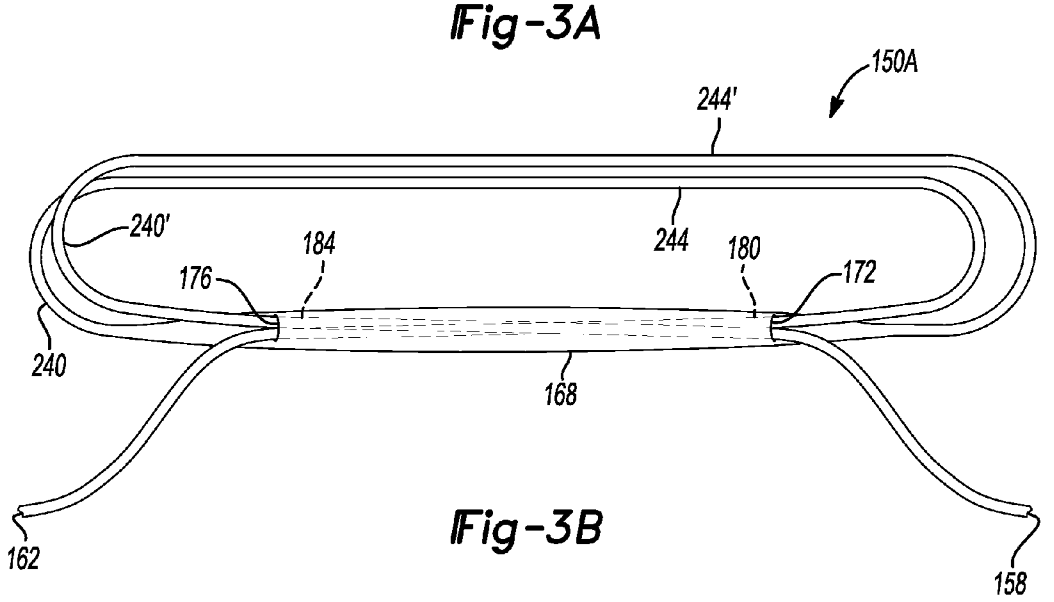

With reference to FIG. 3B and continuing reference to FIGS. 3 and 3A, an alternative adjustable flexible member construct 150A is shown. Construct 150A can be formed to include a double loop configuration having two loops 240, 240' that each traverse a path from one end of passage portion 168 to the other end thereof, instead of each loop being disposed at respective opposite ends of passage portion 168 as in construct 150. Flexible member construct 150A can be formed by passing the first end 158 of the flexible member through aperture 176, through passage portion 168 and out aperture 172. The second end 162 can be passed through aperture 172, through the passage portion 168 and out the aperture 176. In various aspects, the first and second apertures 172, 176 can be formed during the braiding process as loose portions between pairs of fibers defining the flexible member 154, as discussed above. Passing ends 158, 162 through the apertures 172, 176 can form the loops 240, 240'. The loops 240, 240' can define mount or summit portions 244, 244' of the adjustable flexible member construct 150A and can be disposed generally opposite from the passage portion 168. Flexible member construct 150A can be used, for example, to compress a fractured or sectioned bone or to close a sectioned sternum in sternal closure procedures, as will be discussed herein.

The longitudinal and parallel placement of the first and second ends 158 and 162 of the flexible member 154 within the passage portion 168 resists the reverse relative movement of the first and second portions 180, 184 of the flexible member construct 150A once it is tightened. The tensioning of the ends 158 and 162 can cause relative translation of the portions 180, 184 relative to passage portion 168. Upon applying tension to the first and second ends 158 and 162, the loops 240, 240' can be reduced to a desired size or placed in a desired tension. Tension in the loops 240, 240' can cause the body of the flexible member 154 defining the passage portion 168 to be placed in tension and therefore cause passage portion 168 to constrict about the portions 180, 184 similarly to the constriction discussed above with respect to construct 150. This constriction can cause the adjustable flexible member construct 150A to "automatically" lock in a reduced size or smaller diameter configuration. A further discussion of the flexible member constructs 150, 150A are provided in U.S. patent Ser. No. 11/541,506 filed on Sep. 29, 2006 entitled "Method and Apparatus for Forming a Self-Locking Adjustable Suture Loop" assigned to Biomet Sports Medicine, LLC, and the disclosure is incorporated by reference.

Referring now to FIGS. 4-16, the use of flexible member constructs 10, 150 and 150A in various assembly configurations and exemplary sternal closure procedures will now be described. With particular reference to FIGS. 4 and 5, a sternum 304 is shown having a section or cut 308 separating sternal portions 312, 316, such as may be performed in connection with cardiac surgery. Flexible member constructs 10, 150, 150A alone, or in various combinations with each other or additional fixation devices, can be used to compress and secure sternal portions 312, 316 together to assist healing, as will be discussed herein.

Figure 4:
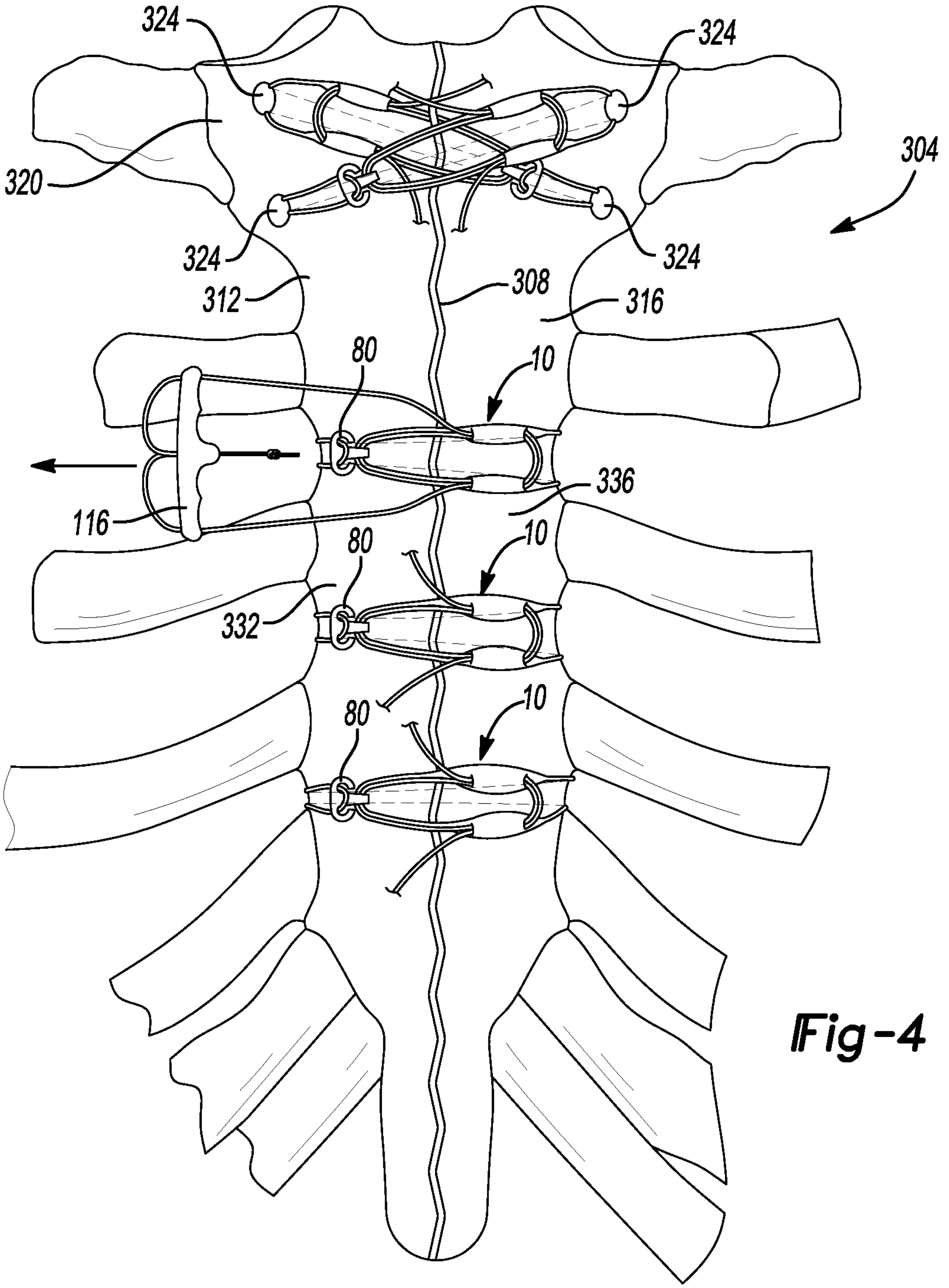
FIGS. 4 and 5 depict exemplary views of the adjustable flexible member construct of FIG. 1 in a surgical procedure for sternal closure according to the present teachings.
Figure 5:
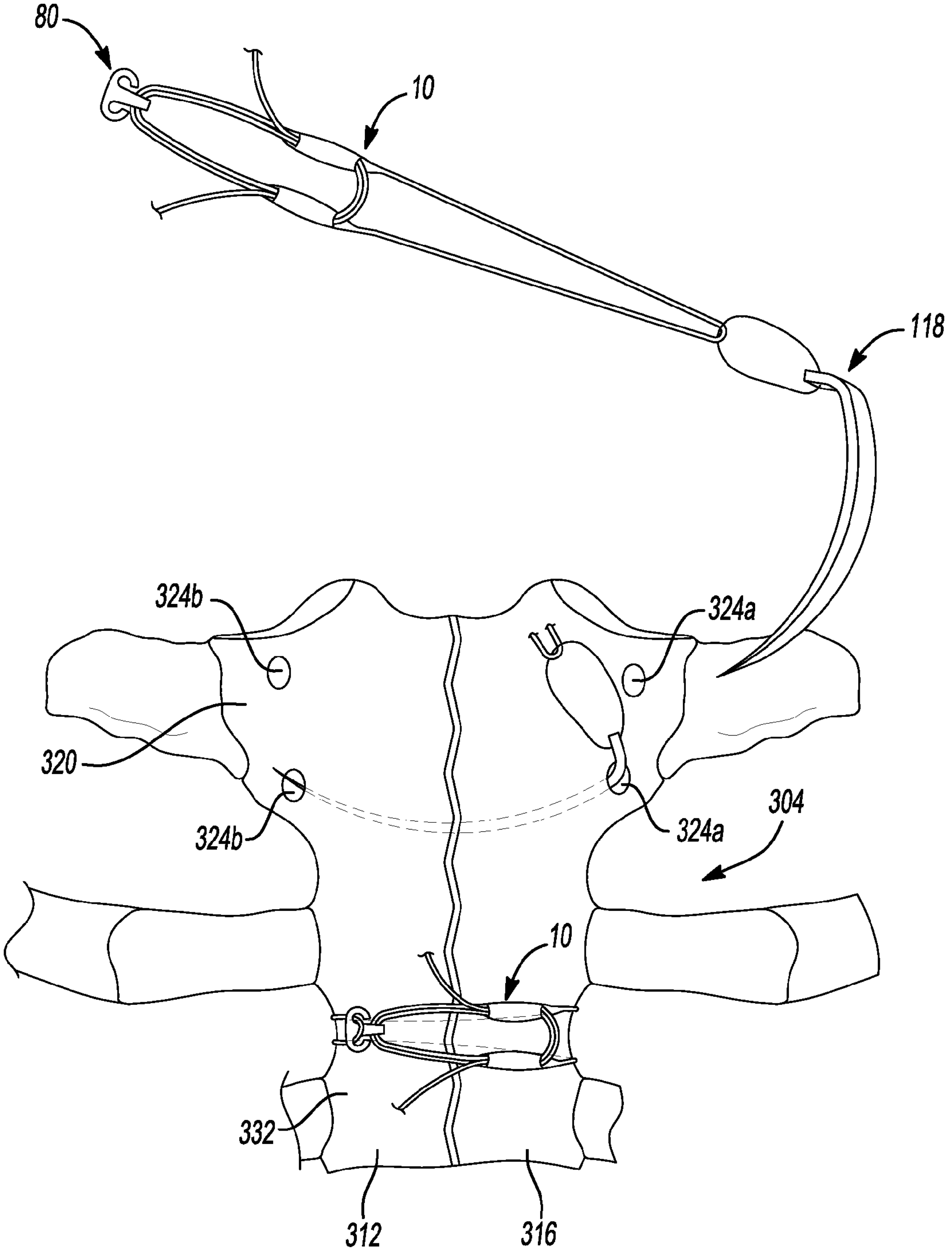

In FIGS. 4 and 5, adjustable flexible member construct 10 is shown in various configurations to compress sternal portions 312, 316 toward each other to close section 308. In one exemplary configuration, two flexible member constructs 10 can be used in a diagonal pattern in the manubrium 320 of the sternum in connection with two pairs of diagonally opposite holes 324 formed in the manubrium 320. While the diagonal pattern of flexible member construct 10 is shown in the manubrium 320 in FIG. 4, a non-diagonal or medial-lateral configuration can alternatively be used, as generally shown in FIG. 5.

To secure flexible member construct 10 to the manubrium 320, passing member 118 can be inserted through a first hole 324*a* of a respective pair of holes 324*a*, 324*b* and directed towards a corresponding second hole 324*b*, as shown in FIG. 5. A surgeon or the like can pull the passing member through the second hole 324*b* thus routing at least the fixed portion 34 through the first and second holes 324*a*, 324*b*. Fixed portion 34 can then be secured to attachment member 80, as shown in FIG. 4. Once fixed portion 34 is secured to the attachment member, first and second ends 18, 26 can be pulled or tensioned to reduce the loops 66, 70 to a desired size and to place construct 10 in a desired tension to compress and close the sectioned sternum 304. Ends 18, 26 of construct 10 can be tensioned by pulling on the respective ends as discussed above, or with the use of the handle 116, as generally shown in FIG. 4. Handle 116 can provide the surgeon with an ability to easily tension ends 18, 26 simultaneously and evenly. Handle 116 can then be removed and discarded. Handle 116 can be used to evenly tension loops 66, 70 as discussed above, or can be used to tension loops 66, 70 at different rates by manipulating an angle of handle 116 so that, for example, a first loop of loops 66, 70 can be tensioned at a faster rate than a second loop of loops 66, 70. In this manner, the first loop can reach a desired final tension before the second loop. In one exemplary configuration, the smaller diameter flexible member can be used with construct 10 in manubrium 320 for easier manipulation through holes 324.

Flexible member construct 10 can also be used to compress a body 332 of sternum 304, as also shown in FIGS. 4 and 5. For the body 332, construct 10 can be wrapped around the sternum and fixed portion 34 can be secured to attachment member 80 such that ends 18, 26 extend from an anterior side 336 of body 332, as shown in FIG. 4. In the exemplary configuration shown in FIG. 4, three flexible member constructs 10 are shown securing the body 332 of the sternum 304. Nevertheless, more or fewer flexible constructs than shown can be used in the intercostal spaces between the ribs to secure the body of the sternum, as may be determined by a surgeon during a sternal closure procedure. In addition, the larger diameter flexible member construct 10 can be utilized in body area 332 of sternum 304, according to one exemplary configuration. The larger diameter flexible member can enable more tension to be applied to the bone or sternum without cutting into or damaging the bone.

The flexible member constructs 10 can be attached and tensioned or secured to the sternum 304 in various orders. For example, flexible member constructs 10 can first be attached to the manubrium 320 and then to the body 332, or vice-versa. Additionally, flexible member constructs 10 can be tensioned in various orders, such as initially tensioning each flexible member construct 10 to a snug or non-slack condition and then further tensioning each construct 10 to a final desired tension. As discussed above, constructs 10 can be tightened with or without use of handle 116. Flexible construct 10 can automatically lock under tension, as also discussed above, after which a portion of ends 18, 26 can be trimmed and removed.

Flexible member construct 10 also can be provided with an antibiotic and/or platelet concentrate coating to resist bacterial adhesion and/or promote healing. In this regard, flexible member construct 10, as well as other constructs discussed herein, can be pre-configured with such a coating or the coating can be applied intraoperatively. Further, the surgeon can also apply the platelet coating to the sectioned area during the sternal closure procedure.

Figure 6:
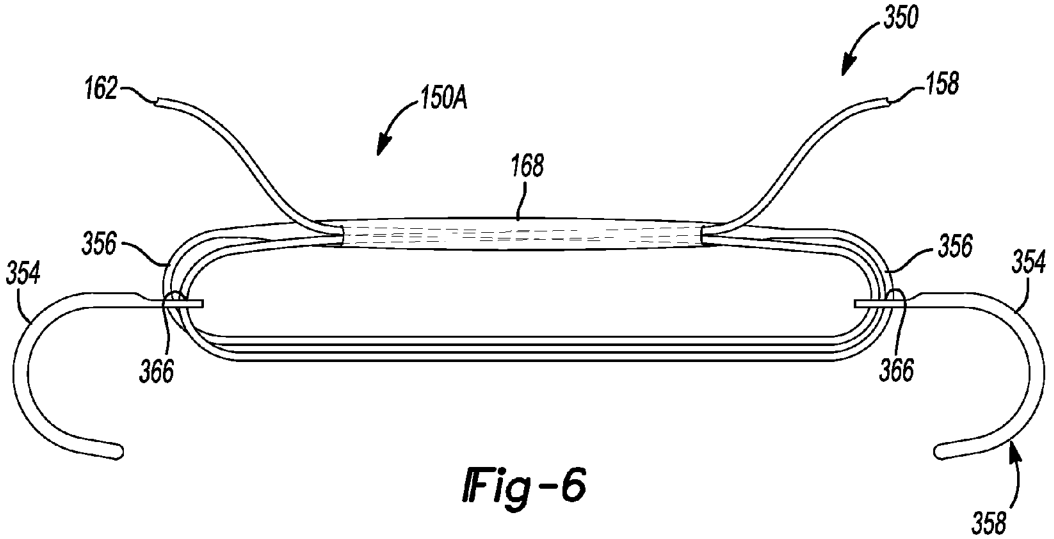
FIGS. 6-9 depict views of exemplary alternative attachment members associated with one or more of the adjustable flexible member constructs according to the present teachings.
Figure 10:
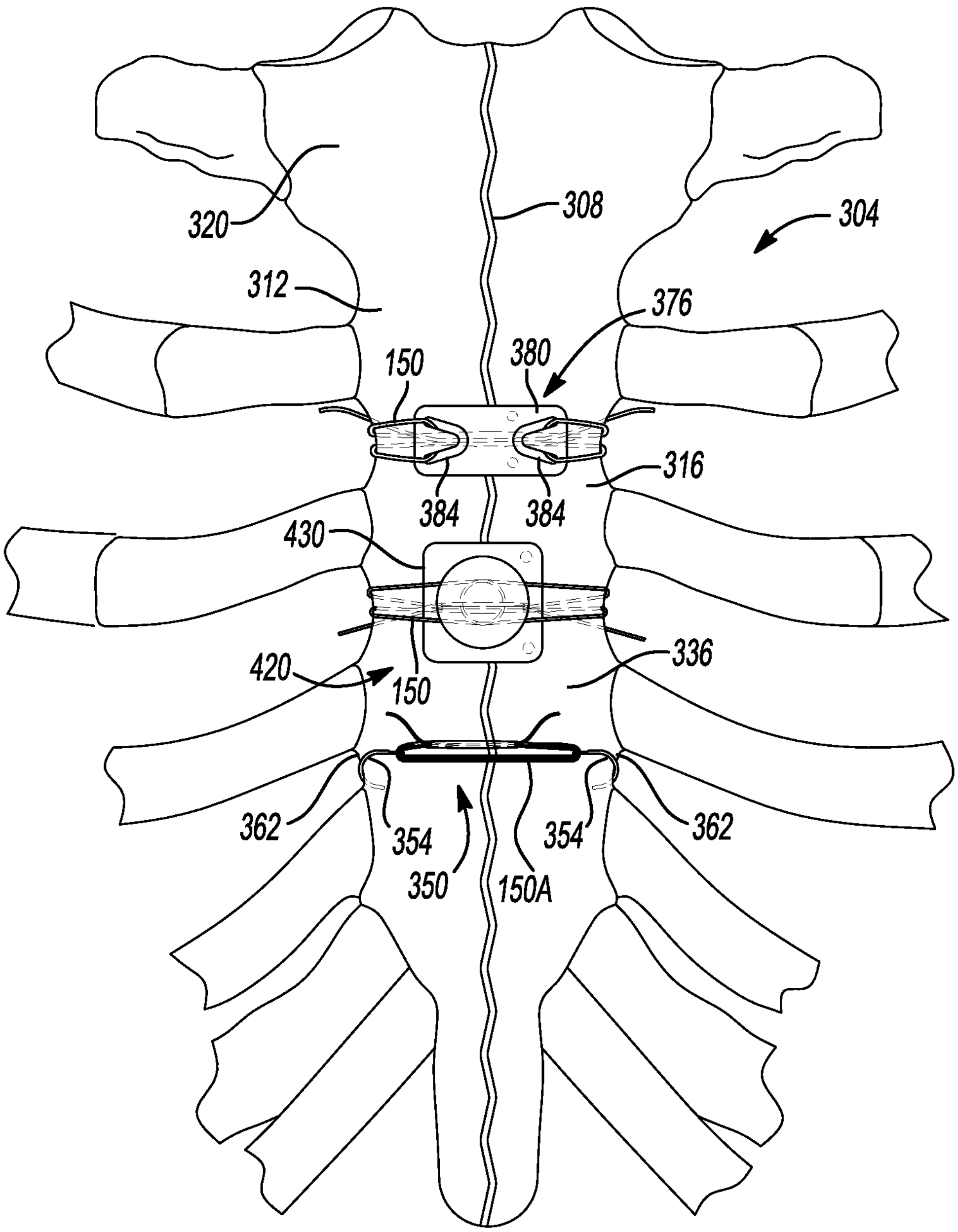
FIGS. 10 and 11 depict views of the attachment members of FIGS. 6-9 in exemplary configurations for use in a sternal closure procedure according to the present teachings.

With additional reference to FIGS. 6 and 10, flexible member construct 150A is shown in an assembly configuration 350 having a pair of attachment members 354 coupled to opposed sides 356 of loops 240 and 240'. Attachment members 354 can include a generally arcuate shape 358 and, in the exemplary configuration shown in FIG. 6, a generally semicircular shape or U-shape. The shape 358 of attachment members 354 can be used to secure the attachment members 354 to medial and lateral sides 362 of sternum 304, as generally shown in FIG. 10. Attachment members 354 can include an aperture 366 for receiving loops 240, 240' therethrough, as shown in FIG. 6. In an exemplary configuration, flexible member construct 150A can be formed integrally with attachment members 354 for use in a sternal closure or other fracture reduction procedure. In this manner, attachment members 354 can be preformed and coupled to loops 240, 240' to form assembly configuration 350, which can be provided in the assembly configuration for use in the sternal closure procedure.

With particular reference to FIG. 10, construct 150A in the assembly configuration 350 can be used to compress the sternum 304 by securing attachment members 354 to the sides 362 of sternal portions 312, 316 and then applying tension to ends 158, 162 of construct 150A. The adjustable loops of construct 150A can then be reduced to the desired size and placed in the desired tension to compress sternum 304 about section 308. Flexible member construct 150A can automatically lock under tension to maintain the reduced size of loops 240, 240', as discussed above. It should be appreciated that while attachment members 354 are described above in connection with flexible member construct 150A, the attachment members 354 can also be used with alternative flexible member constructs, such as construct 150.

Figure 7:
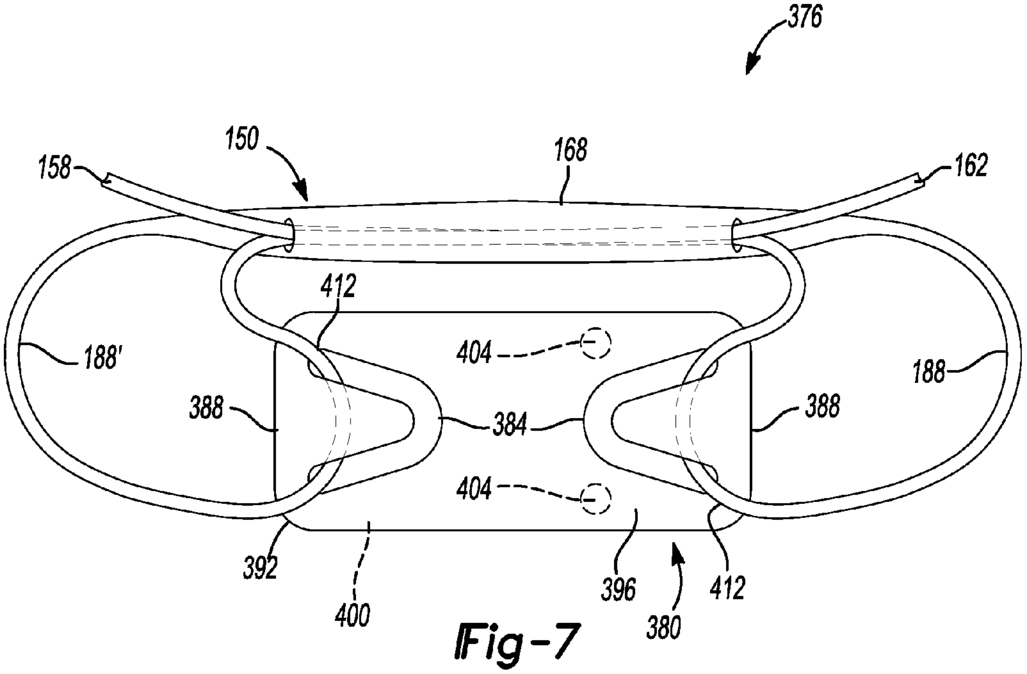

Turning now to FIG. 7 and with reference to FIG. 10, flexible member construct 150 is shown in an assembly configuration 376 operatively associated with an attachment member or frame 380. Frame 380 can be used to facilitate securing flexible member construct 150 around a fractured bone or the sectioned sternum 304 to compress the fracture or section and affect healing. Frame 380 can include a pair of attachment portions 384 at opposed ends 388 of the frame. In the exemplary configuration shown, frame 380 can include a generally rectangular plate 392 and the attachment portions 384 can be in the form of V-shaped apertures extending through plate 392 from a top surface 396 to a bottom surface 400, as shown in FIG. 7. Bottom surface 400 can optionally include a pair of fixation members 404 to prevent movement of frame 380 relative to the sternum 304 upon placement thereon. Fixation members 404 can include spikes, posts, screws, adhesive or the like that are coupled to or pass through or extend from the bottom surface 400.

With additional reference to FIG. 10, flexible member construct 150 in the assembly configuration 376 is shown with the bottom surface of frame 380 positioned on the anterior side 336 of sternum 304. Flexible member construct 150 can then be wrapped around sternum 304 and opposed ends 412 of loops 188, 188' can be secured to frame 380 via attachment portions 384. In this configuration, passage portion 168 can be positioned on a posterior side of sternum 304, as generally shown in FIG. 10. Ends 158, 162 of construct 150 can then be tensioned to reduce the loops 188, 188' to the desired size and tension to compress and close section 308 and assist healing of sternum 304. Flexible member construct 150 can automatically lock and maintain the reduced size of loops 188, 188' under tension, as discussed above. It should be appreciated that frame 80 can also be used with flexible member construct 10.

Figure 8:
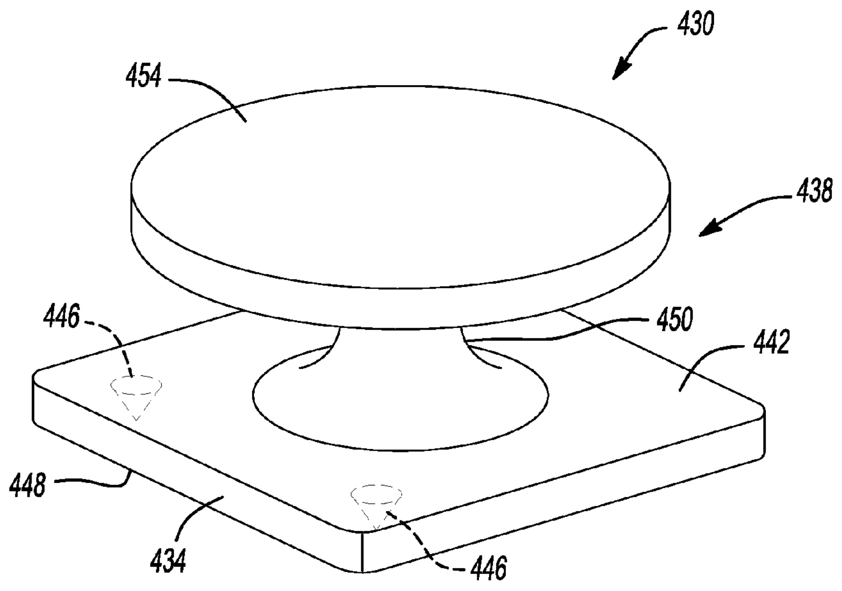

Referring now to FIGS. 8 and 10, flexible member construct 150 is shown in an assembly configuration 420 operatively associated with an attachment member or frame 430. Frame 430 can include a base 434, a post 438 extending from an upper surface 442 of base 434, and at least one optional fixation member 446 extending from a lower surface 448 of base 434. Fixation member 446 can include spikes, posts, screws, adhesive or the like that are coupled to or extend from lower surface 448. Post 438 can include a reduced diameter neck portion 450 coupled to the base and a larger diameter or head portion 454 coupled to the neck portion 450 and configured to retain loops 188, 188' of construct 150, as discussed below. Frame 430 can be placed on sternum 304 with lower surface 448 engaging the anterior side 336 of sternum 304, as shown in FIG. 10. Flexible member construct 150 can be wrapped around sternum 304 in one of the intercostal spaces and each loop 188, 188' can be secured to the frame 380 via post 438, as also shown in FIG. 10.

In this exemplary configuration, passage portion 168 can be positioned on the posterior side of sternum 304. Once frame 430 is positioned and construct 150 is wrapped around the sternum and secured to post 438, ends 158 and 162 extending from the posterior side of sternum 304 can be tensioned. Applying tension to ends 158, 162 can reduce loops 188, 188' to a desired size and tension to compress sectioned sternal portions 312, 316 together to assist healing at section 308, as generally shown in FIG. 10. Flexible construct 150 can automatically lock loops 188, 188' under tension to maintain the reduced size of loops 188, 188' and compression of sternal portions 312, 316 together, as discussed above.

It should be appreciated that while reference to FIG. 10 has been made with respect to the assembly configurations 350, 376 and 420, these assembly configurations have been combined in one figure for illustration purposes only and need not be used together. In this regard, an exemplary sternal closure procedure could utilize only one of the assemblies shown in the intercostal spaces, or combinations thereof, as may be desired by a particular surgeon performing a sternal closure procedure. It should also be appreciated that assemblies 350, 376 and 420 could be used individually or in various combinations with flexible member constructs 10 secured to the manubrium 320, as discussed above with reference to FIG. 4.

Figure 9:
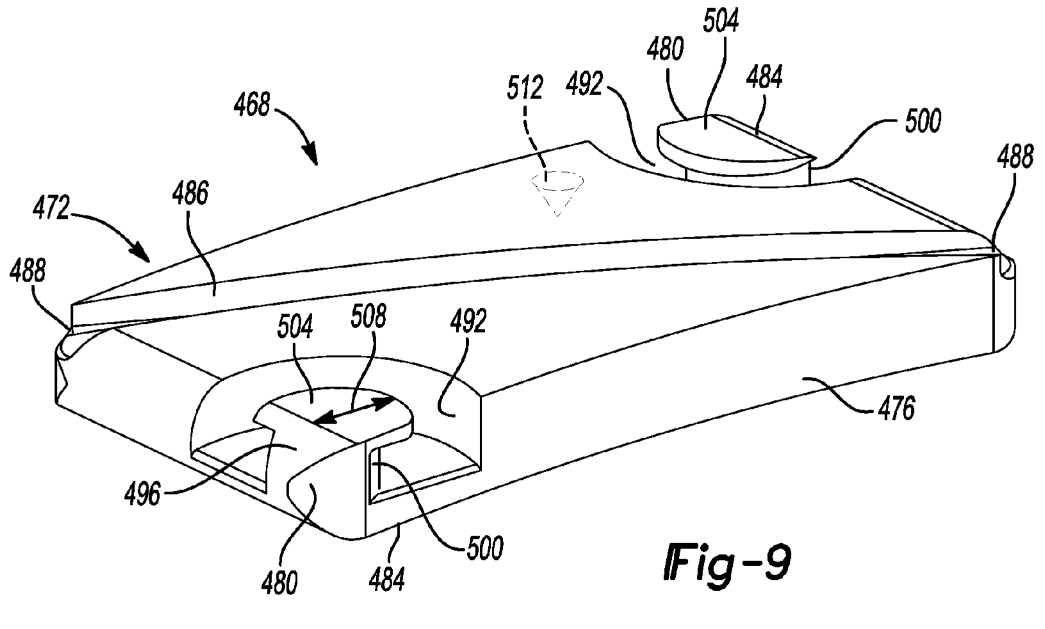
Figure 11:
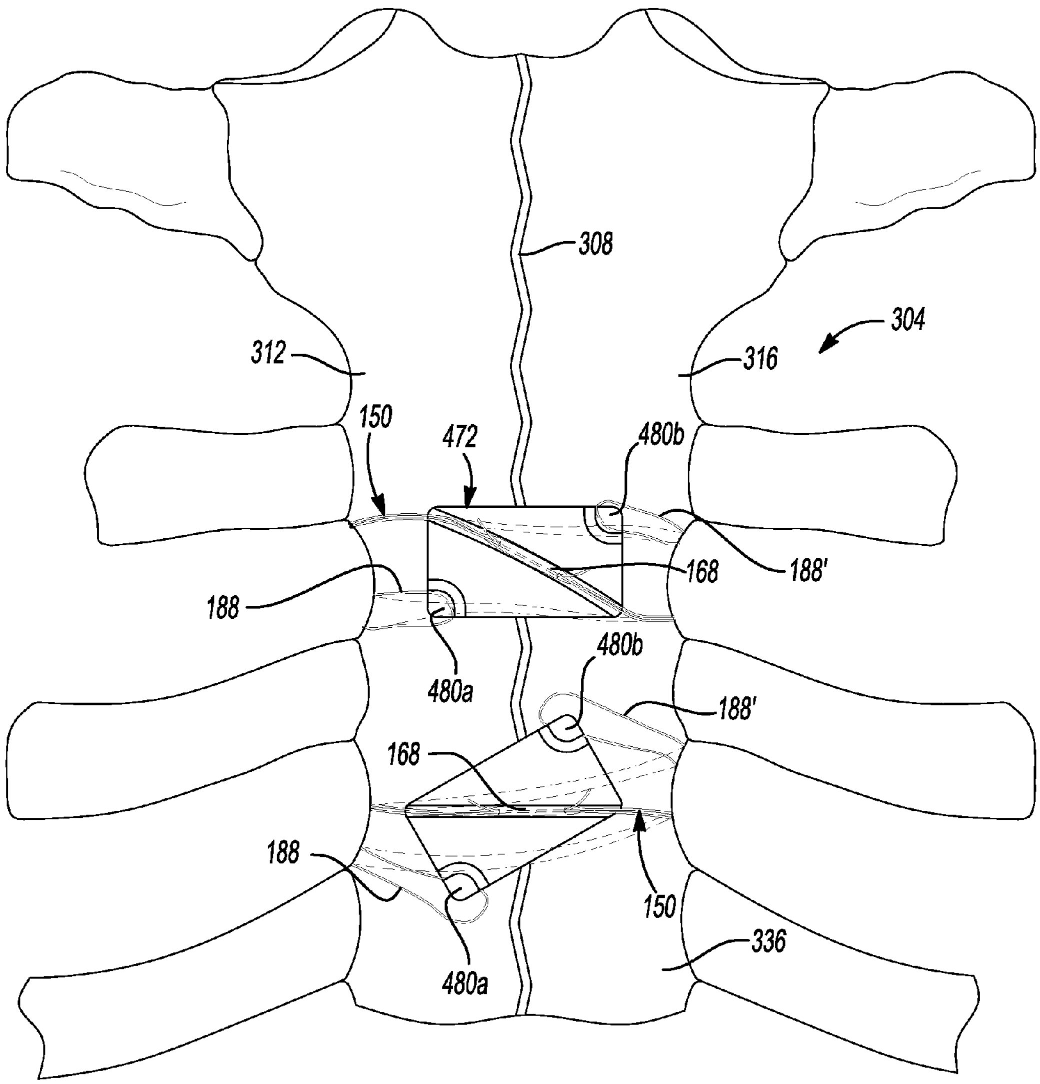

Referring now to FIGS. 9 and 11, adjustable flexible member construct 150 is shown in an assembly configuration 468 operatively associated with a frame 472. As shown in FIG. 9, frame 472 can include a generally rectangular body 476 with attachment portions 480 positioned at one pair of diagonally opposed corners 484 and a groove or channel 486 extending diagonally across a top surface of frame 472 from a second pair of opposed corners 488. While frame 472 is shown having rectangular body 476, it should be appreciated that frame 472 can be configured in other shapes, such as various polygonal shapes for use in coupling frame 472 to flexible member construct 150, as will be described below. Attachment portions 480 can each include a recess 492 at least partially surrounding a post 496. Post 496 can include a neck portion 500 and a cap or head portion 504 having a width dimension 508 greater than a corresponding width of neck portion 500 such that at least a portion of head portion 504 overhangs neck portion 500, as shown in FIG. 9. At least one optional fixation member 512 can extend from a bottom surface 516 of frame 472.

With particular reference to FIG. 11, frame 472 can be positioned in various configurations relative to sternum 304, as illustrated by the two exemplary configurations shown in FIG. 11. Frame 472 can be positioned on sternum 304 such that the bottom surface 516 engages the anterior side 336 of sternum 304. Flexible member construct 150 can be wrapped around sternum 304 within an intercostal space thereof and loops 188, 188' can be coupled to respective attachment portions 480. More specifically, flexible construct 150 can be placed in channel 486 such that passage portion 168 is positioned within channel 486, as shown in FIG. 11. Positioning construct 150 in channel 486 can provide a low profile closure arrangement that can be more conformable or provide less discomfort to a recipient patient. Loop portion 188 can then be wrapped around the posterior side of sternum 304 in one direction and coupled to attachment portion 480A of the pair of attachment portions 480. Similarly, loop portion 188' can be wrapped around the posterior side of sternum 304 in an opposite direction of loop 188 and then be coupled to attachment portion 480B. Tension can then be applied to ends 158, 162 to reduce the size of loops 188, 188' to compress sternal portions 312, 316 together to assist healing of sectioned sternum 304 at section 308. Flexible member construct 150 can automatically lock loops 188, 188' at the desired reduced size under tension, as discussed above. In addition, placing frame 472 over the section can also stabilize the sternum to align sternal portions 312, 316 to be co-planar.

Flexible member construct 150 in the assembly configuration 468 can be used alone or in various combinations with flexible member constructs 10 and 150A and/or assembly configurations 350, 376 and 420 discussed above. For example, flexible member constructs 10 can be used in the manubrium 320 as shown in FIG. 4 and assembly 468 can be used alone or in various combinations with assemblies 350, 376 and 420 in the body 332 to compress sternal portions 312, 316, as discussed above.

Figure 12:
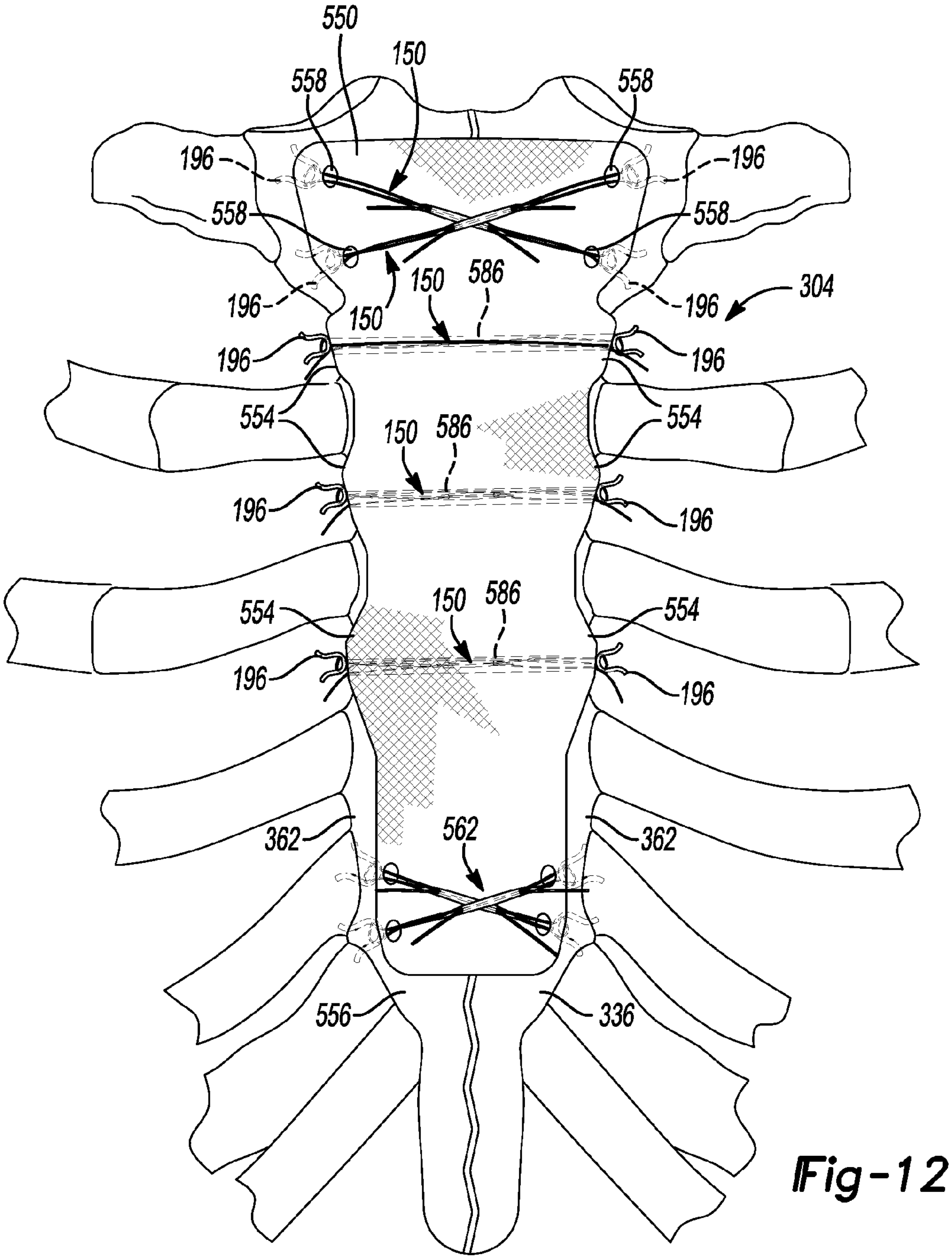
FIG. 12 depicts a view of an exemplary use of the flexible member construct of FIG. 3A in a surgical method for sternal closure according to the present teachings.

Referring now to FIG. 12, adjustable flexible member construct 150 is shown operatively associated with anchors 196 and an orthopedic mesh 550 for use in a sternal closure procedure. More particularly, orthopedic mesh 550 can be positioned on the anterior side 336 of sternum 304 such that portions 554 extend around the lateral sides 362 in the intercostal spaces, as shown in FIG. 12. The orthopedic mesh 550 can be, for example, a product sold by Biomet Sports Medicine, LLC under the name SportMesh™. With the orthopedic mesh 550 positioned on sternum 304 as discussed above, construct 150 with anchors 196 can be used in various configurations to compress the sectioned sternum 304 at section 308, as generally shown in FIG. 12.

The orthopedic mesh 550 can be coated with the platelet concentrate discussed above, and/or antibiotics, bone growth agents, etc. to aid in soft tissue healing. The mesh 550 can provide a barrier between the flexible member constructs and the bone to aid in transferring load from the flexible member construct to the mesh 550, which can decrease the pressure applied to the bone by the tensioned flexible member construct. The mesh 550 can be particularly useful, for example, in patients with soft bone tissue. It should also be appreciated that load distribution in the intercostal spaces can be provided by the portions 554 that extend around the medial and lateral sides. Moreover, the orthopedic mesh can aid in the retention of anchors 196, particularly where the bone tissue may be soft.

In one exemplary configuration, four holes 558 can be formed through the mesh 550 and the manubrium 320. Flexible anchors 196 associated with two flexible member constructs 150 can be inserted through respective diagonal pairs of holes 558 through the manubrium, as shown in FIG. 12. The constructs 150 can be in diagonal overlapping pattern and be disposed primarily on top of the orthopedic mesh 550. Upon tensioning the free ends 158, 162 of each construct 150, the tail portions 220, 224 of anchors 196 can engage the posterior manubrium adjacent holes 558 and provide anchoring resistance to retain the anchors 196 outside of holes 558 on the posterior side of the sternum 304. The loops 188, 188' subsequently can be reduced to the desired size or tension to compress sternal portions 312, 316 and assist closure and healing of the sectioned sternum. The orthopedic mesh 550 can work to distribute the load placed on the anterior side 336 of the sternum by the constructs 150 under tension. A similar configuration 562 can be used at a lower portion 566 of the sternum 304 adjacent the Xiphoid process, as also shown in FIG. 12. It should be appreciated that configuration 562, as well as the configuration discussed immediately above with respect to the manubrium, can alternatively be in a parallel transverse pattern as opposed to the illustrated diagonal patterns.

Continuing with FIG. 12, adjustable flexible construct 150 having a pair of anchors 196 attached to respective loops 188, 188' can be inserted through transverse bores 586 formed in sternum 304. In particular, the constructs 150 can be positioned in bores 586 such that the passage portions 168 are each aligned in a respective bore 586, as shown in FIG. 12. The constructs 150 can be pierced or routed through the portions 554 of orthopedic mesh 550 that extend around the lateral sides of sternum 304 so as to provide additional anchoring resistance and load distribution for flexible anchors 196, as shown in FIG. 12. Ends 158, 162 can be tensioned to compress sternal portions 312, 316, as discussed herein. It should be appreciated that while orthopedic mesh 550 is shown in FIG. 12 with reference to construct 150 and flexible anchors 196, orthopedic mesh 550 can be used in various other sternal closure configurations disclosed herein, for example, to distribute a load applied by the various disclosed flexible member constructs relative to the sternum 304.

Figure 13:
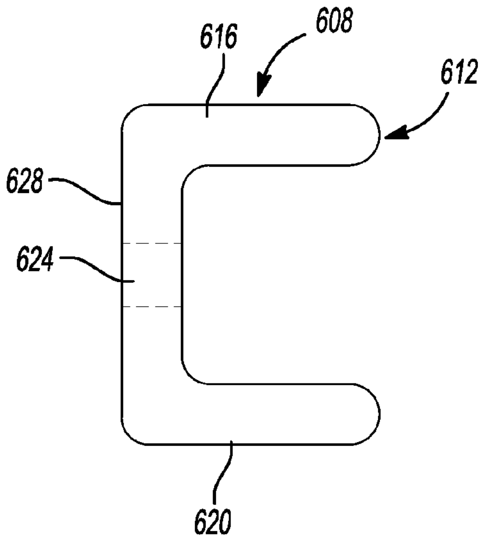
FIG. 13 depicts an exemplary alternative attachment member according to the present teachings.
Figure 14:
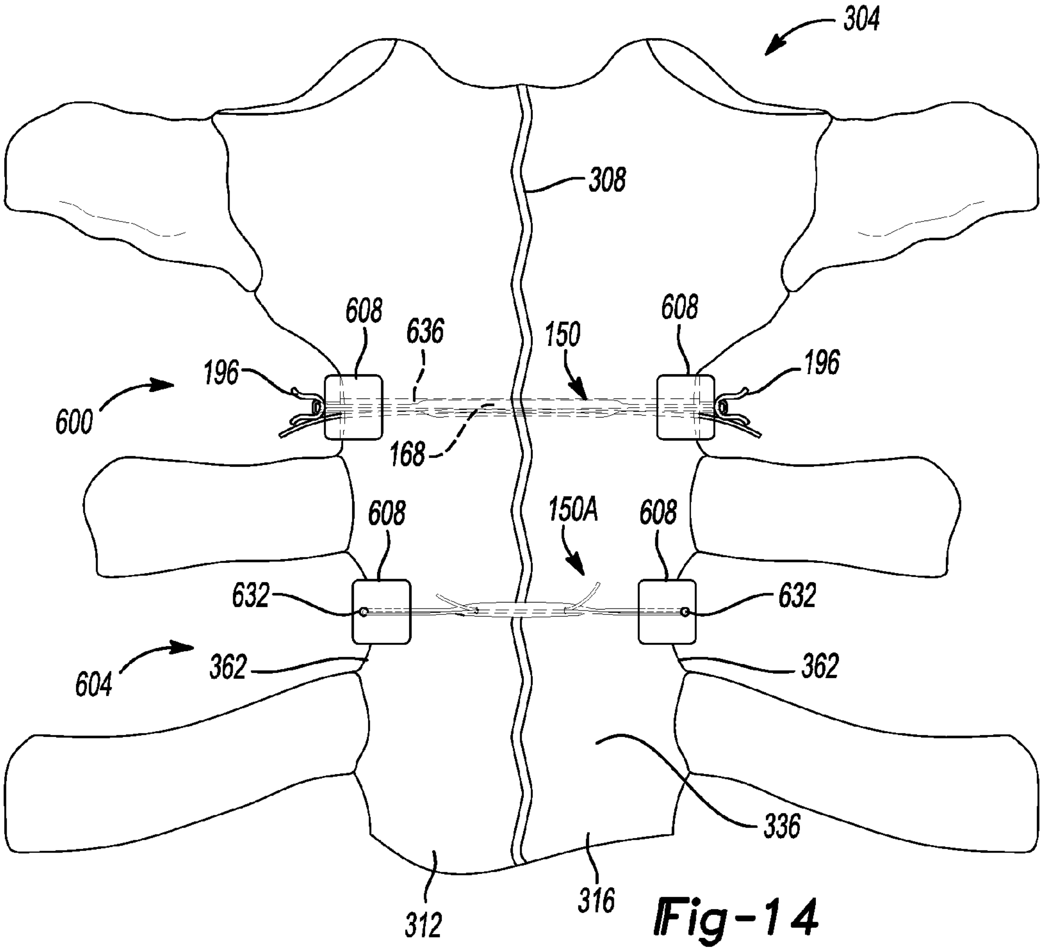
FIG. 14 depicts exemplary configurations of the attachment member of FIG. 13 associated with various adjustable flexible member constructs according to the present teachings.

Referring now to FIGS. 13 and 14, adjustable flexible member construct 150 is shown in exemplary assembly configurations 600 and 604 operatively associated with attachment members 608. Each attachment member 608 can include a body 612 having a substantially U-shaped configuration and can be sized for positioning about the lateral sides 362 of sternum 304 such that top and bottom portions 616, 620 extend about the respective anterior and posterior sides of the sternum, as shown in FIG. 14. In one exemplary configuration, attachment member 608 can include an aperture 624 positioned within a side portion 628 connecting the top and bottom portions 616, 620. In another configuration, attachment member 608 can include an aperture 632 in the top portion 616, as shown in FIG. 14. Aperture 632 can be in lieu of or in addition to aperture 624.

With reference to assembly configuration 600, flexible member construct 150 with anchors 196 can be positioned through transverse bore 636 in sternum 304 such that passage portion 168 is positioned within the bore. Each respective loop 188, 188' with anchors 196 can be passed through aperture 624 in attachment member 608 such that the anchors 196 are on a first side of portion 628 opposite a second side adjacent the sternum 304. Ends 158, 162 can then be tensioned thereby reducing a size of loops 188, 188' so as to draw attachment members 608 against the lateral sides of sternum 304 and compress sternal portions 312, 316 together. Flexible member construct 150 can automatically lock the loops in the reduced diameter configuration under tension, as described herein. Attachment members 608 can facilitate distributing a compression load applied to the sternum by the tensioned construct 150, which can enable more tension to be applied.

With continuing reference to FIG. 14, assembly configuration 604 can include attachment members 608 integrally formed or pre-assembled with flexible member construct 150A such that loops 240, 240' are coupled to apertures 632. In this configuration, attachment members 608 can be positioned against the respective lateral sides of sternum 304, similar to assembly configuration 600 discussed above. Flexible member construct 150A can be positioned relative to the anterior side 336 of sternum 304 such that it does not wrap around or extend through sternum 304. It should be appreciated that assembly configurations 600, 604 can be used alone or with various other flexible member construct and assembly configurations disclosed herein to compress sternal portions 312, 316 to assist healing of sectioned sternum 304.

Figure 15:
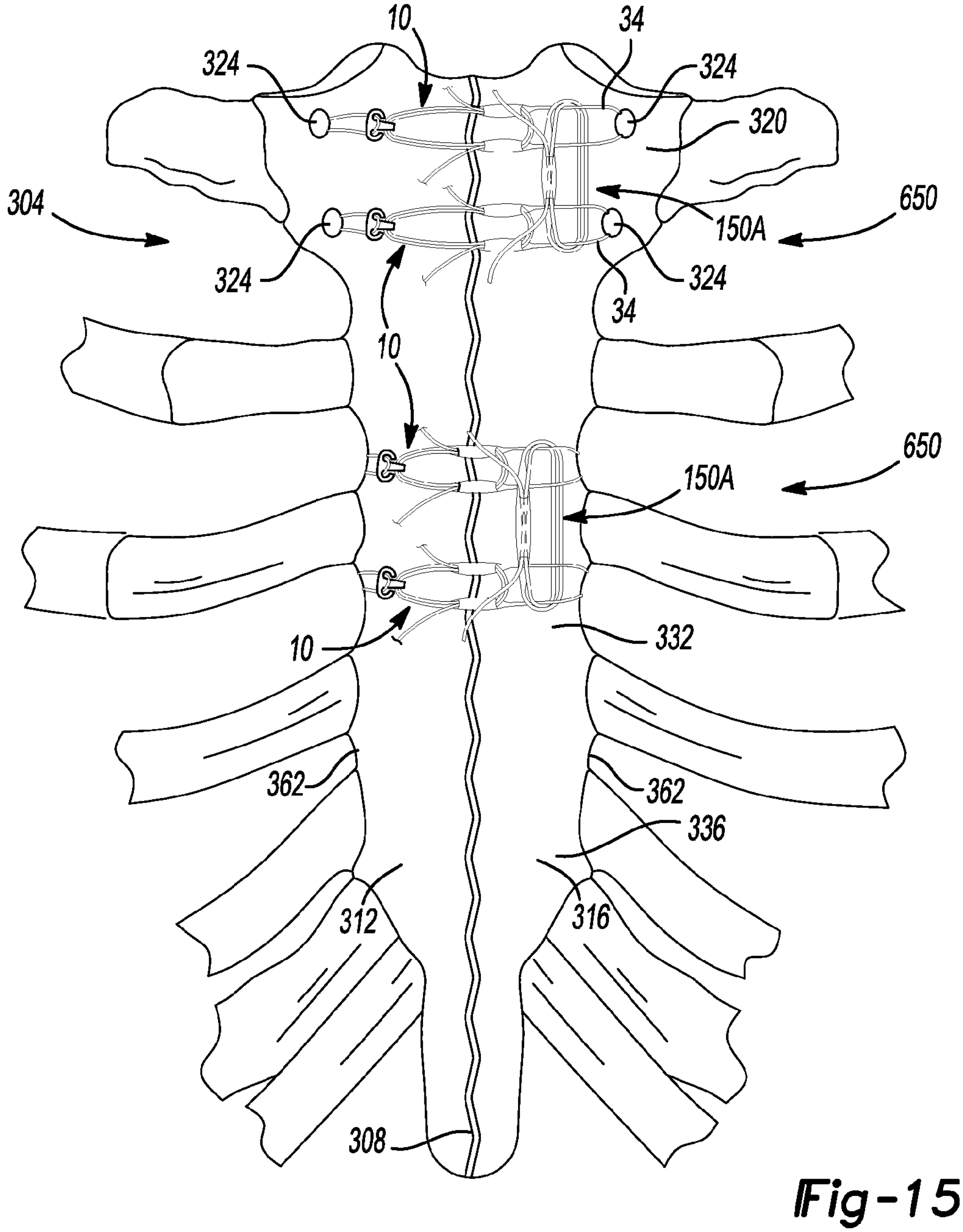
FIG. 15 depicts an exemplary surgical method for sternal closure according to the present teachings.

Turning now to FIG. 15, an alternative configuration 650 for compression of sternum 304 in a sternal closure procedure is provided. Configuration 650 can include two flexible member constructs 10 in a transverse orientation in the manubrium 320, as generally discussed above with reference to FIGS. 4 and 5. Configuration 650 can also include flexible member construct 150A coupled around the two constructs 10 before fixed portion 34 of each construct 10 is coupled to the respective attachment member 80, as shown in FIG. 15. Construct 150A can be positioned generally in a superior-inferior orientation perpendicular to the transverse orientation of constructs 10. Construct 150A can be tensioned after tensioning constructs 10 to draw any remaining tension from the system. In this configuration, constructs 10 can provide cross-tensioning generally perpendicular to section 308 and construct 150A can provide tensioning generally parallel to section 308. Configuration 650 can also be utilized to compress the body 332 of sternum 304, where constructs 10 are wrapped around the sternum 304 instead of through holes 324, as also shown in FIG. 15.

Figure 16:
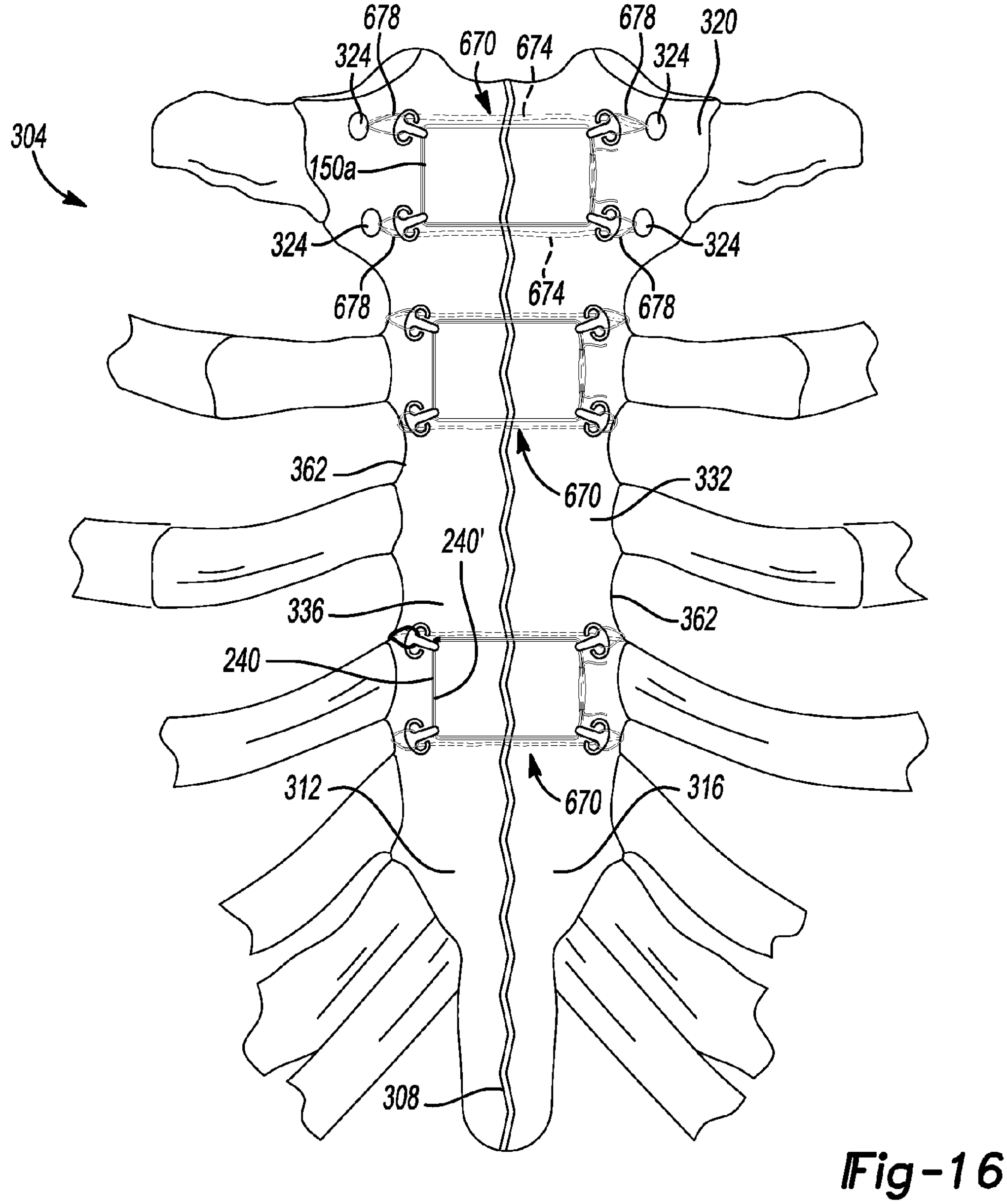
FIG. 16 depicts an exemplary surgical method for sternal closure according to the present teachings.

Referring now to FIG. 16, another alternative configuration 670 for compression of sternum 304 in a sternal closure procedure is provided. Configuration 670 can include two separate continuous suture or flexible member loops 674 having a fixed length. Alternatively, a flexible member construct, such as construct 150, can be used in place of fixed loops 674 to provide additional adjustment and tensioning capability. Flexible member construct 150A can be provided with four attachment members 80 integrally coupled to loops 240, 240'. In the manubrium area, loops 674 can be routed or passed along the posterior side of sternum 304 in a transverse orientation such that opposed ends 678 of loops 674 extend through a respective pair of holes 324, as shown in FIG. 16. The opposed ends 678 of each of loops 674 can be coupled to a respective two of the four attachment members 80. The ends 158, 162 of flexible member construct 150A can then be tensioned to compress sternal portions 312, 316, as discussed herein. Additional configurations 670 can be used to compress body 332 of sternum 304 where the fixed loops are wrapped around the sides of sternum 304 as opposed to being passed through holes 324, as also shown in FIG. 16. It should be appreciated that configurations 650 and 670 can be used alone or with various combinations of the flexible member constructs and assembly configurations discussed herein.

While one or more specific examples have been described and illustrated, it will be understood by those skilled in the art that various changes may be made and equivalence may be substituted for elements thereof without departing from the scope of the present teachings as defined in the claims. Furthermore, the mixing and matching of features, elements and/or functions between various examples may be expressly contemplated herein so that one skilled in the art would appreciate from the present teachings that features, elements and/or functions of one example may be incorporated into another example as appropriate, unless described otherwise above. Moreover, many modifications may be made to adapt a particular situation or material to the present teachings without departing from the essential scope thereof.

What is claimed is:

1. A method for securing a fractured or sectioned sternum in a patient's body, comprising:

forming an adjustable flexible member construct including:

providing a flexible member having first and second ends and a body defining first and second passage portions spaced apart from each other by a first portion of the flexible member;

passing the first end into and through the second passage portion and then into and through the first passage portion to form a first loop;

passing the second end into and through the first passage portion in an opposite direction as the first end and then into and through the second passage portion in an opposite direction as the first end to form a second loop; and coupling an attachment member to the first and second loops;

encircling the fractured or sectioned sternum by at least partially wrapping the formed adjustable flexible member construct about the sternum;

coupling the first portion of the adjustable flexible member construct opposite the loops to the attachment member; and reducing the adjustable flexible member construct to compress the fractured or sectioned sternum.

2. The method of claim 1, wherein reducing the adjustable flexible member construct to compress the fractured or sectioned sternum comprises applying tension to the first and second ends of the adjustable flexible member construct such that a size of the first and second loops is decreased thereby compressing the fractured or sectioned sternum; and wherein the adjustable flexible member construct automatically remains in a reduced position about the sternum.

3. The method of claim 2, further comprising:

forming first and second pairs of holes through a manubrium of the sternum, each pair of holes being on opposed sides of a section or fracture of the sternum; wherein forming a flexible member construct includes forming a plurality of flexible member constructs;

passing a first flexible member construct of the plurality of formed flexible member constructs through the first pair of holes and a second flexible member construct of the plurality of formed flexible member constructs through the second pair of holes such that the attachment members and passing portions of the first and second flexible member constructs are on an anterior side of the sternum;

coupling first portion of the first and second flexible member constructs opposite the loops to their respective attachment members; and reducing the first and second constructs to compress the fractured or sectioned sternum.

4. The method of claim 3, further comprising passing the first and second flexible member constructs through the first and second pairs of holes such that the first and second constructs overlap each other so as to form an X-shaped pattern.

5. The method of claim 3, further comprising:

encircling the sternum with a third flexible member construct of the plurality of formed flexible member constructs adjacent an intercostal space;

coupling the first portion of the third flexible member construct opposite the loops to its respective attachment member; and reducing the third adjustable flexible member construct to compress the fractured or sectioned sternum.

6. The method of claim 3, further comprising:

providing a single passage portion adjustable flexible member construct;

coupling the single passage portion adjustable flexible member construct to the first and second adjustable flexible member constructs before coupling the first portion of the first and second adjustable flexible member constructs to their respective attachment members; and tensioning the single passage portion adjustable flexible member construct to a reduced size after reducing the first and second constructs to reduce the fractured or sectioned sternum, the single passage portion adjustable flexible member construct automatically maintaining the reduced size.

7. The method of claim 6, wherein the single passage portion adjustable flexible member construct is orientated substantially perpendicular to the first and second adjustable flexible member constructs.

8. The method of claim 1, wherein encircling the fractured or sectioned sternum further comprises passing the adjustable flexible member construct around the posterior side of the sternum with a needle passing member detachably coupled to the first portion of the adjustable flexible member construct.

9. The method of claim 1, wherein forming an adjustable flexible member construct includes coupling the first and second ends to a tensioning member; and wherein reducing the adjustable flexible member construct to compress the fractured or sectioned sternum includes engaging the tensioning member to simultaneously decrease a size of the first and second loops to compress the fractured or sectioned sternum.

10. The method of claim 1, further comprising applying an orthopedic mesh to at least an anterior side of the fractured or sectioned sternum such that at least a portion of the adjustable flexible member construct rests on the orthopedic mesh.

11. The method of claim 10, further comprising applying a platelet concentrate, antibiotic concentrate, or combinations thereof, to the adjustable flexible member construct, the orthopedic mesh, or combinations thereof.

* * * * *

UNITED STATES PATENT AND TRADEMARK OFFICE

CERTIFICATE OF CORRECTION

PATENT NO. : 9,642,661 B2
APPLICATION NO. : 14/094311
DATED : May 9, 2017
INVENTOR(S) : Stone et al.

It is certified that error appears in the above-identified patent and that said Letters Patent is hereby corrected as shown below:

On the Title Page

In item (60), in "Related U.S. Application Data", in Column 1, Line 1-2, delete "Nov. 3, 210," and insert --Nov. 3, 2010,-- therefor On page 26, in Column 2, under "Other Publications", Line 20, delete "Reinforcment," and insert --Reinforcement,-- therefor On page 26, in Column 2, under "Other Publications", Line 56, delete "Rehalibitation" and insert --Rehabilitation-- therefor Signed and Sealed this
Thirty-first Day of July, 2018

Andrei Iancu
*Director of the United States Patent and Trademark Office*